United States Patent [19]
Mavrothalassitis et al.

[11] Patent Number: 5,856,125
[45] Date of Patent: Jan. 5, 1999

[54] ETS2 REPRESSOR FACTOR (ERF) GENETIC LOCUS AND ITS PRODUCTS

[75] Inventors: George J. Mavrothalassitis, Frederick; Donald G. Blair, Kensington; Robert J. Fisher, Sharpsburg; Gregory J. Beal, Jr., New Market; Meropi A. Athanasiou, Frederick, all of Md.; Dionyssios N. Sgouras, Athens, Greece

[73] Assignee: The United States of America as represented by the Department of Health and Human Services, Washington, D.C.

[21] Appl. No.: 469,412

[22] Filed: Jun. 5, 1995

[51] Int. Cl.⁶ .......................... C12N 15/12; C12N 15/09; C07K 14/47; C07K 14/82
[52] U.S. Cl. .................... 435/69.1; 536/23.5; 536/24.31; 530/350; 530/387.1
[58] Field of Search ................................. 536/23.5, 23.4, 536/24.31; 530/350, 387.1; 514/2, 44; 435/240.2, 325

[56] References Cited

PUBLICATIONS

AA. Klemsz, et al. "PE–1, a Novel ETS Oncogene Family Member, Localizes to Chromosome 1q21–q23" Genomics 20(2): 291–94 (Mar. 15, 1994).
Brunner, et al., *Nature*, 370:386–389 (1994).
Coffer, et al., *Oncogene*, 9:911–921 (1994).
Gunther, et al., *Genes Dev.*, 4:667–679 (1990).
Herschbach, et al., *Annu. Rev. Cell Biol.*, 9:479–509 (1993).
Janknecht, et al., *Biochim. Biophys. Acta*, 1155:346–356 (1993).
Janknecht, et al., *EMBO*, 12:5097–5104 (1993).
Karin, et al., *Curr. Opinion Cell Biol.*, 6:415–424 (1994).
Lai, et al., *Cell*, 70:609–620 (1992).
Leprince, et al., *Nature*, 306:395–398 (1983).
Macleod, et al., *TIBS*, 17:251–256 (1992).
Mavrothalassitis, et al., *Cell Growth Differ.*, 2:215–224 (1991).
Mavrothalassitis, et al., *Oncogene*, 5:1337–1342 (1990).
Mavrothalassitis, et al., *Proc. Natl. Sci. USA*, 87:1047–1051 (1990).
May, et al., *Proc. Natl. Acad. Sci. USA*, 90:5752–5756 (1993).
Naidu, et al., *Proc. Natl. Acad. Sci. USA* 91:5281–5285 (1994).
Nunn, et al., *Nature*, 306:391–395 (1992).
O'Neill, et al., *Cell*, 78:137–147 (1994).
Pabo, et al., *Annu. Rev. Biochem.*, 61:1015–1023 (1992).
Rahimi, et al., *DNA and Cell Biol.* 13(12):1189–1197 (1994).
Rao, et al., *Oncogene*, 9:1855–1860 (1994).
Roussel, et al., *Oncogene*, 9:405–415 (1994).
Savoysky, et al., *Oncogene*, 9:1839–1846 (1994).
Seth, et al., *Cell Growth Differ*, 3:327–334 (1992).
Seth, et al., *Oncogene*, 5:1761–1767 (1990).
Seth, et al., *Proc. Natl. Acad. Sci. USA*, 86:7833–7837 (1989).
Sgouras, et al., *EMBO Journal*, 14(19):4781–4793 (1995).
Tahara, *Cancer*, 15:1410–1470 (1995).
Tei, et al., *Proc. Natl. Acad. Sci. USA*, 89:6856–6860 (1992).
Treisman, et al., *Curr. Opinion Genet. Dev.*, 4:96–101 (1994).
Wasylyk, et al., *Eur. J. Biochem.*, 211:8–19 (1993).
Wasylyk, et al., *Nature*, 346:191–193 (1990).
Yu, et al., *Cell*, 76:933–945 (1994).
Yuan, et al., *J. Virol.*, 63:205–215 (1989).
Clipstone, N.A. et al. (1992) J. Cell Biochem. (Suppl O) 16 (Part B):222.

*Primary Examiner*—Stephen Walsh
*Assistant Examiner*—Michael D. Pak
*Attorney, Agent, or Firm*—Townsend & Townsend & Crew LLP

[57] ABSTRACT

The present invention relates, inter alia, to the ERF gene and to the products encoded by this gene. More particularly, the present invention relates to DNA sequences encoding ERF and AERF; polypeptides encoded by such DNA sequences; ERF chimeric molecules; and methods of using ERF and ERF chimeric molecules to reduce tumorigenicity in a tumor cell.

12 Claims, 16 Drawing Sheets

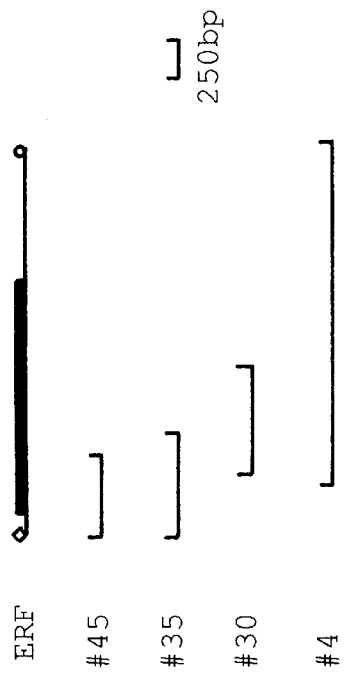

FIG. 1B-1.

```
341        Q  P  Q  R  P  D  K  C  P  L  P  P  M  A  P  E  T  P  P  V  P  S  S  A  S  S  S        367
1231  CTTCTTCCTCCCCATTCAAGTTTAAGCTCCACTCCGGACGCCGGCCCCCAGCTGGGAGAAGCCGTAGC        1312
368        S  S  S  S  S  P  F  K  F  F  K  L  Q  R  P  P  L  G  R  R  Q  R  A  A  G  E  K        395
1313  CGCTGCTGACAAGAGACCGGTGGCAGTGCAGGCGGGCCTAGCGCAGGGCCCCCGCCACCACAG        1394
396        A  V  A  A  D  K  S  G  G  S  A  G  G  L  A  E  G  A  G  A  L  A  P  P  P  P  P        422
1395  ATCAAGGTGGAGCCCATCTCGGAAGGCGAGTCGGAGGAGTAGAGGTGACTGACATCAGTGATGAGGATGAGGAAGACGGGG        1476
423        P  Q  I  K  V  E  P  I  S  E  G  E  S  E  E  V  E  V  T  D  I  S  D  E  D  E  E        449
1477  AGGTGTTCAAGACGCCCGTCCCGTCCCCTAAGCCTGAGCCACCCCGGAGCCATCCCAGTGCATGCC        1558
450        D  G  E  V  F  K  T  P  R  A  P  P  A  P  P  K  P  E  P  G  E  A  P  G  A  S  Q        476
1559  CCTCAAGCTACGCTTTAAGCGCGCTGGAGTGAAGACTGTGCCTCGAAGGGGTGGGGCTTTGAGGAT        1640
477        C  M  P  L  K  L  R  F  K  R  R  W  S  E  D  C  R  L  E  G  G  G  P  A  G  G  F        504
1641  GAGGGTGAGGACAAGAAGGTGCGTGGGAGGGCCTGGGGGAGGCTGGGGGAGGGCCCCTCACCCCGAGGCCGGGTGAGCTCTGACC        1722
505        E  D  E  G  E  D  K  K  V  R  G  E  G  P  G  E  A  G  P  L  T  P  R  R  V  S        531
1723  TCCAGCATGCCACGCCAGCTCTCCCCTGGAGCACCGAGACTCCTGAGGGCTGTGGGCAGGGACCTGTGTGCCCCGCACCC        1804
532        S  D  L  Q  H  A  T  A  Q  L  S  L  E  H  R  D  S  *                              548
1805  CCCATGCTTCTTTTGCTGCTGCCTTAAGCCCCTATGCCCTGGAGGTGAGGCCAGCTCTCTTGTCTCTTCCCTGCCTCCTCCCTT        1886
1887  TTCCCTCCCACATTTTGTATAAAACTTTAATTTCTTTTTTTTTAAAAATGTGGGGTGCCCAGGGCTAGGGGC        1968
1969  TATTCCCTGTCTCTGTGGTTTCTAAGCTTTCTGGGCAAATTGGTGTAGGGGAGGGGAAGTTAAGCTGGGGTCACCTCC        2050
2051  ATTTCTGGGAATTTATATTGAATTGAGGCTTTGGCTTCTCTGCCTCCCACTCCGTCTGCCCCAGCCTCTCGCTTAGGAAGTAAAG        2132
2133  CCTTGTCTCCCCTGTTCTCCCCTGCCCCTGCCCCTGACCGACCCTAGGTTCTATACCCCACAAGGTCACAGCAGGGGAGGGG        2214
2215  GCCCTGCCCTGCCCCTGCCCCTGCCCCCAGGGGGCCATGTGTTGGGGGGCGGAGGAGGGTGAGGGGTGCGCGCCATGGGCCACA        2296
2297  ACAATTTTATAATGAACCAAAATTCATGTGTTGGGGGGTGGAGGAGGGTGAGGGCGAGCACCGGTCCAACCCCTTCATCCCAGCTGTCCTAGG        2378
2379  AATCTCTACAAGTGCCTGCTATCCCTCTCCCACCCAGCACCGGTCCAACCCCTTCATCCCAGCTGTCCTAGG        2460
2461  ACTGGGCCCATGGCCAGGCGGTGGGGGATGGAAGGGGGGTGCCCTGAAACCAAACTGGAAGCCCCTCTGCCTCCCCAGCTG        2542
2543  GGGCCTCTGGGGGTGGGGCTGTCAAGCCTTATTCTGTATTGGGACTGAGGGTGTGGGGGAGTAGAGGGGCCGC        2624
2543  TGGAGAATGTATTCAAAACAATAAACTTTGGACCTTTGGAAAA        2667
```

FIG. 1B-2.

FIG. 9A.
FIG. 9B.
AERF PROTEIN SEQUENCE
1   MKTPADTAIT ITSAFCTRPR GNGSPTSSIS TNWCWDITHS LMWGWLGVQC
51  PRVPRQCRRV VATSASLPQR PPRCCPPPRT PAHHQPALHL HLPSSRLWWP
101 AAWAEAQSVT VVMARQSWRN RWERIPAPDH PALRIWVPSE GPRWPACPMT
151 LVSSESIPGL GVALNPSAPS LCRLWPVLDP CCPLSSPRLC P*

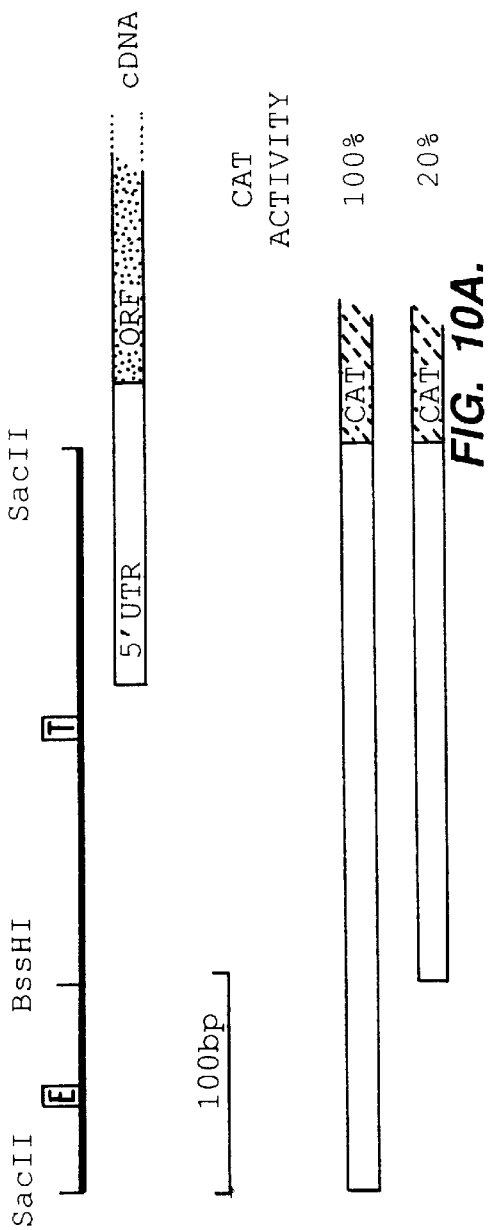

FIG. 10A.

ERF PROMOTER SEQUENCE

```
  1  ccgcgggacc ccatcccacc cccacccccct ccttcctccc tcccccgccg
 51  cgcggcccct ttaagcccag agccggccgg tcctcagtgc tgcgcgccga
101  cgagcgtgtg tgtgagtgcg cggggagggg gcggggcgcag tgtctccatg
151  gcgacgcggc ggtgacgtcg ccggccgggg ggcgtgggcg tcccggcccc
201  ggagtgcgat attaacccgg gAGGCGGGCG CGGGGAGGGG AGAGGCTCTG
251  AGAGGCGAGG CCGGgTGAGG CGGCGAGGGC GGCCCGACGG GCGCGGGACG
301  GGACGGGGCA GCGAGGGCGC CGGGAGCCGC GG
```

FIG. 10B.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 2667 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 123..1769
        ( D ) OTHER INFORMATION: /note= "human ERF (ETS2 Repressor Factor) cDNA"

( x i ) SEQUENCE DESCRIPTION: SEQ ID NO:1:

```
TCTGAGAGGC  GAGGCCGGGT  GAGGCGGCGA  GGGCGGCCCG  ACGGGCGCGG  GACGGGACGG         60

GGCAGCGAGG  GCGCCGGGAG  CCGCGGCCCG  GAATCGGGGC  GCTTCGCCCC  GGGCCCCCCA        120

GC ATG AAG ACC CCG GCG GAC ACA GGG TTT GCC TTC CCG GAT TGG GCC               167
   Met Lys Thr Pro Ala Asp Thr Gly Phe Ala Phe Pro Asp Trp Ala
   1               5                   10                  15

TAC AAG CCA GAG TCG TCC CCT GGC TCA AGG CAG ATC CAG CTG TGG CAC             215
Tyr Lys Pro Glu Ser Ser Pro Gly Ser Arg Gln Ile Gln Leu Trp His
                 20              25                  30

TTT ATC CTG GAG CTG CTG CGG AAG GAG GAG TAC CAG GGC GTC ATT GCC             263
Phe Ile Leu Glu Leu Leu Arg Lys Glu Glu Tyr Gln Gly Val Ile Ala
             35                  40                  45

TGG CAG GGG GAC TAC GGG GAA TTC GTC ATC AAA GAC CCT GAT GAG GTG             311
Trp Gln Gly Asp Tyr Gly Glu Phe Val Ile Lys Asp Pro Asp Glu Val
             50                  55              60

GCC CGG CTG TGG GGC GTT CGC AAG TGC AAG CCC CAG ATG AAT TAC GAC             359
Ala Arg Leu Trp Gly Val Arg Lys Cys Lys Pro Gln Met Asn Tyr Asp
         65                  70              75

AAG CTG AGC CGG GCC CTG CGC TAT TAC TAT AAC AAG CGC ATT CTG CAC             407
Lys Leu Ser Arg Ala Leu Arg Tyr Tyr Tyr Asn Lys Arg Ile Leu His
80                   85                  90                  95

AAG ACC AAG GGG AAA CGG TTC ACC TAC AAG TTC AAT TTC AAC AAA CTG             455
```

| | | | | | | | | | | | | | | | | |
|---|---|---|---|---|---|---|---|---|---|---|---|---|---|---|---|---|
| Lys | Thr | Lys | Gly | Lys | Arg | Phe | Thr | Tyr | Lys | Phe | Asn | Phe | Asn | Lys | Leu | |
| | | | | 100 | | | | 105 | | | | | | 110 | | |

| | | | | | | | | | | | | | | | | |
|---|---|---|---|---|---|---|---|---|---|---|---|---|---|---|---|---|
| GTG | CTG | GTC | AAT | TAC | CCA | TTC | ATT | GAT | GTG | GGG | TTG | GCT | GGG | GGT | GCA | 503 |
| Val | Leu | Val | Asn | Tyr | Pro | Phe | Ile | Asp | Val | Gly | Leu | Ala | Gly | Gly | Ala | |
| | | | 115 | | | | 120 | | | | | 125 | | | | |

| | | | | | | | | | | | | | | | | |
|---|---|---|---|---|---|---|---|---|---|---|---|---|---|---|---|---|
| GTG | CCC | CAG | AGT | GCC | CCG | CCA | GTG | CCG | TCG | GGT | GGT | AGC | CAC | TTC | CGC | 551 |
| Val | Pro | Gln | Ser | Ala | Pro | Pro | Val | Pro | Ser | Gly | Gly | Ser | His | Phe | Arg | |
| | | 130 | | | | | 135 | | | | | 140 | | | | |

| | | | | | | | | | | | | | | | | |
|---|---|---|---|---|---|---|---|---|---|---|---|---|---|---|---|---|
| TTC | CCT | CCC | TCA | ACG | CCC | TCC | GAG | GTG | CTG | TCC | CCC | ACC | GAG | GAC | CCC | 599 |
| Phe | Pro | Pro | Ser | Thr | Pro | Ser | Glu | Val | Leu | Ser | Pro | Thr | Glu | Asp | Pro | |
| 145 | | | | | | 150 | | | | | 155 | | | | | |

| | | | | | | | | | | | | | | | | |
|---|---|---|---|---|---|---|---|---|---|---|---|---|---|---|---|---|
| CGC | TCA | CCA | CCA | GCC | TGC | TCT | TCA | TCT | TCA | TCT | TCC | CTC | TTC | TCG | GCT | 647 |
| Arg | Ser | Pro | Pro | Ala | Cys | Ser | Ser | Ser | Ser | Ser | Ser | Leu | Phe | Ser | Ala | |
| 160 | | | | | 165 | | | | | 170 | | | | | 175 | |

| | | | | | | | | | | | | | | | | |
|---|---|---|---|---|---|---|---|---|---|---|---|---|---|---|---|---|
| GTG | GTG | GCC | CGC | CGC | CTG | GGC | CGA | GGC | TCA | GTC | AGT | GAC | TGT | AGT | GAT | 695 |
| Val | Val | Ala | Arg | Arg | Leu | Gly | Arg | Gly | Ser | Val | Ser | Asp | Cys | Ser | Asp | |
| | | | | 180 | | | | 185 | | | | | 190 | | | |

| | | | | | | | | | | | | | | | | |
|---|---|---|---|---|---|---|---|---|---|---|---|---|---|---|---|---|
| GGC | ACG | TCA | GAG | CTG | GAG | GAA | CCG | CTG | GGA | GAG | GAT | CCC | CGC | GCC | CGA | 743 |
| Gly | Thr | Ser | Glu | Leu | Glu | Glu | Pro | Leu | Gly | Glu | Asp | Pro | Arg | Ala | Arg | |
| | | | 195 | | | | 200 | | | | | 205 | | | | |

| | | | | | | | | | | | | | | | | |
|---|---|---|---|---|---|---|---|---|---|---|---|---|---|---|---|---|
| CCA | CCC | GGC | CCT | CCG | GAT | CTG | GGT | GCC | TTC | CGA | GGG | CCC | CCG | CTG | GCC | 791 |
| Pro | Pro | Gly | Pro | Pro | Asp | Leu | Gly | Ala | Phe | Arg | Gly | Pro | Pro | Leu | Ala | |
| | | 210 | | | | | 215 | | | | | 220 | | | | |

| | | | | | | | | | | | | | | | | |
|---|---|---|---|---|---|---|---|---|---|---|---|---|---|---|---|---|
| CGC | CTG | CCC | CAT | GAC | CCT | GGT | GTC | TTC | CGA | GTC | TAT | CCC | CGG | CCT | CGG | 839 |
| Arg | Leu | Pro | His | Asp | Pro | Gly | Val | Phe | Arg | Val | Tyr | Pro | Arg | Pro | Arg | |
| | 225 | | | | | 230 | | | | | 235 | | | | | |

| | | | | | | | | | | | | | | | | |
|---|---|---|---|---|---|---|---|---|---|---|---|---|---|---|---|---|
| GGT | GGC | CCT | GAA | CCC | CTC | AGC | CCC | TTC | CCT | GTG | TCG | CCT | CTG | GCC | GGT | 887 |
| Gly | Gly | Pro | Glu | Pro | Leu | Ser | Pro | Phe | Pro | Val | Ser | Pro | Leu | Ala | Gly | |
| 240 | | | | | 245 | | | | | 250 | | | | | 255 | |

| | | | | | | | | | | | | | | | | |
|---|---|---|---|---|---|---|---|---|---|---|---|---|---|---|---|---|
| CCT | GGA | TCC | CTG | CTG | CCC | CCT | CAG | CTC | TCC | CCG | GCT | CTG | CCC | ATG | ACG | 935 |
| Pro | Gly | Ser | Leu | Leu | Pro | Pro | Gln | Leu | Ser | Pro | Ala | Leu | Pro | Met | Thr | |
| | | | | 260 | | | | | 265 | | | | | 270 | | |

| | | | | | | | | | | | | | | | | |
|---|---|---|---|---|---|---|---|---|---|---|---|---|---|---|---|---|
| CCC | ACC | CAC | CTG | GCC | TAC | ACT | CCC | TCG | CCC | ACG | CTG | AGC | CCG | ATG | TAC | 983 |
| Pro | Thr | His | Leu | Ala | Tyr | Thr | Pro | Ser | Pro | Thr | Leu | Ser | Pro | Met | Tyr | |
| | | 275 | | | | | 280 | | | | | 285 | | | | |

| | | | | | | | | | | | | | | | | |
|---|---|---|---|---|---|---|---|---|---|---|---|---|---|---|---|---|
| CCC | AGT | GGT | GGC | GGG | GGG | CCC | AGC | GGC | TCA | GGG | GGA | GGC | TCC | CAC | TTC | 1031 |
| Pro | Ser | Gly | Gly | Gly | Gly | Pro | Ser | Gly | Ser | Gly | Gly | Gly | Ser | His | Phe | |
| | | 290 | | | | | 295 | | | | | 300 | | | | |

| | | | | | | | | | | | | | | | | |
|---|---|---|---|---|---|---|---|---|---|---|---|---|---|---|---|---|
| TCC | TTC | AGC | CCT | GAG | GAC | ATG | AAA | CGG | TAC | CTG | CAG | GCC | CAC | ACC | CAA | 1079 |
| Ser | Phe | Ser | Pro | Glu | Asp | Met | Lys | Arg | Tyr | Leu | Gln | Ala | His | Thr | Gln | |
| 305 | | | | | 310 | | | | | 315 | | | | | | |

| | | | | | | | | | | | | | | | | |
|---|---|---|---|---|---|---|---|---|---|---|---|---|---|---|---|---|
| AGC | GTC | TAC | AAC | TAC | CAC | CTC | AGC | CCC | CGC | GCC | TTC | CTG | CAC | TAC | CCT | 1127 |
| Ser | Val | Tyr | Asn | Tyr | His | Leu | Ser | Pro | Arg | Ala | Phe | Leu | His | Tyr | Pro | |
| 320 | | | | | 325 | | | | | 330 | | | | | 335 | |

| | | | | | | | | | | | | | | | | |
|---|---|---|---|---|---|---|---|---|---|---|---|---|---|---|---|---|
| GGG | CTG | GTG | GTG | CCC | CAG | CCC | CAG | CGC | CCT | GAC | AAG | TGC | CCG | CTG | CCG | 1175 |
| Gly | Leu | Val | Val | Pro | Gln | Pro | Gln | Arg | Pro | Asp | Lys | Cys | Pro | Leu | Pro | |
| | | | | 340 | | | | 345 | | | | | 350 | | | |

| | | | | | | | | | | | | | | | | |
|---|---|---|---|---|---|---|---|---|---|---|---|---|---|---|---|---|
| CCC | ATG | GCA | CCC | GAG | ACC | CCA | CCG | GTC | CCC | TCC | TCG | GCC | TCG | TCA | TCC | 1223 |
| Pro | Met | Ala | Pro | Glu | Thr | Pro | Pro | Val | Pro | Ser | Ser | Ala | Ser | Ser | Ser | |
| | | | 355 | | | | | 360 | | | | | 365 | | | |

| | | | | | | | | | | | | | | | | |
|---|---|---|---|---|---|---|---|---|---|---|---|---|---|---|---|---|
| TCT | TCT | TCT | TCT | TCC | TCC | CCA | TTC | AAG | TTT | AAG | CTC | CAG | CGG | CCC | CCA | 1271 |
| Ser | Ser | Ser | Ser | Ser | Ser | Pro | Phe | Lys | Phe | Lys | Leu | Gln | Arg | Pro | Pro | |
| | | 370 | | | | | 375 | | | | | 380 | | | | |

| | | | | | | | | | | | | | | | | |
|---|---|---|---|---|---|---|---|---|---|---|---|---|---|---|---|---|
| CTC | GGA | CGC | CGG | CAG | CGG | GCA | GCT | GGG | GAG | AAG | GCC | GTA | GCC | GCT | GCT | 1319 |
| Leu | Gly | Arg | Arg | Gln | Arg | Ala | Ala | Gly | Glu | Lys | Ala | Val | Ala | Ala | Ala | |
| | 385 | | | | | 390 | | | | | 395 | | | | | |

| | | | | | | | | | | | | | | | | |
|---|---|---|---|---|---|---|---|---|---|---|---|---|---|---|---|---|
| GAC | AAG | AGC | GGT | GGC | AGT | GCA | GGC | GGG | CTG | GCT | GAG | GGG | GCA | GGG | GCG | 1367 |
| Asp | Lys | Ser | Gly | Gly | Ser | Ala | Gly | Gly | Leu | Ala | Glu | Gly | Ala | Gly | Ala | |
| 400 | | | | | 405 | | | | | 410 | | | | | 415 | |

| | | | | | | | | | | | | | | | | |
|---|---|---|---|---|---|---|---|---|---|---|---|---|---|---|---|---|
| CTA | GCC | CCA | CCG | CCC | CCG | CCA | CCA | CAG | ATC | AAG | GTG | GAG | CCC | ATC | TCG | 1415 |

```
Leu  Ala  Pro  Pro  Pro  Pro  Pro  Pro  Gln  Ile  Lys  Val  Glu  Pro  Ile  Ser
               420                      425                      430

GAA  GGC  GAG  TCG  GAG  GAG  GTA  GAG  GTG  ACT  GAC  ATC  AGT  GAT  GAG  GAT   1463
Glu  Gly  Glu  Ser  Glu  Glu  Val  Glu  Val  Thr  Asp  Ile  Ser  Asp  Glu  Asp
               435                      440                      445

GAG  GAA  GAC  GGG  GAG  GTG  TTC  AAG  ACG  CCC  CGT  GCC  CCA  CCT  GCA  CCC   1511
Glu  Glu  Asp  Gly  Glu  Val  Phe  Lys  Thr  Pro  Arg  Ala  Pro  Pro  Ala  Pro
               450                      455                      460

CCT  AAG  CCT  GAG  CCC  GGC  GAG  GCA  CCC  GGG  GCA  TCC  CAG  TGC  ATG  CCC   1559
Pro  Lys  Pro  Glu  Pro  Gly  Glu  Ala  Pro  Gly  Ala  Ser  Gln  Cys  Met  Pro
     465                      470                      475

CTC  AAG  CTA  CGC  TTT  AAG  CGG  CGC  TGG  AGT  GAA  GAC  TGT  CGC  CTC  GAA   1607
Leu  Lys  Leu  Arg  Phe  Lys  Arg  Arg  Trp  Ser  Glu  Asp  Cys  Arg  Leu  Glu
480            485                      490                      495

GGG  GGT  GGG  GGC  CCC  GCT  GGG  GGC  TTT  GAG  GAT  GAG  GGT  GAG  GAC  AAG   1655
Gly  Gly  Gly  Gly  Pro  Ala  Gly  Gly  Phe  Glu  Asp  Glu  Gly  Glu  Asp  Lys
               500                      505                      510

AAG  GTG  CGT  GGG  GAG  GGG  CCT  GGG  GAG  GCT  GGG  GGG  CCC  CTC  ACC  CCA   1703
Lys  Val  Arg  Gly  Glu  Gly  Pro  Gly  Glu  Ala  Gly  Gly  Pro  Leu  Thr  Pro
               515                      520                      525

AGG  CGG  GTG  AGC  TCT  GAC  CTC  CAG  CAT  GCC  ACG  GCC  CAG  CTC  TCC  CTG   1751
Arg  Arg  Val  Ser  Ser  Asp  Leu  Gln  His  Ala  Thr  Ala  Gln  Leu  Ser  Leu
               530                      535                      540

GAG  CAC  CGA  GAC  TCC  TGAGGGCTGT  GGGCAGGGGA  CCTGTGTGCC  CCGCACCCCC          1806
Glu  His  Arg  Asp  Ser
     545

CATGCTTCTT  TTGCTGCCTT  AAGCCCCCTA  TGCCCTGGAG  GTGAGGGCAG  CTCTCTTGTC          1866
TCTTCCCTGC  CTCCTCCCTT  TTCCCTCCCC  ACATTTTGTA  TAAAACTTTA  ATTTCTTTTT          1926
TTTAAAAATG  GTGGGGGTGG  GTGGGTGCCC  AGGGCTAGGG  GCTATTCCCT  GTCTCTGTGG          1986
GTTTCTAAGC  TCTGGGCAAA  TTGGTGGTAG  GGGGAGGGAG  GGGGAAGTTA  AGGGGGTCAC          2046
CTCCATTCTG  GGGAATTTAT  ATTTGAATTG  AGGCTTTGGC  CTTAACACCC  AGGAACTTTT          2106
CTATTACAAT  CGCTTAGGAA  GTAAAGCCTT  GTCTCCCTCC  CTGTTCTCTG  CCTCTTGTAC          2166
CCCTCTGACC  CACCCGCTCT  GCCCCACTCC  CAGCCCTCCT  CAGCCCCAGC  CCTGCCTGCC          2226
CTGCCCCTCC  AGGGGGCCAT  GAGTGCCTAG  GTTTCTCATA  CCCCACAAGG  TCACAGCAGG          2286
GGAGGGAGGG  ACAATTTTAT  AATGAACCAA  AAATTCCATG  TGTTGGGGGG  TGGGGGGCGG          2346
AGGAGGGTGA  GGGGTGCCGC  CCATGGGCCA  CAAATCTCTA  CAAGTGCCTG  CTATCCCTCT          2406
CCCACTCCCC  ACCCAGCAC   CGGTCCAACC  CCTTCATCCC  CAGCTGCTCC  TAGGACTGGC          2466
CCATGGGCAG  GCGGGTGGGG  GGATGGGAAG  GGGGTGCCCT  GAAACCAAAC  TGGAAGCCCC          2526
CTCTGCCTCC  CAGCTGGGGC  CTCTGGGGTG  GGGTGGGGGG  CTGTGGTCAA  GCCTTATTCT          2586
GTATTGGGGA  CTGAGGGTGG  GGGGAGTAGA  GGGGCCGCTG  GAGAATGTAT  TCAAAACAAT          2646
AAACTTTGGA  CCTTTGGAAA  A                                                       2667
```

( 2 ) INFORMATION FOR SEQ ID NO:2:

( i ) SEQUENCE CHARACTERISTICS:
            ( A ) LENGTH: 548 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

```
Met  Lys  Thr  Pro  Ala  Asp  Thr  Gly  Phe  Ala  Phe  Pro  Asp  Trp  Ala  Tyr
  1            5                      10                      15
```

| Lys | Pro | Glu | Ser | Ser | Pro | Gly | Ser | Arg | Gln | Ile | Gln | Leu | Trp | His | Phe |
|---|---|---|---|---|---|---|---|---|---|---|---|---|---|---|---|
| | | | 20 | | | | 25 | | | | | | 30 | | |

| Ile | Leu | Glu | Leu | Leu | Arg | Lys | Glu | Tyr | Gln | Gly | Val | Ile | Ala | Trp |
|---|---|---|---|---|---|---|---|---|---|---|---|---|---|---|
| | | 35 | | | | 40 | | | | | 45 | | | |

| Gln | Gly | Asp | Tyr | Gly | Glu | Phe | Val | Ile | Lys | Asp | Pro | Asp | Glu | Val | Ala |
|---|---|---|---|---|---|---|---|---|---|---|---|---|---|---|---|
| | 50 | | | | | 55 | | | | | | 60 | | | |

| Arg | Leu | Trp | Gly | Val | Arg | Lys | Cys | Lys | Pro | Gln | Met | Asn | Tyr | Asp | Lys |
|---|---|---|---|---|---|---|---|---|---|---|---|---|---|---|---|
| 65 | | | | | 70 | | | | | 75 | | | | | 80 |

| Leu | Ser | Arg | Ala | Leu | Arg | Tyr | Tyr | Tyr | Asn | Lys | Arg | Ile | Leu | His | Lys |
|---|---|---|---|---|---|---|---|---|---|---|---|---|---|---|---|
| | | | | 85 | | | | | 90 | | | | | 95 | |

| Thr | Lys | Gly | Lys | Arg | Phe | Thr | Tyr | Lys | Phe | Asn | Phe | Asn | Lys | Leu | Val |
|---|---|---|---|---|---|---|---|---|---|---|---|---|---|---|---|
| | | | | 100 | | | | 105 | | | | | 110 | | |

| Leu | Val | Asn | Tyr | Pro | Phe | Ile | Asp | Val | Gly | Leu | Ala | Gly | Gly | Ala | Val |
|---|---|---|---|---|---|---|---|---|---|---|---|---|---|---|---|
| | | | 115 | | | | 120 | | | | | 125 | | | |

| Pro | Gln | Ser | Ala | Pro | Pro | Val | Pro | Ser | Gly | Gly | Ser | His | Phe | Arg | Phe |
|---|---|---|---|---|---|---|---|---|---|---|---|---|---|---|---|
| | | 130 | | | | | 135 | | | | | 140 | | | |

| Pro | Pro | Ser | Thr | Pro | Ser | Glu | Val | Leu | Ser | Pro | Thr | Glu | Asp | Pro | Arg |
|---|---|---|---|---|---|---|---|---|---|---|---|---|---|---|---|
| 145 | | | | | 150 | | | | | 155 | | | | | 160 |

| Ser | Pro | Pro | Ala | Cys | Ser | Ser | Ser | Ser | Ser | Leu | Phe | Ser | Ala | Val |
|---|---|---|---|---|---|---|---|---|---|---|---|---|---|---|
| | | | | 165 | | | | | 170 | | | | 175 | |

| Val | Ala | Arg | Arg | Leu | Gly | Arg | Gly | Ser | Val | Ser | Asp | Cys | Ser | Asp | Gly |
|---|---|---|---|---|---|---|---|---|---|---|---|---|---|---|---|
| | | | 180 | | | | | 185 | | | | | 190 | | |

| Thr | Ser | Glu | Leu | Glu | Glu | Pro | Leu | Gly | Glu | Asp | Pro | Arg | Ala | Arg | Pro |
|---|---|---|---|---|---|---|---|---|---|---|---|---|---|---|---|
| | | 195 | | | | | 200 | | | | | 205 | | | |

| Pro | Gly | Pro | Pro | Asp | Leu | Gly | Ala | Phe | Arg | Gly | Pro | Pro | Leu | Ala | Arg |
|---|---|---|---|---|---|---|---|---|---|---|---|---|---|---|---|
| | 210 | | | | | 215 | | | | | 220 | | | | |

| Leu | Pro | His | Asp | Pro | Gly | Val | Phe | Arg | Val | Tyr | Pro | Arg | Pro | Arg | Gly |
|---|---|---|---|---|---|---|---|---|---|---|---|---|---|---|---|
| 225 | | | | | 230 | | | | | 235 | | | | | 240 |

| Gly | Pro | Glu | Pro | Leu | Ser | Pro | Phe | Pro | Val | Ser | Pro | Leu | Ala | Gly | Pro |
|---|---|---|---|---|---|---|---|---|---|---|---|---|---|---|---|
| | | | | 245 | | | | | 250 | | | | | 255 | |

| Gly | Ser | Leu | Leu | Pro | Pro | Gln | Leu | Ser | Pro | Ala | Leu | Pro | Met | Thr | Pro |
|---|---|---|---|---|---|---|---|---|---|---|---|---|---|---|---|
| | | | 260 | | | | | 265 | | | | | 270 | | |

| Thr | His | Leu | Ala | Tyr | Thr | Pro | Ser | Pro | Thr | Leu | Ser | Pro | Met | Tyr | Pro |
|---|---|---|---|---|---|---|---|---|---|---|---|---|---|---|---|
| | | 275 | | | | | 280 | | | | | 285 | | | |

| Ser | Gly | Gly | Gly | Gly | Pro | Ser | Gly | Ser | Gly | Gly | Ser | His | Phe | Ser |
|---|---|---|---|---|---|---|---|---|---|---|---|---|---|---|
| | 290 | | | | | 295 | | | | | 300 | | | |

| Phe | Ser | Pro | Glu | Asp | Met | Lys | Arg | Tyr | Leu | Gln | Ala | His | Thr | Gln | Ser |
|---|---|---|---|---|---|---|---|---|---|---|---|---|---|---|---|
| 305 | | | | | 310 | | | | | 315 | | | | | 320 |

| Val | Tyr | Asn | Tyr | His | Leu | Ser | Pro | Arg | Ala | Phe | Leu | His | Tyr | Pro | Gly |
|---|---|---|---|---|---|---|---|---|---|---|---|---|---|---|---|
| | | | | 325 | | | | | 330 | | | | | 335 | |

| Leu | Val | Val | Pro | Gln | Pro | Gln | Arg | Pro | Asp | Lys | Cys | Pro | Leu | Pro | Pro |
|---|---|---|---|---|---|---|---|---|---|---|---|---|---|---|---|
| | | | 340 | | | | | 345 | | | | | 350 | | |

| Met | Ala | Pro | Glu | Thr | Pro | Pro | Val | Pro | Ser | Ser | Ala | Ser | Ser | Ser | Ser |
|---|---|---|---|---|---|---|---|---|---|---|---|---|---|---|---|
| | | 355 | | | | | 360 | | | | | 365 | | | |

| Ser | Ser | Ser | Ser | Ser | Pro | Phe | Lys | Phe | Lys | Leu | Gln | Arg | Pro | Pro | Leu |
|---|---|---|---|---|---|---|---|---|---|---|---|---|---|---|---|
| | 370 | | | | | 375 | | | | | 380 | | | | |

| Gly | Arg | Arg | Gln | Arg | Ala | Ala | Gly | Glu | Lys | Ala | Val | Ala | Ala | Ala | Asp |
|---|---|---|---|---|---|---|---|---|---|---|---|---|---|---|---|
| 385 | | | | | 390 | | | | | 395 | | | | | 400 |

| Lys | Ser | Gly | Gly | Ser | Ala | Gly | Gly | Leu | Ala | Glu | Gly | Ala | Gly | Ala | Leu |
|---|---|---|---|---|---|---|---|---|---|---|---|---|---|---|---|
| | | | | 405 | | | | | 410 | | | | | 415 | |

| Ala | Pro | Pro | Pro | Pro | Pro | Pro | Gln | Ile | Lys | Val | Glu | Pro | Ile | Ser | Glu |
|---|---|---|---|---|---|---|---|---|---|---|---|---|---|---|---|
| | | | 420 | | | | | 425 | | | | | 430 | | |

| Gly | Glu | Ser | Glu | Glu | Val | Glu | Val | Thr | Asp | Ile | Ser | Asp | Glu | Asp | Glu |
|---|---|---|---|---|---|---|---|---|---|---|---|---|---|---|---|
| | | 435 | | | | | 440 | | | | | 445 | | | |

```
Glu  Asp  Gly  Glu  Val  Phe  Lys  Thr  Pro  Arg  Ala  Pro  Pro  Ala  Pro  Pro
     450                      455                 460

Lys  Pro  Glu  Pro  Gly  Glu  Ala  Pro  Gly  Ala  Ser  Gln  Cys  Met  Pro  Leu
465                      470                 475                           480

Lys  Leu  Arg  Phe  Lys  Arg  Arg  Trp  Ser  Glu  Asp  Cys  Arg  Leu  Glu  Gly
               485                      490                           495

Gly  Gly  Gly  Pro  Ala  Gly  Gly  Phe  Glu  Asp  Glu  Gly  Glu  Asp  Lys  Lys
               500                      505                           510

Val  Arg  Gly  Glu  Gly  Pro  Gly  Glu  Ala  Gly  Gly  Pro  Leu  Thr  Pro  Arg
          515                 520                      525

Arg  Val  Ser  Ser  Asp  Leu  Gln  His  Ala  Thr  Ala  Gln  Leu  Ser  Leu  Glu
          530                 535                 540

His  Arg  Asp  Ser
545
```

( 2 ) INFORMATION FOR SEQ ID NO:3:

( i ) SEQUENCE CHARACTERISTICS:
        ( A ) LENGTH: 2432 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 123..698
        ( D ) OTHER INFORMATION: /note= "human alternatively spliced ERF
                ( A E R F ) cDNA"

( x i ) SEQUENCE DESCRIPTION: SEQ ID NO:3:

```
TCTGAGAGGC  GAGGCCGGGT  GAGGCGGCGA  GGGCGGCCCG  ACGGGCGCGG  GACGGGACGG       60

GGCAGCGAGG  GCGCCGGGAG  CCGCGGCCCG  GAATCGGGGC  GCTTCGCCCC  GGGCCCCCCA      120

GC  ATG  AAG  ACC  CCG  GCG  GAC  ACA  GCT  ATT  ACT  ATA  ACA  AGC  GCA  TTC      167
    Met  Lys  Thr  Pro  Ala  Asp  Thr  Ala  Ile  Thr  Ile  Thr  Ser  Ala  Phe
     1                 5                      10                       15

TGC  ACA  AGA  CCA  AGG  GGA  AAC  GGT  TCA  CCT  ACA  AGT  TCA  ATT  TCA  ACA      215
Cys  Thr  Arg  Pro  Arg  Gly  Asn  Gly  Ser  Pro  Thr  Ser  Ser  Ile  Ser  Thr
                20                      25                           30

AAC  TGG  TGC  TGG  TCA  ATT  ACC  CAT  TCA  TTG  ATG  TGG  GGT  TGG  CTG  GGG      263
Asn  Trp  Cys  Trp  Ser  Ile  Thr  His  Ser  Leu  Met  Trp  Gly  Trp  Leu  Gly
               35                      40                           45

GTG  CAG  TGC  CCC  AGA  GTG  CCC  CGC  CAG  TGC  CGT  CGG  GTG  GTA  GCC  ACT      311
Val  Gln  Cys  Pro  Arg  Val  Pro  Arg  Gln  Cys  Arg  Arg  Val  Val  Ala  Thr
          50                      55                           60

TCC  GCT  TCC  CTC  CCT  CAA  CGC  CCT  CCG  AGG  TGC  TGT  CCC  CCA  CCG  AGG      359
Ser  Ala  Ser  Leu  Pro  Gln  Arg  Pro  Pro  Arg  Cys  Cys  Pro  Pro  Pro  Arg
     65                      70                      75

ACC  CCC  GCT  CAC  CAC  CAG  CCT  GCT  CTT  CAT  CTT  CAT  CTT  CCC  TCT  TCT      407
Thr  Pro  Ala  His  His  Gln  Pro  Ala  Leu  His  Leu  His  Leu  Pro  Ser  Ser
 80                      85                      90                       95

CGG  CTG  TGG  TGG  CCC  GCC  GCC  TGG  GCC  GAG  GCT  CAG  TCA  GTG  ACT  GTA      455
Arg  Leu  Trp  Trp  Pro  Ala  Ala  Trp  Ala  Glu  Ala  Gln  Ser  Val  Thr  Val
                    100                      105                      110

GTG  ATG  GCA  CGT  CAG  AGC  TGG  AGG  AAC  CGC  TGG  GAG  AGG  ATC  CCC  GCG      503
Val  Met  Ala  Arg  Gln  Ser  Trp  Arg  Asn  Arg  Trp  Glu  Arg  Ile  Pro  Ala
               115                      120                      125

CCC  GAC  CAC  CCG  GCC  CTC  CGG  ATC  TGG  GTG  CCT  TCC  GAG  GGC  CCC  CGC      551
Pro  Asp  His  Pro  Ala  Leu  Arg  Ile  Trp  Val  Pro  Ser  Glu  Gly  Pro  Arg
               130                      135                      140
```

| | | | | | | | | | | | | | | | | |
|---|---|---|---|---|---|---|---|---|---|---|---|---|---|---|---|---|
| TGG | CCC | GCC | TGC | CCC | ATG | ACC | CTG | GTG | TCT | TCC | GAG | TCT | ATC | CCC | GGC | 599 |
| Trp | Pro | Ala | Cys | Pro | Met | Thr | Leu | Val | Ser | Ser | Glu | Ser | Ile | Pro | Gly | |
| 145 | | | | | 150 | | | | | | 155 | | | | | |
| CTC | GGG | GTG | GCC | CTG | AAC | CCC | TCA | GCC | CCT | TCC | CTG | TGT | CGC | CTC | TGG | 647 |
| Leu | Gly | Val | Ala | Leu | Asn | Pro | Ser | Ala | Pro | Ser | Leu | Cys | Arg | Leu | Trp | |
| 160 | | | | | 165 | | | | | 170 | | | | | 175 | |
| CCG | GTC | CTG | GAT | CCC | TGC | TGC | CCC | CTC | AGC | TCT | CCC | CGG | CTC | TGC | CCA | 695 |
| Pro | Val | Leu | Asp | Pro | Cys | Cys | Pro | Leu | Ser | Ser | Pro | Arg | Leu | Cys | Pro | |
| | | | 180 | | | | | | 185 | | | | | 190 | | |

```
TGACGCCCAC CCACCTGGCC TACACTCCCT CGCCCACGCT GAGCCCGATG TACCCCAGTG    755
GTGGCGGGGG GCCCAGCGGC TCAGGGGAG GCTCCCACTT CTCCTTCAGC CCTGAGGACA    815
TGAAACGGTA CCTGCAGGCC CACACCCAAA GCGTCTACAA CTACCACCTC AGCCCCCGCG    875
CCTTCCTGCA CTACCCTGGG CTGGTGGTGC CCCAGCCCCA GCGCCCTGAC AAGTGCCCGC    935
TGCCGCCCAT GGCACCCGAG ACCCCACCGG TCCCCTCCTC GGCCTCGTCA TCCTCTTCTT    995
CTTCTTCCTC CCCATTCAAG TTTAAGCTCC AGCGGCCCCC ACTCGGACGC CGGCAGCGGG   1055
CAGCTGGGGA GAAGGCCGTA GCCGCTGCTG ACAAGAGCGG TGGCAGTGCA GGCGGGCTGG   1115
CTGAGGGGGC AGGGGCGCTA GCCCCACCGC CCCCGCCACC ACAGATCAAG GTGGAGCCCA   1175
TCTCGGAAGG CGAGTCGGAG GAGGTAGAGG TGACTGACAT CAGTGATGAG GATGAGGAAG   1235
ACGGGGAGGT GTTCAAGACG CCCCGTGCCC CACCTGCACC CCCTAAGCCT GAGCCCGGCG   1295
AGGCACCCGG GGCATCCCAG TGCATGCCCC TCAAGCTACG CTTTAAGCGG CGCTGGAGTG   1355
AAGACTGTCG CCTCGAAGGG GGTGGGGGCC CCGCTGGGGG CTTTGAGGAT GAGGGTGAGG   1415
ACAAGAAGGT GCGTGGGGAG GGGCCTGGGG AGGCTGGGGG GCCCCTCACC CCAAGGCGGG   1475
TGAGCTCTGA CCTCCAGCAT GCCACGGCCC AGCTCTCCCT GGAGCACCGA GACTCCTGAG   1535
GGCTGTGGGC AGGGGACCTG TGTGCCCCGC ACCCCCATG CTTCTTTTGC TGCCTTAAGC   1595
CCCCTATGCC CTGGAGGTGA GGGCAGCTCT CTTGTCTCTT CCCTGCCTCC TCCCTTTTCC   1655
CTCCCCACAT TTTGTATAAA ACTTTAATTT CTTTTTTTA AAAATGGTGG GGGTGGGTGG   1715
GTGCCCAGGG CTAGGGGCTA TTCCCTGTCT CTGTGGGTTT CTAAGCTCTG GGCAAATTGG   1775
TGGTAGGGGG AGGGAGGGGG AAGTTAAGGG GGTCACCTCC ATTCTGGGGA ATTTATATTT   1835
GAATTGAGGC TTTGGCCTTA ACACCCAGGA ACTTTCTAT TACAATCGCT TAGGAAGTAA   1895
AGCCTTGTCT CCCTCCCTGT TCTCTGCCTC TTGTACCCCT CTGACCCACC CGCTCTGCCC   1955
CACTCCCAGC CCTCCTCAGC CCCAGCCCTG CCTGCCCTGC CCCTCCAGGG GGCCATGAGT   2015
GCCTAGGTTT CTCATACCCC ACAAGGTCAC AGCAGGGGAG GGAGGGACAA TTTTATAATG   2075
AACCAAAAAT TCCATGTGTT GGGGGGTGGG GGGCGGAGGA GGGTGAGGGG TGCCGCCCAT   2135
GGGCCACAAA TCTCTACAAG TGCCTGCTAT CCCTCTCCCA CTCCCCACCC CAGCACCGGT   2195
CCAACCCCTT CATCCCAGC TGCTCCTAGG ACTGGCCCAT GGGCAGGCGG GTGGGGGAT    2255
GGGAAGGGGG TGCCCTGAAA CCAAACTGGA AGCCCCTCT GCCTCCCAGC TGGGGCCTCT   2315
GGGGTGGGGT GGGGGGCTGT GGTCAAGCCT TATTCTGTAT TGGGGACTGA GGGTGGGGGG   2375
AGTAGAGGGG CCGCTGGAGA ATGTATTCAA AACAATAAAC TTTGGACCTT TGGAAAA     2432
```

( 2 ) INFORMATION FOR SEQ ID NO:4:

( i ) SEQUENCE CHARACTERISTICS:
        ( A ) LENGTH: 191 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Lys | Thr | Pro | Ala | Asp | Thr | Ala | Ile | Thr | Ile | Thr | Ser | Ala | Phe | Cys |
|---|---|---|---|---|---|---|---|---|---|---|---|---|---|---|---|
| 1 | | | | 5 | | | | | 10 | | | | | 15 | |

| Thr | Arg | Pro | Arg | Gly | Asn | Gly | Ser | Pro | Thr | Ser | Ser | Ile | Ser | Thr | Asn |
|---|---|---|---|---|---|---|---|---|---|---|---|---|---|---|---|
| | | | 20 | | | | | 25 | | | | | 30 | | |

| Trp | Cys | Trp | Ser | Ile | Thr | His | Ser | Leu | Met | Trp | Gly | Trp | Leu | Gly | Val |
|---|---|---|---|---|---|---|---|---|---|---|---|---|---|---|---|
| | | 35 | | | | | 40 | | | | | 45 | | | |

| Gln | Cys | Pro | Arg | Val | Pro | Arg | Gln | Cys | Arg | Arg | Val | Val | Ala | Thr | Ser |
|---|---|---|---|---|---|---|---|---|---|---|---|---|---|---|---|
| | 50 | | | | | 55 | | | | | 60 | | | | |

| Ala | Ser | Leu | Pro | Gln | Arg | Pro | Pro | Arg | Cys | Cys | Pro | Pro | Pro | Arg | Thr |
|---|---|---|---|---|---|---|---|---|---|---|---|---|---|---|---|
| 65 | | | | | 70 | | | | 75 | | | | | | 80 |

| Pro | Ala | His | His | Gln | Pro | Ala | Leu | His | Leu | His | Leu | Pro | Ser | Ser | Arg |
|---|---|---|---|---|---|---|---|---|---|---|---|---|---|---|---|
| | | | | 85 | | | | | 90 | | | | | 95 | |

| Leu | Trp | Trp | Pro | Ala | Ala | Trp | Ala | Glu | Ala | Gln | Ser | Val | Thr | Val | Val |
|---|---|---|---|---|---|---|---|---|---|---|---|---|---|---|---|
| | | | 100 | | | | | 105 | | | | | 110 | | |

| Met | Ala | Arg | Gln | Ser | Trp | Arg | Asn | Arg | Trp | Glu | Arg | Ile | Pro | Ala | Pro |
|---|---|---|---|---|---|---|---|---|---|---|---|---|---|---|---|
| | | | 115 | | | | | 120 | | | | | 125 | | |

| Asp | His | Pro | Ala | Leu | Arg | Ile | Trp | Val | Pro | Ser | Glu | Gly | Pro | Arg | Trp |
|---|---|---|---|---|---|---|---|---|---|---|---|---|---|---|---|
| | 130 | | | | | 135 | | | | | 140 | | | | |

| Pro | Ala | Cys | Pro | Met | Thr | Leu | Val | Ser | Ser | Glu | Ser | Ile | Pro | Gly | Leu |
|---|---|---|---|---|---|---|---|---|---|---|---|---|---|---|---|
| 145 | | | | | 150 | | | | | 155 | | | | | 160 |

| Gly | Val | Ala | Leu | Asn | Pro | Ser | Ala | Pro | Ser | Leu | Cys | Arg | Leu | Trp | Pro |
|---|---|---|---|---|---|---|---|---|---|---|---|---|---|---|---|
| | | | | 165 | | | | | 170 | | | | | 175 | |

| Val | Leu | Asp | Pro | Cys | Cys | Pro | Leu | Ser | Ser | Pro | Arg | Leu | Cys | Pro | |
|---|---|---|---|---|---|---|---|---|---|---|---|---|---|---|---|
| | | | 180 | | | | | 185 | | | | | 190 | | |

( 2 ) INFORMATION FOR SEQ ID NO:5:

( i ) SEQUENCE CHARACTERISTICS:
        ( A ) LENGTH: 59 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Domain
        ( B ) LOCATION: 1..59
        ( D ) OTHER INFORMATION: /note= "human ERF repressor domain
        ( E R F   a m i n o   a c i d   p o s i t i o n s   4 7 2 - 5 3 0 )"

( x i ) SEQUENCE DESCRIPTION: SEQ ID NO:5:

| Pro | Gly | Ala | Ser | Gln | Cys | Met | Pro | Leu | Lys | Leu | Arg | Phe | Lys | Arg | Arg |
|---|---|---|---|---|---|---|---|---|---|---|---|---|---|---|---|
| 1 | | | | 5 | | | | | 10 | | | | | 15 | |

| Trp | Ser | Glu | Asp | Cys | Arg | Leu | Glu | Gly | Gly | Gly | Gly | Pro | Ala | Gly | Gly |
|---|---|---|---|---|---|---|---|---|---|---|---|---|---|---|---|
| | | | 20 | | | | | 25 | | | | | 30 | | |

| Phe | Glu | Asp | Glu | Gly | Glu | Asp | Lys | Lys | Val | Arg | Gly | Glu | Gly | Pro | Gly |
|---|---|---|---|---|---|---|---|---|---|---|---|---|---|---|---|
| | | | 35 | | | | | 40 | | | | | 45 | | |

| Glu | Ala | Gly | Gly | Pro | Leu | Thr | Pro | Arg | Arg | Val |
|---|---|---|---|---|---|---|---|---|---|---|
| | | 50 | | | | | 55 | | | |

( 2 ) INFORMATION FOR SEQ ID NO:6:

( i ) SEQUENCE CHARACTERISTICS:
        ( A ) LENGTH: 2544 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: -
    ( B ) LOCATION: 1..2544
    ( D ) OTHER INFORMATION: /note= "genomic DNA sequence for murine ERF gene (promoter region and first exon not included)"

( x i ) SEQUENCE DESCRIPTION: SEQ ID NO:6:

```
ATAGGGGGCT GTGTCCCCAT CCTGCTGGCC ACGTGTATAC CCTTTTCTGC CCCTCACCCT      60
CCCTCACTGG CAGCCCTGCC CGCCATCCTG GCTTGGTGCC TGGCCCCCTG GCACTGGCCC     120
CGGGACCCGC CGCCGTTGGT TTCCTGTTTC TCCCGGTGTC GCTGGAGCCG ACTCCAGCTT     180
CCCCTCCTCC CAGCTCCTGT CTAGGCCCCT CACGCAGATG CCCATACGGT TACTCTCAGA     240
TTTGGGTCTT CATCTGGCTG AGGAAAAGGG CTTTCCTGAT GGTGGAAGAC TGAGGGGTGG     300
GGCAGGACAT AAAAACTCCA GTAGGAGCCA GAGCCCCAC  CTTGGCATCT TGACCCCAGG     360
CAACTCCCTG TCTCCTGTCC CTAGGGTTTG CCTTCCCAGA TTGGGCCTAC AAACCGGAGT     420
CATCCCCTGG CTCCAGGCAG ATCCAGCTGT GGCACTTTAT CCTGGAGCTG CTTCGGAAAG     480
AGGAGTACCA GGGCGTCATC GCTTGGCAGG GGGACTACGG GGAGTTTGTC ATCAAGGACC     540
CTGATGAAGT GGCTCGCCTC TGGGGGGTCC GCAAGTGCAA ACCCAGATG  AACTATGACA     600
AGCTGAGCCG GGCTTTGCGG TGAGAAGGGG CTGTGGGCCC CAGAGGACAT GTGGCAGGTC     660
CCTATGGTTG GAAATTCTTG ATACATAAGG ACAGGTTTTG GGTTTGATGT CTAGCTGGCT     720
CTGCTAGGTC TAGCTGTGTC AACTTGGGCC TTGGGCAAGT CCTGCCAGTC TTGTGAACTC     780
ATAGGTCATA CAGAGGTGTC CCAGGCAAAG AAATGTAGCT GGAGACTCTA GTGTGCTCCT     840
GGTTACTTGA TTTCTCGGCT GTTGGGTACC CTTTATGCAT GAGACCCAGC CTTGTATCAT     900
GGTGCCTGGG TCCTGTGGAG GGTGGCTTGA TGCCCGATG  GTGTTTATG  CCCACAGCTA     960
TTATTACAAC AAGCGCATTC TACACAAGAC CAAGGGGAAA CGGTTCACCT ACAAGTTCAA    1020
CTTCAACAAA CTGGTGCTGG TCAATTACCC TTTCATCGAT ATGGGGCTGG CTGGTGAGTG    1080
TGTGGCCTGC GTGTCAGAAG AGGGTGAAGA GGTGGGGTTT TCTGTGTTCA GAGGAGACCA    1140
GAGAACATGA TGCCTACTCT CCCTTCTTTT GTCAGGGGGT GCAGTTCCCC AAAGCGCCCC    1200
ACCAGTGCCA TCAGGCGGCA GCCATTTCCG CTTCCCTCCC TCAACACCCT CCGAGGTGCT    1260
GTCCCCCACT GAGGATCCCC GATCTCCACC GGCTTGTTCT TCATCATCCT CTTCTCTCTT    1320
CTCTGCTGTG GTTGCCCGAC GCCTGGGCCG AGGCTCAGTC AGTGACTGTA GTGATGGCAC    1380
ATCAGAGCTG GAGGAGCCTC TGGGAGAGGA CCCCAGGGCA CGACCACCTG GCCCTCCGGA    1440
GCTGGGTGCC TTCCGAGGGC CCCCCCTGGC CCGCCTCCCG CATGACCCTG GTGTCTTCCG    1500
TGTCTATCCT CGGCCCCGGG GTGGTCCTGA ACCCCTGAGT CCCTTCCCTG TGTCACCTTT    1560
GGCTGGGCCT GGCTCCCTTC TACCCCCTCA GCTCTCCCCA GCTCTGCCCA TGACTCCCAC    1620
CCACCTGGCC TACACACCCT CACCCACGCT GAGTCCTATG TACCCCAGTG GTGGTGGGGG    1680
CCCTAGTGGC TCAGGGGAG  GTTCCACTT  CTCCTTCAGT CCTGAGGACA TGAAACGGTA    1740
CCTGCAGGCC CACACCCAAA GCGTCTACAA CTACCACCTC AGTCCCCGCG CCTTCTTGCA    1800
CTACCCAGGG CTGGTGGTGC CCCAGCCTCA GCGCCCTGAC AAGTGCCCAC TGCCGCCCAT    1860
GGCACCGGAG ACCCCGCCGG TCCCCTCCTC AGCCTCGTCT TCCTCTTCCT CCTCTTCATC    1920
CCCGTTCAAG TTTAAGCTGC AGCCACCCCC GCTAGGACGC CGGCAGCGGG CAGCTGGAGA    1980
GAAGGCTCCA GGAGGCACTG ACAAGAGCAG TGGTGGCAGT GGCTCGGGTG GACTGGCTGA    2040
GGGGGCAGGT GCAGTAGCTC CCCCACCGCC ACCACCCCAG ATTAAGGTGG AGCCCATCTC    2100
```

-continued

| | | | | | |
|---|---|---|---|---|---|
| AGAAGGAGAG | TCGGAGGAGG | TGGAGGTGAC | TGACATCAGT | GACGAAGATG | AGGAAGATGG | 2160 |
| GGAGGTGTTC | AAGACCCCCC | GTGCCCCGCC | TGCTCCCCCC | AAGCCAGAGC | CCGGAGAGGC | 2220 |
| ACCGGGGGTG | GCCCAGTGCA | TGCCCCTTAA | ACTGCGCTTT | AAGCGGCGCT | GGAGTGAAGA | 2280 |
| CTGTCGCCTG | GAGGGGGGCG | GGTGCCTGTC | TGGGGGCCCT | GAAGATGAGG | GTGAGGACAA | 2340 |
| GAAGGTGCGT | GGGGACGTGG | GCCCTGGGGA | GTCTGGGGGA | CCCCTTACCC | CACGACGGGT | 2400 |
| GAGCTCTGAC | CTCCAGCACG | CCACAGCCCA | ACTCTCCCTG | GAGCACCGAG | ATTCCTGAGA | 2460 |
| GCTATGGGCA | CGGGGGCACG | GGCCCACCCC | CACCCACCCA | CCCCACTCCC | TGAGCTTTTG | 2520 |
| CTGCCTTAAC | CGCCCCGCCC | CCGC | | | | 2544 |

( 2 ) INFORMATION FOR SEQ ID NO:7:

( i ) SEQUENCE CHARACTERISTICS:
        ( A ) LENGTH: 543 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein
        ( B ) LOCATION: 1..543
        ( D ) OTHER INFORMATION: /note= "murine ERF amino acid sequence
            (first 8 amino acids from first exon not
            included)"

( x i ) SEQUENCE DESCRIPTION: SEQ ID NO:7:

```
Phe Ala Phe Pro Asp Trp Ala Tyr Lys Pro Glu Ser Ser Pro Gly Ser
 1               5                  10                  15

Arg Gln Ile Gln Leu Trp His Phe Ile Leu Glu Leu Leu Arg Lys Glu
                20                  25                  30

Glu Tyr Gln Gly Val Ile Ala Trp Gln Gly Asp Tyr Gly Glu Phe Val
            35                  40                  45

Ile Lys Asp Pro Asp Glu Val Ala Arg Leu Trp Gly Val Arg Lys Cys
        50                  55                  60

Lys Pro Gln Met Asn Tyr Asp Lys Leu Ser Arg Ala Leu Arg Tyr Tyr
65                  70                  75                  80

Tyr Asn Lys Arg Ile Leu His Lys Thr Lys Gly Lys Arg Phe Thr Tyr
                85                  90                  95

Lys Phe Asn Phe Asn Lys Leu Val Leu Val Asn Tyr Pro Phe Ile Asp
            100                 105                 110

Met Gly Leu Ala Gly Gly Ala Val Pro Gln Ser Ala Pro Pro Val Pro
        115                 120                 125

Ser Gly Gly Ser His Phe Arg Phe Pro Pro Ser Thr Pro Ser Glu Val
    130                 135                 140

Leu Ser Pro Thr Glu Asp Pro Arg Ser Pro Pro Ala Cys Ser Ser Ser
145                 150                 155                 160

Ser Ser Ser Leu Phe Ser Ala Val Val Ala Arg Arg Leu Gly Arg Gly
                165                 170                 175

Ser Val Ser Asp Cys Ser Asp Gly Thr Ser Glu Leu Glu Pro Leu
            180                 185                 190

Gly Glu Asp Pro Arg Ala Arg Pro Pro Gly Pro Pro Glu Leu Gly Ala
        195                 200                 205

Phe Arg Gly Pro Pro Leu Ala Arg Leu Pro His Asp Pro Gly Val Phe
    210                 215                 220

Arg Val Tyr Pro Arg Pro Arg Gly Gly Pro Glu Pro Leu Ser Pro Phe
225                 230                 235                 240
```

```
Pro  Val  Ser  Pro  Leu  Ala  Gly  Pro  Gly  Ser  Leu  Leu  Pro  Pro  Gln  Leu
               245                      250                           255

Ser  Pro  Ala  Leu  Pro  Met  Thr  Pro  Thr  His  Leu  Ala  Tyr  Thr  Pro  Ser
               260                      265                      270

Pro  Thr  Leu  Ser  Pro  Met  Tyr  Pro  Ser  Gly  Gly  Gly  Pro  Ser  Gly
          275                      280                 285

Ser  Gly  Gly  Gly  Ser  His  Phe  Ser  Phe  Ser  Pro  Glu  Asp  Met  Lys  Arg
          290                      295                      300

Tyr  Leu  Gln  Ala  His  Thr  Gln  Ser  Val  Tyr  Asn  Tyr  His  Leu  Ser  Pro
305                      310                      315                      320

Arg  Ala  Phe  Leu  His  Tyr  Pro  Gly  Leu  Val  Val  Pro  Gln  Pro  Gln  Arg
               325                      330                           335

Pro  Asp  Lys  Cys  Pro  Leu  Pro  Pro  Met  Ala  Pro  Glu  Thr  Pro  Pro  Val
               340                      345                      350

Pro  Ser  Ser  Ala  Ser  Ser  Ser  Ser  Ser  Ser  Ser  Ser  Pro  Phe  Lys
          355                      360                      365

Phe  Lys  Leu  Gln  Pro  Pro  Pro  Leu  Gly  Arg  Arg  Gln  Arg  Ala  Ala  Gly
     370                      375                 380

Glu  Lys  Ala  Pro  Gly  Gly  Thr  Asp  Lys  Ser  Ser  Gly  Gly  Ser  Gly  Ser
385                      390                 395                           400

Gly  Gly  Leu  Ala  Glu  Gly  Ala  Gly  Ala  Val  Ala  Pro  Pro  Pro  Pro
               405                      410                      415

Pro  Gln  Ile  Lys  Val  Glu  Pro  Ile  Ser  Glu  Gly  Glu  Ser  Glu  Glu  Val
               420                      425                      430

Glu  Val  Thr  Asp  Ile  Ser  Asp  Glu  Asp  Glu  Asp  Gly  Glu  Val  Phe
               435                      440                 445

Lys  Thr  Pro  Arg  Ala  Pro  Pro  Ala  Pro  Pro  Lys  Pro  Glu  Pro  Gly  Glu
     450                      455                 460

Ala  Pro  Gly  Val  Ala  Gln  Cys  Met  Pro  Leu  Lys  Leu  Arg  Phe  Lys  Arg
465                      470                      475                      480

Arg  Trp  Ser  Glu  Asp  Cys  Arg  Leu  Glu  Gly  Gly  Gly  Cys  Leu  Ser  Gly
               485                      490                      495

Gly  Pro  Glu  Asp  Glu  Gly  Glu  Asp  Lys  Lys  Val  Arg  Gly  Asp  Val  Gly
               500                      505                      510

Pro  Gly  Glu  Ser  Gly  Gly  Pro  Leu  Thr  Pro  Arg  Arg  Val  Ser  Ser  Asp
          515                      520                      525

Leu  Gln  His  Ala  Thr  Ala  Gln  Leu  Ser  Leu  Glu  His  Arg  Asp  Ser
     530                      535                      540
```

( 2 ) INFORMATION FOR SEQ ID NO:8:

( i ) SEQUENCE CHARACTERISTICS:
        ( A ) LENGTH: 332 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: -
        ( B ) LOCATION: 1..332
        ( D ) OTHER INFORMATION: /note= "human ERF gene promoter region"

( x i ) SEQUENCE DESCRIPTION: SEQ ID NO:8:

```
CCGCGGGACC  CCATCCCACC  CCCACCCCCT  CCTTCCTCCC  TCCCCCGCCG  CGCGGCCCCT      60

TTAAGCCCAG  AGCCGGCCGG  TCCTCAGTGC  TGCGCGCCGA  CGAGCGTGTG  TGTGAGTGCG     120
```

| | | | | | |
|---|---|---|---|---|---|
| CGGGGAGGGG | GCGGGCGCAG | TGTCTCCATG | GCGACGCGGC | GGTGACGTCG | CCGGCCGGGG | 180
| GGCGTGGGCG | TCCCGGCCCC | GGAGTGCGAT | ATTAACCCGG | GAGGCGGCGG | CGGGGAGGGG | 240
| AGAGGCTCTG | AGAGGCGAGG | CCGGGTGAGG | CGGCGAGGGC | GGCCCGACGG | GCGCGGGACG | 300
| GGACGGGGCA | GCGAGGGCGC | CGGGAGCCGC | GG | | | 332

( 2 ) INFORMATION FOR SEQ ID NO:9:

( i ) SEQUENCE CHARACTERISTICS:
    ( A ) LENGTH: 16 base pairs
    ( B ) TYPE: nucleic acid
    ( C ) STRANDEDNESS: double
    ( D ) TOPOLOGY: linear ( i i ) MOLECULE TYPE: DNA ( i x ) FEATURE:
    ( A ) NAME/KEY: -
    ( B ) LOCATION: 1..16
    ( D ) OTHER INFORMATION: /note= "double-stranded H1
      oligonucleotide"

( x i ) SEQUENCE DESCRIPTION: SEQ ID NO:9:

GATCTGGAGG AAGTAA                         16

( 2 ) INFORMATION FOR SEQ ID NO:10:

( i ) SEQUENCE CHARACTERISTICS:
    ( A ) LENGTH: 78 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Domain
    ( B ) LOCATION: 1..78
    ( D ) OTHER INFORMATION: /note= "ets-like ERF DNA-binding
      domain"

( x i ) SEQUENCE DESCRIPTION: SEQ ID NO:10:

```
Leu  Trp  His  Phe  Ile  Leu  Glu  Leu  Leu  Arg  Lys  Glu  Glu  Tyr  Gln  Gly
 1              5                        10                       15

Val  Ile  Ala  Trp  Gln  Gly  Asp  Tyr  Gly  Glu  Phe  Val  Ile  Lys  Asp  Pro
            20                       25                        30

Asp  Glu  Val  Ala  Arg  Leu  Trp  Gly  Val  Arg  Lys  Cys  Lys  Pro  Gln  Met
         35                       40                        45

Asn  Tyr  Asp  Lys  Leu  Ser  Arg  Ala  Leu  Arg  Tyr  Tyr  Asn  Lys  Arg
     50                       55                        60

Ile  Leu  His  Lys  Thr  Lys  Gly  Lys  Arg  Phe  Thr  Tyr  Lys  Phe
 65                       70                        75
```

( 2 ) INFORMATION FOR SEQ ID NO:11:

( i ) SEQUENCE CHARACTERISTICS:
    ( A ) LENGTH: 78 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Domain
    ( B ) LOCATION: 1..78
    ( D ) OTHER INFORMATION: /note= "ETS1 homologous region to
      ets-like ERF DNA-binding domain"

( x i ) SEQUENCE DESCRIPTION: SEQ ID NO:11:

| Leu | Trp | Gln | Phe | Leu | Leu | Glu | Leu | Leu | Thr | Asp | Lys | Ser | Cys | Gln | Ser |
|---|---|---|---|---|---|---|---|---|---|---|---|---|---|---|---|
| 1 | | | | 5 | | | | | 10 | | | | | 15 | |

| Phe | Ile | Ser | Trp | Thr | Gly | Asp | Gly | Trp | Glu | Phe | Lys | Leu | Ser | Asp | Pro |
|---|---|---|---|---|---|---|---|---|---|---|---|---|---|---|---|
| | | | 20 | | | | | 25 | | | | | 30 | | |

| Asp | Glu | Val | Ala | Arg | Arg | Trp | Gly | Lys | Arg | Lys | Asn | Lys | Pro | Lys | Met |
|---|---|---|---|---|---|---|---|---|---|---|---|---|---|---|---|
| | | | 35 | | | | | 40 | | | | | 45 | | |

| Asn | Tyr | Glu | Lys | Leu | Ser | Arg | Gly | Leu | Arg | Tyr | Tyr | Asp | Lys | Asn |
|---|---|---|---|---|---|---|---|---|---|---|---|---|---|---|
| | 50 | | | | | 55 | | | | | 60 | | | |

| Ile | Ile | His | Lys | Thr | Ala | Gly | Lys | Arg | Tyr | Val | Tyr | Arg | Phe |
|---|---|---|---|---|---|---|---|---|---|---|---|---|---|
| 65 | | | | | 70 | | | | | 75 | | | |

( 2 ) INFORMATION FOR SEQ ID NO:12:

( i ) SEQUENCE CHARACTERISTICS:
        ( A ) LENGTH: 79 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Domain
        ( B ) LOCATION: 1..79
        ( D ) OTHER INFORMATION: /note= "ELK1 homologous region to
            ets-like ERF DNA-binding domain"

( x i ) SEQUENCE DESCRIPTION: SEQ ID NO:12:

| Leu | Trp | Gln | Phe | Leu | Leu | Gln | Leu | Leu | Arg | Glu | Gln | Gly | Asn | Gly | His |
|---|---|---|---|---|---|---|---|---|---|---|---|---|---|---|---|
| 1 | | | | 5 | | | | | 10 | | | | | 15 | |

| Ile | Ile | Ser | Trp | Thr | Ser | Arg | Asp | Gly | Gly | Glu | Phe | Lys | Leu | Val | Asp |
|---|---|---|---|---|---|---|---|---|---|---|---|---|---|---|---|
| | | | 20 | | | | | 25 | | | | | 30 | | |

| Ala | Glu | Glu | Val | Ala | Arg | Leu | Trp | Gly | Leu | Arg | Lys | Asn | Lys | Thr | Asn |
|---|---|---|---|---|---|---|---|---|---|---|---|---|---|---|---|
| | | | 35 | | | | | 40 | | | | | 45 | | |

| Met | Asn | Tyr | Asp | Lys | Leu | Ser | Arg | Ala | Leu | Arg | Tyr | Tyr | Asp | Lys |
|---|---|---|---|---|---|---|---|---|---|---|---|---|---|---|
| | 50 | | | | | 55 | | | | | 60 | | | |

| Asn | Ile | Ile | Arg | Lys | Val | Ser | Gly | Gln | Lys | Phe | Val | Tyr | Lys | Phe |
|---|---|---|---|---|---|---|---|---|---|---|---|---|---|---|
| 65 | | | | | 70 | | | | | 75 | | | | |

( 2 ) INFORMATION FOR SEQ ID NO:13:

( i ) SEQUENCE CHARACTERISTICS:
        ( A ) LENGTH: 78 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Domain
        ( B ) LOCATION: 1..78
        ( D ) OTHER INFORMATION: /note= "Pea3 homologous region to
            ets-like ERF DNA-binding domain"

( x i ) SEQUENCE DESCRIPTION: SEQ ID NO:13:

| Leu | Trp | Gln | Phe | Leu | Val | Ala | Leu | Leu | Asp | Asp | Pro | Thr | Asn | Ala | His |
|---|---|---|---|---|---|---|---|---|---|---|---|---|---|---|---|
| 1 | | | | 5 | | | | | 10 | | | | | 15 | |

| Phe | Ile | Ala | Trp | Thr | Gly | Arg | Gly | Met | Glu | Phe | Lys | Leu | Ile | Glu | Pro |
|---|---|---|---|---|---|---|---|---|---|---|---|---|---|---|---|
| | | | 20 | | | | | 25 | | | | | 30 | | |

| Glu | Glu | Val | Ala | Arg | Leu | Trp | Gly | Ile | Gln | Lys | Asn | Arg | Pro | Ala | Met |
|---|---|---|---|---|---|---|---|---|---|---|---|---|---|---|---|
| | | | 35 | | | | | 40 | | | | | 45 | | |

| Asn | Tyr | Asp | Lys | Leu | Ser | Arg | Ser | Leu | Arg | Tyr | Tyr | Tyr | Glu | Lys | Gly |
|---|---|---|---|---|---|---|---|---|---|---|---|---|---|---|---|

```
                         5 0                          5 5                          6 0

I l e   M e t   G l n   L y s   V a l   A l a   G l y   G l u   A r g   T y r   V a l   T y r   L y s   P h e
           6 5                                    7 0                                   7 5
```

( 2 ) INFORMATION FOR SEQ ID NO:14:

( i ) SEQUENCE CHARACTERISTICS:
        ( A ) LENGTH: 81 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Domain
        ( B ) LOCATION: 1..81
        ( D ) OTHER INFORMATION: /note= "Yan homologous region to
            ets-like ERF DNA-binding domain"

( x i ) SEQUENCE DESCRIPTION: SEQ ID NO:14:

```
           L e u   T r p   A s p   P h e   L e u   G l n   G l n   L e u   L e u   A s n   A s p   A r g   A s n   G l n   L y s   T y r
           1                                 5                                  1 0                                 1 5

S e r   A s p   L e u   I l e   A l a   T r p   L y s   C y s   A r g   A s p   T h r   G l y   V a l   P h e   L y s   I l e
                                   2 0                                  2 5                                 3 0

V a l   A s p   P r o   A l a   G l y   L e u   A l a   L y s   L e u   T r p   G l y   I l e   G l n   L y s   A s n   H i s
                                   3 5                                  4 0                                 4 5

L e u   S e r   M e t   A s n   T y r   A s p   L y s   M e t   S e r   A r g   A l a   L e u   A r g   T y r   T y r   T y r
                          5 0                                   5 5                                 6 0

A r g   V a l   A s n   I l e   L e u   A r g   L y s   V a l   G l n   G l y   G l u   A r g   H i s   C y s   T y r   G l n
           6 5                                   7 0                                 7 5                                            8 0

P h e
```

( 2 ) INFORMATION FOR SEQ ID NO:15:

( i ) SEQUENCE CHARACTERISTICS:
        ( A ) LENGTH: 80 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Domain
        ( B ) LOCATION: 1..80
        ( D ) OTHER INFORMATION: /note= "E74 homologous region to
            ets-like ERF DNA-binding domain"

( x i ) SEQUENCE DESCRIPTION: SEQ ID NO:15:

```
           L e u   T r p   G l u   P h e   L e u   L e u   L y s   L e u   L e u   G l n   A s p   A r g   G l u   T y r   C y s   P r o
           1                                 5                                  1 0                                 1 5

A r g   P h e   I l e   L y s   T r p   T h r   A s n   A r g   G l u   L y s   G l y   V a l   P h e   L y s   L e u   V a l
                                   2 0                                  2 5                                 3 0

A s p   S e r   L y s   A l a   V a l   S e r   A r g   L e u   T r p   G l y   M e t   H i s   L y s   A s n   L y s   P r o
                                   3 5                                  4 0                                 4 5

A s p   M e t   A s n   T y r   G l u   T h r   M e t   G l y   A r g   A l a   L e u   A r g   T y r   T y r   T y r   G l n
                          5 0                                   5 5                                 6 0

A r g   G l y   I l e   L e u   A l a   L y s   V a l   A s p   G l y   G l n   A r g   L e u   V a l   T y r   H i s   P h e
           6 5                                   7 0                                 7 5                                            8 0
```

( 2 ) INFORMATION FOR SEQ ID NO:16:

( i ) SEQUENCE CHARACTERISTICS:
        ( A ) LENGTH: 81 amino acids ( B ) TYPE: amino acid
( C ) STRANDEDNESS:
( D ) TOPOLOGY: linear ( i i ) MOLECULE TYPE: peptide ( i x ) FEATURE:
 ( A ) NAME/KEY: Domain
 ( B ) LOCATION: 1..81
 ( D ) OTHER INFORMATION: /note= "Pu.1 homologous region to ets-like ERF DNA-binding domain"

( x i ) SEQUENCE DESCRIPTION: SEQ ID NO:16:

```
Leu Tyr Gln Phe Leu Leu Asp Leu Leu Arg Ser Gly Asp Met Lys Asp
 1               5                  10                  15

Ser Ile Trp Trp Val Asp Lys Asp Lys Gly Thr Phe Gln Phe Ser Ser
            20                  25                  30

Lys His Lys Glu Ala Leu Ala His Arg Trp Gly Ile Gln Lys Gly Asn
         35                  40                  45

Arg Lys Lys Met Thr Tyr Gln Lys Met Ala Arg Ala Leu Arg Asn Tyr
     50                  55                  60

Gly Lys Thr Gly Glu Val Lys Lys Val Lys Lys Lys Leu Thr Tyr Gln
 65                  70                  75                  80

Phe
```

ETS2 REPRESSOR FACTOR (ERF) GENETIC LOCUS AND ITS PRODUCTS

FIELD OF THE INVENTION

The present invention relates, inter alia, to the ERF gene and to the products encoded by this gene. More particularly, the present invention relates to DNA sequences encoding ERF and AERF; polypeptides encoded by such DNA sequences; ERF chimeric molecules; and methods of using ERF and ERF chimeric molecules to reduce tumorigenicity in a tumor cell.

BACKGROUND OF THE INVENTION

Transcriptional regulators in eukaryotic cells are organized into families of genes characterized by their DNA-binding domain and DNA sequence specificity (homeo domain, b-ZIP, HLH, ets domain, Re1 homology region, etc.) (see, e.g., Pabo, et al., *Annu. Rev. Biochem.*, 61:1015–1023 (1992)). Although some functional redundancy exists, the specific function of each member of a given family is defined by a configuration of factors involving tissue-specificity and cell cycle regulation, response to extracellular signals, level of expression, interacting proteins, target specificity, kinetics of interaction and effect on transcription (positive or negative). However, the members of a family are usually involved in a common function (e.g., homeo genes and development, AP1 genes and mitogenic stimulation, etc.). The ets family of genes recognize a common target sequence and have been implicated in cellular proliferation and tumorigenesis (see, e.g., Seth, et al., *Cell Growth Differ*, 3:327–334 (1992); Macleod, et al., *TIBS*, 17:251–256 (1992); Wasylyk, et al., *Eur. J. Biochem.*, 211:8–19 (1993); and Janknecht, et al., *Biochim. Biophys. Acta*, 1155:346–356 (1993)). Several growth-related genes contain a functional ets-binding site (EBS) in their regulatory region, including c-fos (for review see Treisman, et al., *Curr. Opinion Genet. Dev.*, 4:96–101 (1994); Karin, et al., *Curr. Opinion Cell Biol.*, 6:415–424 (1994)), Jun-B (Coffer, et al., *Oncogene*, 9:911–921 (1994)), Rb (Savoysky, et al., *Oncogene*, 9:1839–1846 (1994)), c-MYC (Roussel, et al., *Oncogene*, 9:405–415 (1994)) and ETS2 (Mavrothalassitis, et al., *Cell Growth Differ*, 2:215–224 (1991)), indicating that members of the ets family may play a key role during mitogenic stimulation by regulating the transcription of these genes. Furthermore, recent reports indicate that the activity of some ets family members can be regulated by the ras/MAPK pathway (Janknecht, et al., *EMBO*, 12:5097–5104 (1993); Rao, et al., *Oncogene*, 9:1855–1860 (1994); O'Neill, et al., *Cell*, 78:137–147 (1994); Brunner, et al., *Nature*, 370:386–389 (1994) and, thus, provide a possible mechanism for the coordinated regulation of the function of some ets genes during mitogenic stimulation.

In an efforts to analyze regulation of the ETS2 gene, its promoter was isolated and characterized (Mavrothalassitis, et al., *Oncogene*, 5:1337–1342 (1990), Mavrothalassitis, et al., *Proc. Natl. Sci. USA*, 87:1047–1051 (1990)), and sites where protein interaction is required for promoter function were identified (Mavrothalassitis, et al., *Cell Growth Differ.*, 2:215–224 (1991)). One of the DNA-protein interaction sites on the ETS2 promoter, designated H1, is an ets-binding site, thus suggesting a regulatory loop among the members of the ets family. However, neither ETS1 nor ETS2 are capable of regulating ETS2 transcription via this site, and they both have a low affinity for this particular sequence, indicating that other members of the family are responsible for the transcriptional regulation of the ETS2 gene.

As such, there remains a need in the art for the identification of the gene responsible for the transcriptional regulation of the ETS2 gene.

SUMMARY OF THE INVENTION

It has now been discovered that ERF (ETS2 Repressor Factor), a novel member of the ets family of genes, is the gene responsible for the transcriptional regulation of the ETS2 gene. Moreover, it has now been discovered that ERF can regulate the transcription of other genes having ets-binding sites. As such, the ERF gene can be used in vivo and in vitro to suppress or repress transcription and to elucidate transcription process and regulation. ERF is the first member of the ets family to be identified as a transcriptional repressor in mammalian cells. ERF has no significant homology to the only other known repressor member of the ets family, i.e., the Drosophila gene Yan, or to other transcriptional repressors. In addition to being a transcrptional repressor, it has also been discovered that the ERF gene possesses tumor suppressor activity and, thus, ERF can be used to suppress ets-dependent tumorigenicity as well as tumorigenicity associated with the inappropriate expression of transcription factors.

As such, in one aspect, the present invention provides isolated nucleic acid sequences, i.e., polynucleotides, which encode a family of proteins. More particularly, the present invention provides a DNA sequence (SEQ ID NO:1) which is transcribed into an mRNA of about 2.7 kb which encodes a human ERF protein having an amino acid sequence comprising SEQ ID NO: 2. Moreover, the present invention provides an isolated DNA sequence (SEQ ID NO:3) which is transcribed into an mRNA of about 2.5 kb which encodes a human AERF protein having an amino acid sequence comprising SEQ ID NO:4. In addition, the present invention provides an isolated DNA sequence encoding a murine ERF protein having an amino acid comprising SEQ ID NO:7.

In another aspect, the present invention provides isolated, substantially purified ERF and AERF proteins. More particularly, the present invention provides an isolated, substantially purified human ERF protein encoded by an mRNA of about 2.7 kb and having an amino acid sequence comprising SEQ ID NO: 1. Additionally, the present invention provides an isolated, substantially purified human AERF protein encoded by an mRNA of about 2.5 kb and having an amino acid sequence comprising SEQ ID NO: 4. Moreover, the present invention provides an isolated, substantially purified murine ERF protein having an amino acid sequence comprising SEQ ID NO:7.

In yet another aspect, the present invention provides an ERF chimeric molecule, the ERF chimeric molecule comprising an ERF repressor domain in combination with a heterologous transcription factor having a binding domain. It has been discovered that ERF contains an active repressor domain located between amino acids 472 and 530, and corresponding to SEQ ID NO:5. The ERF repressor domain does not contain any recognizable features reported for other transcriptional repressors and has no homology to previously reported repressor genes. Moreover, it has been discovered that the ERF repressor domain can be effectively transferred to transcription factors having a binding domain (e.g., GAL4, NFκB (p50 and p65), MYC, Fli-1, EST1, etc.) to generate transcriptional repressors. As such, the present invention provides ERF chimeric molecules which are effective transcriptional repressors.

In still another embodiment, the present invention provides a method for reducing ets-dependent tumorigenicity, the method comprising: transfecting a tumor cell with an ERF gene. Moreover, the present invention provides a method for reducing ets-dependent tumorigenicity, the method comprising contacting a tumor cell with a peptide expressed by an ERF gene. In addition, the present invention provides a method for reducing cell tumorigenicity associated with the inappropriate expression of a transcription factor, the method comprising contacting a tumor cell with an ERF chimeric molecule, the ERF chimeric molecule comprising an ERF repressor domain in combination with the transcription factor having a binding domain. Using these methods, one can reduce tumorigenicity associated with, inter alia, the v-mos, c-met, tpr-met, Ha-ras and gag-myb-ets oncogenes or, alternatively, one can reduce tumorigenicity associated with, inter alia, the inappropriate expression of the GAL4, NFκB (HIV), MYC (Burkitt Lymphoma), Fli-1 (Ewing's Sarcoma) and EST1 transcription factors.

Other advantages, objects, features and embodiments of the present invention will become apparent from the description which follows.

BRIEF DESCRIPTION OF THE DRAWINGS

FIG. 1 illustrates the isolation and characterization of ERF cDNA. (A) Schematic representation of the ERF cDNA. The coding region is represented by the boxed area. The diamond indicates the 5' stop codon and the open circle the polyadenylation signal. The lines below represent the segments of the cDNA contained in the indicated clone isolates. (B) Sequence of the ERF cDNA (SEQ ID NO:1) and the predicted ERF protein (SEQ ID NO:2). The ets-like DNA-binding domain of the protein is boxed. (C) Sequence homology of the ERF DNA-binding domain (SEQ ID NO:10) to other members of the ets family. The identity within the 82 amino acids region is 64% for ETS1 (SEQ ID NO:11), 59% for ELK1 (SEQ ID NO:12), 56% for Pea3 (SEQ ID NO:13), 47% for Yan (SEQ ID NO:14), 45% for E74 (SEQ ID NO:15) and 31% for Pu.1 (SEQ ID NO:16).

FIGS. 9A and B illustrates the alternative splicing of ERF. The ERF gene produces a second protein as a result of alternative splicing of the second exon. This alternative splicing generates a 191 amino acid protein (SEQ ID NO:4), i.e., AERF (Alternative ERF), with no homology to other known proteins.

FIGS. 10A and B illustrates the isolation and characterization of the ERF promoter (SEQ ID NO:8). The low level constitutive expression of the ERF promoter can be used in transgenic animal studies to introduce ubiquitously expressed transgenes, but at a low level of expression.

DEFINITIONS

Figure 2A:
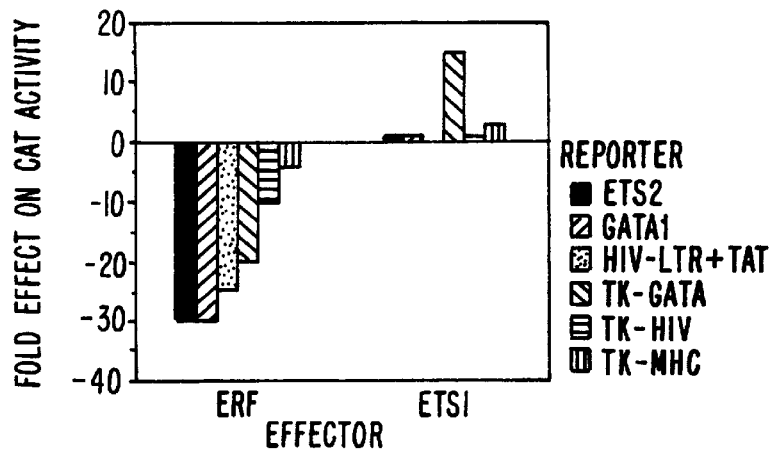
FIG. 2 illustrates that ERF is a potent transcriptional repressor. (A) Transient transfection of HeLa cells with 2 μg of the indicated reporter plasmids in the presence or absence of 3 μg of the pSG5/ERF expression plasmid. Three micrograms of pSG5/ETS1 expression plasmid was used as a control. The numbers indicate fold differences in the CAT levels compared to the reporter plasmid alone. Indicated values are the result of at least three independent experiments. Repression values higher than 30-fold were considered to be 30-fold because of limited accuracy at very low CAT levels. (B) The repressor activity of ERF can be antagonized by a transactivator like ETS1. Two micrograms of the two reporter plasmids were co-transfected with the indicated effectors at the indicated ratio. The numbers are as in (A). (C) The GAL4 DNA-binding domain was fused to the indicated segments of the ERF gene (numbers represent amino acid position). Three micrograms of each plasmid were co-transfected into HeLa cells with 1 μg of an SV40-based reporter that contains five GAL4 binding sites in tandem. The numbers indicate fold inhibition in CAT activity over the reporter transfected alone. The values are the average of at least three independent experiments. (D) Nuclear extracts were prepared after transient transfection of the indicated plasmids into HeLa cells and the GAL4 binding activity was determined by EMSA. The DNA fragment containing five GAL4 binding sites that was used to modify the SV40 reporter was used as a probe. Plus and minus indicates the presence or absence of 100-fold excess of unlabeled probe. The numbers below indicate fold inhibition of CAT activity in this experiment.

"Nucleic acid," as used herein, refers to a deoxyribonucleotide (DNA) or ribonucleotide (RNA) in either single- or double-stranded form, and unless otherwise limited, encompasses known analogs of natural nucleotides which can function in a manner similar to the naturally occurring nucleotides.

The phrase "nucleic acid sequence" refers to a single- or double-stranded polymer of deoxyribonucleotide or ribonucleotide bases read from the 5' to the 3' end. It includes both self-replicating plasmids, infectious polymers of DNA or RNA and non-functional DNA or RNA. Additionally, substantial nucleic acid sequence identity exists when a nucleic acid segment will hybridize, under selective hybridization conditions, to a complement of another nucleic acid strand. Nucleotide sizes are given in either kilobases (kb) or base pairs (bp). These are estimates derived from agarose or acrylamide gel electrophoresis.

The phrase "DNA sequence" refers to a single- or double-stranded DNA polymer composed of the nucleotide bases, adenosine, thymidine, cytosine and guanosine.

The phrase "nucleic acid sequence encoding" refers to a nucleic acid sequence which directs the expression of a specific protein or peptide. The nucleic acid sequences include both the DNA sequence that is transcribed into RNA and the RNA sequence that is translated into the protein. The nucleic acid sequence includes both the full length nucleic acid sequence as well as non-full length sequences derived from the full length sequence. It will be understood by those of skill that the sequence includes the degenerate codons of the native sequence or sequences which may be introduced to provide codon preference in a specific host cell.

The term "complementary" refers to a nucleic acid segment that will hybridize, under selective hybridization conditions, to a complement of another nucleic acid strand. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%. See, Kanehisa, *Nucleic Acids Res.,* 12:203 (1984), incorporated herein by reference.

"Isolated" or "substantially pure," when referring to nucleic acids, refer to those that have been purified away from other cellular components and contaminants, i.e., other cellular nucleic acids and/or proteins, by standard techniques, including, for example, alkaline/SDS treatment, CsCl banding, column chromatography, and others purification techniques well known in the art. See, e.g., *Methods in Enzymology,* Vol. 152: *Guide to Molecular Cloning Techniques* (Berger and Kimmel (eds.), San Diego: Academic Press, Inc. (1987)), and *Current Protocols in Molecular Biology* (Ausubel, et al., (ed.), Greene Publishing and Wiley-Interscience, New York (1987)), both of which are incorporated herein by reference.

"Nucleic acid probe" refers to an oligonucleotide, i.e., a DNA or RNA fragment, which binds through complementary base pairing to a subsequence of a target nucleic acid. The nucleic acid probe may be, for example, a DNA fragment prepared by amplification methods such as by PCR, or it may be synthesized by either the phosphoramidite method described by Beaucage and Carruthers (*Tetrahedron Lett.,* 22:1859–1862 (1981)) or by the triester method according to Matteucci, et al. (*J. Am. Chem. Soc.,* 103:3185 (1981)), both of which are incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific nucleic acid sequence is given, it is understood that the complementary strand is also identified and included as the complementary strand will work equally well in situations where the target is a double stranded nucleic acid.

A nucleic acid probe is complementary to a target nucleic acid when it will anneal only to a single desired position on that target nucleic acid under conditions determined as described below. Proper annealing conditions depend, for example, upon a probe's length, base composition, and the number of mismatches and their position on the probe, and must often be determined empirically. It will be understood by those of skill that minor mismatches can be accommodated by reducing the stringency of the hybridization media. For discussions of nucleic acid probe design and annealing conditions, see, e.g., Sambrook, et al., *Molecular Cloning: A Laboratory Manual* (2nd Ed., Vols. 1–3, Cold Spring Harbor Laboratory (1989)), *Methods in Enzymology,* Vol. 152: *Guide to Molecular Cloning Techniques* (Berger and Kimmel (eds.), San Diego: Academic Press, Inc. (1987)), or *Current Protocols in Molecular Biology* (Ausubel, et al. (eds.), Greene Publishing and Wiley-Interscience, New York (1987)), all of which are incorporated herein by reference.

The phrase "selectively hybridizing to" refers to a nucleic acid that hybridizes duplexes or binds only to DNA sequences encoding one protein or portions thereof when the DNA sequences encoding the protein are present in a cDNA library. A DNA sequence which selectively hybridizes to a given target sequence can include sequences which are shorter or longer than the target sequence so long as they meet the functional test set forth. Hybridization conditions are specified herein along with the source of the cDNA library. Typically, the hybridization is done in a Southern blot protocol using a 0.2×SSC, 0.1% SDS, 65° C. wash.

The term "SSC" refers to a citrate-saline solution of 0.15M sodium chloride and 15 mM sodium citrate (pH 7.0). Solutions are often expressed as multiples or fractions of this concentration. For example, 6×SSC refers to a solution having a sodium chloride and sodium citrate concentration of 6 times this amount or 0.9M sodium chloride and 90 mM sodium citrate. 0.2×SSC refers to a solution 0.2 times the SSC concentration or 0.03M sodium chloride and 3 mM sodium citrate.

The phrases "expression control sequence" or "expression control cassette" refer to nucleotide sequences which are capable of affecting expression of a structural gene in a host compatible with such sequences. Such cassettes include at least a promoter and, optionally, transcription termination signals. The term "promoter" refers to a region of DNA upstream from the structural gene and involved in the recognition and binding of a DNA polymerase and other proteins necessary to initiate transcription. Additional factors necessary or helpful in effecting expression may also be used as described herein.

The term "operably linked" refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Techniques for nucleic acid manipulation, such as subcloning nucleic acid sequences encoding polypeptides into expression vectors, labelling probes, DNA hybridization, and so on are described generally, for example, in Sambrook, et al. (1989) supra, Berger and Kimmel (1987), supra or Ausubel, et al. (1987), supra, both of which are incorporated herein by reference.

"Expression vectors," "cloning vectors" or "vectors" are often plasmids or other nucleic acid molecules that are able to replicate in a chosen host cell. Expression vectors may replicate autonomously, or they may replicate by being inserted into the genome of the host cell using methods well known in the art. Vectors that replicate autonomously will have an origin of replication or autonomous replicating sequence (ARS) that is functional in the chosen host cell(s). Often, it is desirable for a vector to be usable in more than one host cell, e.g., in E. coli for cloning and construction and in a mammalian cell for expression.

The term "plasmid" refers to an autonomous self-replicating circular DNA molecule and includes both the expression and nonexpression types. Where a recombinant microorganism or cell culture is described as hosting an "expression plasmid," this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

A "hybrid virion" is a virion comprising genome, core, and envelope components derived from more than one virus. The term specifically includes "pseudovirions" which historically have been defined as containing the genome from one virus and the structural proteins from another.

A "packaging cell" is a genetically constructed mammalian tissue culture cell that produces the necessary viral structural proteins required for packaging. The cells are incapable of producing infectious virions until a defective genome is introduced into the cells. The genetic material for the viral structural proteins is not transferred with the virions produced by the cells, hence the virus cannot replicate.

A "replication-defective" virion or retroviral vector is one produced by a packaging cell as defined above. Such a virion infects a target cell but is incapable of producing progeny virions which can infect other cells.

"Proteins," "peptides," and "polypeptides" are chains of amino acids (typically L-amino acids) whose α-carbons are linked through peptide bonds formed by a condensation reaction between the carboxyl group of the α carbon of one amino acid and the amino group of the α carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free α-amino group on the amino acid at the amino terminal of the peptide or to the α-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide or to the carboxyl group of an amino acid at any other location within the peptide.

Typically, the amino acids making up a polypeptide are numbered in order, starting at the amino terminal and increasing in the direction of the carboxy terminal of the polypeptide. Thus, when one amino acid is said to "follow" another, that amino acid is positioned closer to the carboxy terminal of the polypeptide than the "preceding" amino acid.

The term "residue" as used herein refers to an amino acid or an amino acid mimetic that is incorporated into a peptide by an amide bond or an amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides or it may be expressed as a single polypeptide from nucleic acid sequence encoding the single contiguous fusion protein. A single chain fusion protein is a fusion protein having a single contiguous polypeptide backbone.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith, et al., Adv. Appl. Math., 2:482 (1981), by the homology alignment algorithm of Needleman, et al., J. Mol. Biol., 48:443 (1970), by the search for similarity method of Pearson, et al., Proc. Natl. Acad. Sci. (U.S.A.), 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

The percentage of sequence identity between two sequences is determined by comparing two optimally aligned sequences over a window of comparison of at least 20 positions. The percentage is calculated by determining the number of positions at which the identical nucleic acid base or amino acid residue occurs in both sequences to yield the number of matched positions, dividing the number of matched positions by the total number of positions in the window of comparison (i.e., the window size), and multiplying the result by 100 to yield the percentage of sequence identity.

For instance, a preferred method for comparing sequences uses the GAP program based on the algorithm of Needleman, et al., supra. Typically, the default values for all parameters are selected. These are gap weight: 5.0; length weight: 0.30; average match: 1.0; and average mismatch: 0.0.

The term "substantial identity" means that a polynucleotide or polypeptide comprises a sequence that has at least 80% sequence identity, preferably 90%, more preferably 95% or more, compared to a reference sequence over a comparison window of about 20 bp to about 2000 bp, typically about 50 to about 1500 bp, usually about 350 bp to about 1200. The values of percent identity are determined using the GAP program, above. Another indication that nucleotide sequences are substantially identical is if two molecules hybridize to each other under stringent conditions.

The term "biologically active" refers to a peptide sequence that will interact with naturally occurring biological molecules to either activate or inhibit the function of those molecules in vitro or in vivo. The term "biologically active" is most commonly used herein to refer to the protein expressed by ERF gene that reduces or inhibits cell tumorigenicity both in vitro or in vivo.

The phrase "consisting essentially of" is used herein to exclude any elements that would substantially alter the essential properties of the VIP antagonists to which the phrase refers. Thus, the description of a polypeptide "consisting essentially of . . . " excludes any amino acid substitutions, additions, or deletions that would substantially alter the biological activity of that polypeptide.

The term "contacting" is used herein interchangeably with the following: introducing into, combined with, added to, mixed with, passed over, incubated with, injected into, flowed over, etc. Moreover, the peptides of the present invention may be "administered" by any conventional method such as, for example, parenteral, oral, topical, and inhalation routes. Moreover, the term "transfecting" is used herein to refer to the process of transferring genetic material to a cell by the addition of DNA using, fir example, a viral vector.

"An amount sufficient" or "an effective amount" is that amount of a peptide or DNA-liposome which reduces or inhibits cell tumorigenicity or, which provides either a subjective relief of a symptom(s) or an objectively identifiable improvement as noted by the clinician or other qualified observer.

As used herein, the terms "isolated," "substantially pure" and "biologically pure" are used interchangeably and describe a protein that has been separated from components which naturally accompany it. Typically, a monomeric protein is substantially pure when at least about 60% to about 75% of a sample exhibits a single polypeptide backbone. Minor variants or chemical modifications typically share the same polypeptide sequence. A substantially purified protein will typically comprise about 85% to about 90% of a protein sample, more usually about 95% and, more preferably, it will be over about 99% pure. Protein purity or homogeneity may be indicated by a number of means well known in the art, such as, for example, by polyacrylamide gel electrophoresis (PAGE) of a protein sample, followed by visualizing a single polypeptide band on a polyacrylamide gel upon staining. For certain purposes, high resolution will be needed and, thus, HPLC or other similar means can be utilized for purification in such instances.

The proteins of the present invention can be purified to substantial homogeneity by standard techniques well known in the art, including, for example, selective precipitation with such substances as ammonium sulfate, column chromatography, immunopurification methods, and other purification techniques. See, e.g., Scopes, *Protein Purification: Principles and Practice* (Springer-Verlag; New York (1982)), incorporated herein by reference.

As used herein, "immunoglobulin" refers to molecules which have specific immunoreactive activity. Antibodies are typically tetrameres of immunoglobulin molecules. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains, Heavy chain types are alpha, gamma, delta, epsilon and mu. The carboxy terminal portions of immunoglobulin heavy and light chains are constant regions, while the amino terminal portions are encoded by the myriad of immunoglobulin variable region genes. The variable regions of an immunoglobulin are the portions that provide antigen recognition specificity. The immunoglobulins may exist in a variety of forms including, for example, Fv, Fab, and F(ab)$_2$, as well as in single chains (See, e.g., Huston, et al., *Proc. Nat. Acad. Sci. U.S.A.*, 85:5879–5883 (1988) and Bird, et al., *Science*, 242:423–426 (1988), which are incorporated herein by reference). (See generally, Hood, et al., *Immunology* (Benjamin, N.Y., 2nd ed. (1984)), and Hunkapiller, et al., *Nature*, 323:15–16 (1986), which are incorporated herein by reference). Single-chain antibodies, in which genes for a heavy chain and a light chain are combined into a single coding sequence, may also be used.

DETAILED DESCRIPTION OF THE INVENTION AND PREFERRED EMBODIMENT

ERF is a novel member of the ets family of oncogenes that is a potent transcriptional repressor. ERF is the first member of the ets family to be identified as a transcriptional repressor in mammalian cells. ERF has no significant homology to the only other known repressor member of the ets family, i.e., the Drosophila gene Yan, or to other transcriptional repressors. ERF is present at constant levels in all the cell lines and tissues tested, independent of cell cycle or growth stage, indicating that it has a fundamental cellular function. It is thought that ERF regulates genes involved in cellular proliferation and that its activity is regulated by phosphorylation. The transforming ets family genes, which exhibit transactivating activity, have been associated with cell proliferation (ETS1, ETS2, Fli-1), and for some ets genes, it has been suggested that their activity is modulated by phosphorylation, either by the ras/MAPK signalling pathway (ELK1, Yan, Pointed$^{IP2}$) or during cell cycle (ETS1) and mitogenic stimulation (ETS2). The complex phosphorylation pattern of ERF during the cell cycle, its phosphorylation during mitogenic stimulation, and its inhibition by ras and src suggests that the activity of this ubiquitously-expressed transcriptional repressor is regulated by phosphorylation, which reduces its potential for repression. The fact that ERF is always phosphorylated before entry into the G1 phase of the cell cycle, either under physiological conditions or after mitogenic stimulation, indicates that the ERF gene is responsible for repressing the transcription of a subset of genes that are normally activated during entry into the G1 phase of the cell cycle.

Using the recombinant cloning techniques described herein, two related classes of human ERF cDNAs have been isolated. The first cDNA class, corresponding to SEQ ID NO: 1, encodes an ERF protein having the amino acid sequence comprising SEQ ID NO: 2. The second cDNA class, corresponding to SEQ ID NO: 3, encodes an AERF protein having the amino acid sequence comprising SEQ ID NO: 4. It has been determined that ERF is encoded by an mRNA of about 2.7 kb, whereas AERF is encoded by an mRNA of about 2.5 kb. Neither ERF nor AERF share any significant homology with any other known protein. Molecular studies indicate that the 2.7 kb and 2.5 kb mRNA species, for ERF and AERF, respectively, derive from alternative splicing of a common precursor. Further, analyses of genomic sequences indicate that the ERF and AERF are encoded by a single-copy gene. Taken together, these data suggest that the differences in structure between the two mRNA forms derive from the alternative splicing of the second exon (See, FIG. 9). It is thought that the two mRNAs use identical transcription, initiation and polyadenylylation sites.

Figure 8A:
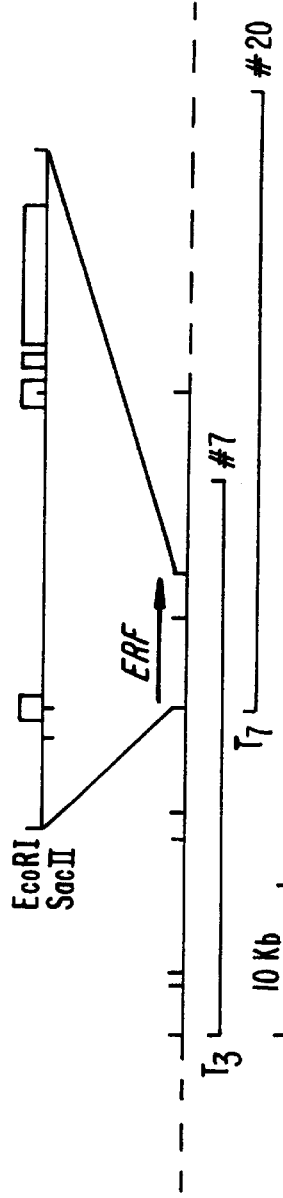
FIGS. 8A and B illustrates the genomic organization of ERF in Human and Mouse.
Figure 8B:
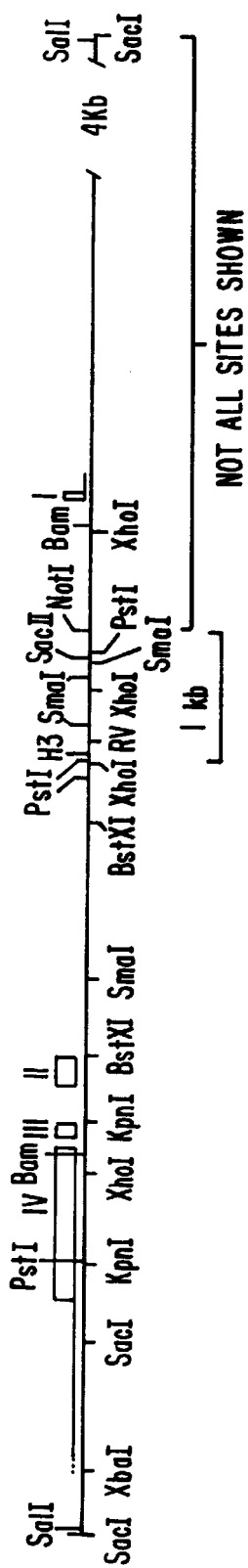

In addition, using the human clones, ERF DNA was isolated from a murine source. The mouse ERE DNA, corresponding to SEQ ID NO:6, encodes an ERF protein having the amino acid sequence comprising SEQ ID NO:7. It has been determined that the murine ERF DNA is about 98% identical to the human ERF DNA and, thus, they are substantially identical. Moreover, using the human clones, the human ERF gene has been mapped to human chromosome 19, q1.2-1.3. FIG. 8 illustrates the genomic organization of ERF in human and mouse.

In addition, the ERF promoter has been isolated and characterized (See, FIG. 10). The ERF promoter has the sequence set forth in FIG. 10 and SEQ ID NO:8. The low level constitutive expression of the ERF promoter can be used in transgenic animal studies to introduce ubiquitously expressed transgenes, but at a low level of expression. This can be very useful because it can overcome artifacts associated with the high expression levels of the currently used ubiquitous promoters (e.g., actin). Frequently, high expression levels can be toxic in transgenic animal studies.

ERF is capable of repressing the transcription of genes that contain an ets-binding site (EBS) in their regulatory region when tested in a transient expression assay, or after stable chromosomal integration of ERF and its target reporter. Many mechanisms of transcriptional repression have been described (See, Herschbach and Johnson, *Annu. Rev. Cell Biol.,* 9:479–509 (1993), for a review). Although the possibility of passive transcriptional repression mediated by the occupation of a binding site by a nontransactivating protein cannot be excluded, the data indicate that ERF contains an active repression domain located between amino acids 472 and 530, and corresponding to SEQ ID NO:5. The ERF repressor domain does not contain any recognizable features reported for other transcriptional repressors and has no homology to previously reported repressor genes. Moreover, it has been discovered that the ERF repressor domain can be effectively transferred to transcription factors having a binding domain (e.g., GAL4, NFκB (p50 and p65), MYC, Fli-1, EST1, etc.) to generate novel transcriptional repressors. FIG. 9 illustrates the general idea behind the ERF chimeric molecules of the present invention. Generally, the transactivation domain of a transcription factor is replaced with the ERF repressor domain, thereby generating ERF chimeric molecules that are transcriptional repressors. It has been found that the ERF chimeric molecules of the present invention exhibit transcription factor-specific repressor activity.

More than seven putative sites for MAP kinase and at least three cdc2 kinase phosphorylation sites can be identified within ERF, and many of these sites are phosphorylated in vitro and probably in vivo. It is not clear at this point if the Erk2 and cdc2 kinases are responsible for ERF phosphorylation in vivo. The response to serum stimulation, PMA, OAG, ionomycin and okadaic acid, as well as the hyperphosphorylation in ras- and src-transformed cells, indicates phosphorylation by MAP kinase(s) activated either through the ras pathway or the PKC pathway. Furthermore, the ability of ras and raf oncogenes to decrease the repressor function of ERF and the absence of phenotypic changes in ras- and src-transformed cells after the introduction of ERF is consistent with phosphorylation and inactivation by MAP-related kinases. In fact, ERF is an excellent substrate of Erk2 kinase, which can phosphorylate ERF at a concentration 10-fold lower than that of the in vivo levels of the kinase, and in sites that are also found phosphorylated in vivo. This data indicates that MAP-related kinases may directly phosphorylate ERF in vivo and regulate its function.

Hyperphosphorylation of ERF during mitosis is an indication of phosphorylation by cdc2 or related cdk kinases in vivo. In addition, cdc2 kinase can also readily phosphorylate ERF in vitro in sites similar to the ones that are found phosphorylated in vivo. It is not known what the function of such a phosphorylation might be. Since there is no transcription during mitosis, one plausible hypothesis consistent with $G_0/G_1$ phosphorylation is that ERF must be phosphorylated in order for the cell to enter the G1 phase. It is also possible that ERF hyperphosphorylation takes place at the late G2 phase and contributes to premitotic processes by activating some required genes. Phosphorylation by Erk2 and cdc2 can account for most of the sites found phosphorylated in vivo. Since similar sites can be found phosphorylated throughout the cell cycle, it is also possible that MAP and cdk-related kinases may also be responsible for the phosphorylation of ERF at other points during the cell cycle. The above model hypothesizing a role for ERF during $G_0/G_1$ transition and in the G2 phase would be consistent with a similar kinase activity observed at these two stages of the cell cycle.

The ERF protein is phosphorylated in vivo at multiple serine and threonine residues, and the phosphorylation level of the protein changes in response to mitogenic signals and the cell cycle stage. However, no dramatic change in the DNA-binding activity of the protein after in vitro phosphorylation by Erk2, cdc2, PKC and CAMKII kinases has been identified, indicating that the role of phosphorylation is other than regulating DNA-binding activity. The extended mobility shift observed after phosphorylation by Erk2 kinase is an indication of structural changes in the protein and it is thought that these changes may affect its interaction with other proteins. The middle part of the ERF protein contains a very high percentage of proline residues (20% in the region between the DNA-binding and repressor domains). This region has multiple putative phosphorylation sites for MAP and cdc kinases, as well as possible SH3 interaction sites (Yu, et al., *Cell,* 76:933–945 (1994)), and can be the region that regulates interactions with other proteins. Phosphorylation changes could also result in altered compartmentalization of the protein. The ERF protein is primarily found in the cytoplasmic fraction following subcellular fractionation and it is not clear at this point whether it is eluted from the nucleus during the process, or if its nuclear transport is regulated by an active mechanism. Other possible roles of phosphorylation (e.g., protein stability) cannot be excluded at this point; however, the data are consistent with the hypothesis that protein-protein interactions rather than DNA binding, nuclear localization and protein stability are affected by phosphorylation.

In view of the foregoing, the present invention provides DNA sequences encoding ERF and AERF; polypeptides encoded by such DNA sequences; ERF chimeric molecules; and methods of using ERF and ERF chimeric molecules to reduce tumorigenicity in a tumor cell.

A. General Recombinant DNA Methods

This invention relies on the use of conventional techniques and procedures in the field of recombinant genetics. Text books which describe in great detail the general methods of use in this invention are Sambrook, et al., *Molecular Cloning, A Laboratory Manual* (Cold Spring Harbor Publish., Cold Spring Harbor, N.Y., 2nd ed. (1989)); Methods in Enzymology, Vol. 152: *Guide to Molecular Cloning Techniques* (Berger and Kimmel (eds.), San Diego, Academic Press, Inc. (1987)); and Kriegler, *Gene Transfer and Expression: A Laboratory Manual* (W. H. Freeman, N.Y. (1990)), all of which are incorporated herein by reference.

B. Cloning Methods for the Isolation of Nucleic Acid Sequences Encoding The ERF And AERF Proteins The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Techniques for nucleic acid manipulation of genes encoding the ERF and AERF proteins of the invention, such as subcloning nucleic acid sequences encoding polypeptides into expression vectors, labelling probes, DNA hybridization, and the like are described generally in Sambrook, et al., supra, and Berger and Kimmel (1987), supra.

Recombinant DNA techniques can be used to produce the ERF and AERF proteins of the present invention. In general, the DNA encoding the ERF or AERF proteins is first cloned or isolated in a form suitable for ligation into an expression vector. After ligation, the vectors containing the DNA fragments or inserts are introduced into a suitable host cell for expression of the recombinant ERF and AERF proteins. The polypeptides are then isolated from the host cells.

In general, the nucleic acid sequences of the gene encoding the ERF and AERF proteins are cloned from DNA sequence libraries that are made to encode copy DNA (i.e., cDNA) or genomic DNA. The particular sequences can be located by hybridizing with an oligonucleotide probe, e.g., a probe targeting H1, an ets-binding site of the ERF2 promoter. The desired target sequences may also be obtained using polymerase chain reaction (PCR) primers which amplify either the entire gene, cDNA or portions thereof. PCR primers can be selected from the sequences provided herein. Alternatively, where the sequence is cloned into an expression library, the expressed recombinant ERF or AERF can be detected immunologically with antisera or purified antibodies made against ERF or AERF.

To make the cDNA library, one should choose a source that is rich in mRNA (e.g., placenta). The mRNA can then be made into cDNA, ligated into a recombinant vector, and transfected into a recombinant host for propagation, screening and cloning. Methods for making and screening cDNA libraries are well known. See, Gubler, et al., *Gene*, 25:263–269 (1983), Sambrook, et al., supra, and Berger and Kimmel (1987), supra.

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro, as described in Sambrook, et al., supra, and Berger and Kimmel (1987), supra Recombinant phage are analyzed by plaque hybridization as described in Benton, et al., *Science*, 196:180–182 (1977). Colony hybridization is carried out as generally described in Grunstein, et al., *Proc. Natl. Acad. Sci. USA.*, 72:3961–3965 (1975).

An alternative method combines the use of synthetic oligonucleotide primers with polymerase extension on an mRNA or DNA template. This polymerase chain reaction (PCR) method amplifies nucleic acid sequences of the ERF gene directly from mRNA, from cDNA, from genomic libraries or cDNA libraries. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of ERF mRNA in physiological samples, for nucleic acid sequencing, or for other purposes. U.S. Pat. Nos. 4,683,195 and 4,683,202 describe this method. Genes amplified by the PCR reaction can be purified from agarose gels and cloned into an appropriate vector.

Appropriate primers and probes for amplifying and identifying ERF and AERF proteins are generated from comparisons of the sequences provided herein. In brief, oligonucleotide primers are complementary to the borders of the DNA region to be amplified are synthesized. The polymerase chain reaction is then carried out using these two primers. For a general overview of PCR, see, e.g., *PCR Protocols: A Guide to Methods and Applications* (Innis, Gelfand, Sninsky and White, eds.), Academic Press, San Diego (1990), incorporated herein by reference.

Oligonucleotides that are useful as probes can be chemically synthesized according to the solid phase phosphoramidite triester method first described by Beaucage, et al., *Tetrahedron Letts.*, 22(20):1859–1862 (1981) using an automated synthesizer, as described in Van Devanter, et al., *Nucleic Acids Res.* 12:6159–6168 (1984). Purification of oligonucleotides is by either native acrylamide gel electrophoresis or by anion-exchange HPLC as described by Pearson and Reanier, *J. Chrom.*, 255:137–149 (1983).

The sequences of the cloned gene and synthetic oligonucleotides can be verified using the chemical degradation method of Maxam, et al., *Methods in Enzymology*, 65:499–560 (1980). The sequence can be confirmed after the assembly of the oligonucleotide fragments into the double-stranded DNA sequence using the method of Maxam and Gilbert, supra, or the chain termination method for sequencing double-stranded templates of Wallace, et al., *Gene*, 16:21–26 (1981). Southern Blot hybridization techniques are carried out according to Southern, et al., *J. Mol. Biol.*, 98:503 (1975).

Synthetic oligonucleotides can also be used to construct genes. This is done using a series of overlapping oligonucleotides usually 40–120 bp in length, representing both the sense and nonsense strands of the gene. These DNA fragments are then annealed, ligated and cloned.

Moreover, the gene, i.e., polynucleotides, encoding the ERF and AERF proteins can be cloned using intermediate vectors before transformation into mammalian cells for expression. These intermediate vectors are typically prokaryote vectors or shuttle vectors. The ERF and AERF proteins can be expressed in either prokaryotes or eukaryotes.

In summary, the ERF gene can be prepared by probing or amplifying select regions of a mixed cDNA or genomic pool using the probes and primers generated from the sequences provided herein.

C. Expression of ERF and AERF Polypeptides

Once the polynucleotides encoding the ERF and AERF proteins are isolated and cloned, one may express the desired proteins in a recombinantly engineered cell, such as bacteria, yeast, insect (especially employing baculoviral vectors) and mammalian cells. It is expected that those of skill in the art are knowledgeable in the numerous expression systems available for expression of the DNA encoding the ERF and AERF proteins. No attempt to describe in detail the various methods known for the expression of proteins in prokaryotes or eukaryotes will be made.

In brief summary, the expression of natural or synthetic nucleic acids encoding the ERF and AERF proteins will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the ERF and AERF proteins. To obtain high level expression of a cloned gene, it is desirable to construct expression plasmids which contain, at the minimum, a strong promoter to direct transcription, a ribosome binding site for translational initiation, and a transcription/translation terminator.

1. Expression in Prokaryotes

Examples of regulatory regions suitable for this purpose in *E. coli* are the promoter and operator region of the *E. coli* tryptophan biosynthetic pathway as described by Yanofsky, *Bacteriol.*, 158:1018–1024 (1984), and the leftward promoter of phage lambda ($P_L$) as described by Herskowitz, et al., *Ann. Rev. Genet.*, 14:399–445 (1980). The inclusion of selection markers in DNA vectors transformed in *E. coli* is also useful. Examples of such markers include genes specifying resistance to ampicillin, tetracycline or chloramphenicol. See, Sambrook, et al., supra for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA.

Expression systems for expressing the ERF and AERF proteins are available using *E. coli, Bacillus sp.* and Salmonella (Palva, et al., *Gene*, 22:229–235 (1983); Mosbach, et al., *Nature*, 302:543–545 (1983)). *E. coli* systems are presently preferred.

The ERF and AERF proteins produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl, and reducing all the cysteine residues with a reducing agent such as beta-mercaptoethanol. The polypeptides are then renatured, either by slow dialysis or by gel filtration (see U.S. Pat. No. 4,511,503).

When expressing the ERF and AERF proteins in *S. typhimurium*, one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the *S. typhimurium*, the foreign gene is incorporated into the chromosome by homologous recombination between the flanking sequences and chromosomal DNA.

An example of how this can be achieved is based on the his operon of Salmonella. Two steps are involved in this process. First, a segment of the his operon must be deleted in the Salmonella strain selected as the carrier. Second, a plasmid carrying the deleted his region downstream of the gene encoding the ERF and AERF proteins is transformed into the his Salmonella strain. Integration of both the his sequences and a gene encoding an ERF protein occurs, resulting in recombinant strains which can be selected as his$^+$.

Detection of the expressed protein is achieved by methods known in the art and include, for example, radioimmunoassays, Western blotting techniques or immunoprecipitation. Purification from *E. coli* can be achieved following procedures described in U.S. Pat. No. 4,511,503.

2. Expression in Eukaryotes.

Standard eukaryotic transfection methods are used to produce mammalian, yeast or insect cell lines which express large quantities of the ERF and AERF proteins which are then purified using standard techniques. See, e.g., Colley, et al., *J. Biol. Chem.* 264:17619–17622 (1989), and "Guide to Protein Purification," in Vol. 182 of *Methods in Enzymology (Deutscher (ed.),* 1990), both of which are incorporated herein by reference.

Transformations of eukaryotic cells are performed according to standard techniques as described by Morrison, *J. Bact.*, 132:349–351 (1977), or by Clark-Curtiss, et al., *Methods in Enzymology*, 101:347–362 (Wu, et. al., (eds.)), Academic Press, New York (1983).

Any of the well known procedures for introducing foreign nucleotide sequences into host cells can be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (See, Sambrook, et al., supra). It is only necessary that the particular genetic engineering procedure utilized be capable of successfully introducing at least one gene into the host cell which is capable of expressing an ERF or AERF protein.

The particular eukaryotic expression vector used to transport the genetic information into the cell is not particularly critical. Any of the conventional vectors used for expression in eukaryotic cells can be used. Expression vectors containing regulatory elements from eukaryotic viruses are typically used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A$^+$, pMTO10/A$^+$, pMAMneo-5, bacculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The vectors usually comprise selectable markers which result in gene amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving gene amplification are also suitable, such as using a bacculovirus vector in insect cells, with the ERF or AERF encoding sequence under the direction of the polyhedrin promoter or other strong baculovirus promoters.

The expression vector of the present invention will typically contain both prokaryotic sequences that facilitate the cloning of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired gene. The expression vector is typically constructed from elements derived from different, well characterized viral or mammalian genes. For a general discussion of the expression of cloned genes in cultured mammalian cells, see, Sambrook, et al., supra, Ch. 16.

The prokaryotic elements that are typically included in the mammalian expression vector include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells.

The expression vector contains a eukaryotic transcription unit or expression cassette that contains all the elements required for the expression of an ERF or AERF protein in eukaryotic cells. A typical expression cassette contains a promoter operably linked to the DNA sequence encoding an ERF or an AERF protein and signals required for efficient polyadenylation of the transcript. The DNA sequence encoding the ERF or AERF protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression* (Cold Spring Harbor Pres, Cold Spring Harbor, N.Y. 1983), which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence, or it may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site, and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned genes, or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

After the expression vector is introduced into the cells, the transfected cells are cultured under conditions favoring expression of the ERF or AERF protein which is recovered from the culture using standard techniques a. Expression in Yeast Synthesis of heterologous proteins in yeast is well known and described. Sherman, et al., *Methods in Yeast Genetics*, Cold Spring Harbor Laboratory (1982) is a well recognized work describing the various methods available to produce an ERF or AERF protein in yeast.

For high level expression of a gene in yeast, it is essential to connect the gene to a strong promoter system and to provide efficient transcription termination/polyadenylation sequences from a yeast gene. Examples of useful promoters include GAL1,10 (Johnson, et al., *Mol. and Cell. Biol.,* 4:1440–1448 (1984)) ADH2 (Russell, et al., *J. Biol. Chem.,* 258:2674–2682, (1983)), PHO5 (*EMBO J.* 6:675–680, (1982)), and MFα1 (Herskowitz, et al., *The Molecular Biology of the Yeast Saccharomyces,* (Strathern, Jones and Broach, eds.), Cold Spring Harbor Lab., Cold Spring Harbor, N.Y., pp.181–209, (1982)). A multicopy plasmid with a selective marker such as, for example, Leu-2, URA-3, Trp-1, and His-3 is also desirable.

The MFα1 promoter is preferred. The MFα1 promoter, in a host of the a mating-type is constitutive, but is switched off in diploids or cells with the a mating-type. It can, however, be regulated by raising or lowering the temperature in hosts which have a ts mutation at one of the SIR loci. The effect of such a mutation at 35° C. on an α type cell is to turn on the normally silent gene coding for the α mating-type. The expression of the silent a mating-type gene, in turn, turns off the MFα1 promoter. Lowering the temperature of growth to 27° C. reverses the whole process, i.e., turns the a mating-type off and turns the MFα1 on (Herskowitz and Oshima, supra).

The polyadenylation sequences are provided by the 3'-end sequences of any of the highly expressed genes, like ADH1, MFα1, or TPI (Alber, et al., *J. Mol. & Appl. Genet.,* 1:419–434 (1982)).

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., *Gene* 8:17–24 (1979); Broach, et al., *Gene* 8:121–133 (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by Beggs, *Nature,* 275:104–109 (1978); and Hinnen, et al., *Proc. Natl. Acad. Sci. USA,* 75:1929–1933 (1978). The second procedure does not involve removal of the cell wall. Instead the cells are treated with lithium chloride or acetate and PEG and put on selective plates (Ito, et al., *J. Bact.* 153:163–168 (1983)).

Soluble ERF and AERF proteins can be isolated from yeast by lysing the cells and applying standard protein isolation techniques to the lysates. The monitoring of the purification process can be accomplished by using Western blot techniques or other standard radioimmunoassays.

b. Expression in insect cells

The baculovirus expression vector utilizes the highly expressed and regulated *Autographa californica* nuclear polyhedrosis virus (AcMNPV) polyhedrin promoter modified for the insertion of foreign genes. Synthesis of polyhedrin protein results in the formation of occlusion bodies in the infected insect cell. The recombinant proteins expressed using this vector have been found in many cases to be, antigenically, immunogenically and functionally similar to their natural counterparts. In addition, the baculovirus vector utilizes many of the protein modification, processing and transport systems that occur in higher eukaryotic cells.

Briefly, the DNA sequence encoding an ERF or AERF protein is inserted into a transfer plasmid vector in the proper orientation downstream from the polyhedrin promoter, and flanked on both ends with baculovirus sequences. Cultured insect cell, commonly *Spodoptera frugiperda,* are transfected with a mixture of viral and plasmid DNAs. The virus that develop, some of which are recombinant virus that result from homologous recombination between the two DNAs, are plated at 100–1000 plaques per plate. The plaques containing recombinant virus can be identified visually because of their ability to form occlusion bodies or by DNA hybridization. The recombinant virus is isolated by plaque purification. The resulting recombinant virus, capable of expressing an ERF or AERF protein, is self-propagating in that no helper virus is required for maintenance or replication. After infecting an insect culture with recombinant virus, one can expect to find recombinant protein within 48–72 hours. The infection is essentially lytic within 4–5 days.

There are a variety of transfer vectors into which an ERF gene can be inserted. For a summary of transfer vectors, see, Luckow, et al., *Bio/Technology,* 6:47–55 (1988). Preferred is the transfer vector pAcUW21 described by Bishop in *Seminars in Virology,* 3:253–264 (1992).

c. Expression in recombinant vaccinia virus-infected cells or adenovirus-infected cells In addition to their use in recombinant expression systems, the isolated DNA sequences encoding the ERF and AERF proteins can also be used to transform viruses that transfect host cells in the patient. Live attenuated viruses, such as vaccinia or adenovirus, are convenient alternatives for vaccines because they are inexpensive to produce and are easily transported and administered. Vaccinia vectors and methods useful in immunization protocols are described, for example, in U.S. Pat. No. 4,722,848, incorporated herein by reference.

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA encoding the ERF and AERF polypeptides into plasmids so that they are flanked by viral sequences on both sides. The DNA encoding the ERF and AERF proteins are then inserted into the virus genome through homologous recombination.

A recombinant adenovirus can be produced, for example, by ligating together two plasmids each containing about 50% of the viral sequence and the DNA sequence encoding an ERF or an AERF polypeptide. Recombinant RNA viruses such as the alpha virus can be made via a CDNA intermediate using methods known in the art.

In the case of vaccinia virus (for example, strain WR), the DNA sequence encoding the ERF and AERF proteins can be inserted in the genome by a number of methods including homologous recombination using a transfer vector, pTKgpt-OFIS as described in Kaslow, et al., *Science,* 252:1310–1313 (1991), which is incorporated herein by reference.

Alternately, the DNA encoding the ERF or AERF protein may be inserted into another plasmid designed for producing recombinant vaccinia, such as pGS62 (Langford, et al., *Mol. Cell. Biol.,* 6:3191–3199 (1986)). This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using cDNA encoding the ERF or AERF polypeptides and by immunodetection techniques using antibodies specific for the expressed ERF or AERF polypeptides. Virus stocks may be prepared by infection of cells such as HELA S3 spinner cells and harvesting of virus progeny.

The recombinant virus of the present invention can be used to induce anti-ERF or anti-AERF antibodies in mammals, such as mice or humans. In addition, the recombinant virus can be used to produce ERF or AERF by infecting host cells in vitro which, in turn, express the polypeptide (see, section on expression of ERF and AERF in eukaryotic cells, supra).

The present invention also relates to host cells infected with the recombinant virus. The host cells of the present invention are preferably mammalian, such as BSC-1 cells. Host cells infected with the recombinant virus express the ERF and AERF proteins on their cell surfaces. In addition, membrane extracts of the infected cells induce protective antibodies when used to inoculate or boost previously inoculated mammals.

3. Expression in Cell Cultures

ERF cDNA can be ligated to various expression vectors for use in transforming host cell cultures. The vectors typically contain gene sequences to initiate transcription and translation of the ERF gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

Cells of mammalian origin are illustrative of cell cultures useful for the production of the ERF and AERF proteins. Mammalian cell systems often will be in the form of monolayers of cells although mammalian cell suspensions may also be used. Illustrative examples of mammalian cell lines include, for example, VERO and HeLa cells, Chinese hamster ovary (CHO) cell lines, WI38, BHK, COS-7 or MDCK cell lines.

As indicated above, the vector, i.e., a plasmid, which is used to transform the host cell, preferably contains DNA sequences to initiate transcription and sequences to control the translation of the ERF gene sequence. These sequences are referred to as expression control sequences. Illustrative expression control sequences are obtained from the SV-40 promoter (*Science,* 222:524–527 (1983)), the CMV I. E. Promoter (*Proc. Natl. Acad. Sci. USA.,* 81:659–663 (1984)) or the metallothionein promoter (*Nature* 296:39–42 (1982)). The cloning vector containing the expression control sequences is cleaved using restriction enzymes and adjusted in size as necessary or desirable and ligated with sequences encoding the ERF or AERF protein by means well known in the art. As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.,* 45:773–781 (1983)).

Additionally, gene sequences to control replication in the host cell may be incorporated into the vector such as those found in bovine papilloma virus type-vectors. See, e.g., Saveria-Campo, "*Bovine Papilloma virus DNA a Eukaryotic Cloning Vector*" in *DNA Cloning, Vol.* 11, A Practical Approach (D. M. Glover, Ed., IRL Press, Arlington, Va., pp. 213–238 (1985)).

The transformed cells are cultured by means well known in the art. For example, as published in *Biochemical Methods in Cell Culture and Virology* (Kuchler, Dowden, Hutchinson and Ross, Inc. (1977)). The expressed ERF or AERF protein is isolated from cells grown as suspensions or as monolayers. The latter are recovered by well known mechanical, chemical or enzymatic means.

4. Expression Using A Retroviral Vector

Retroviral vectors are particularly useful for directing desired polynucleotides to the appropriate cells and for integration of the polynucleotides in the host cell genome (See, Friedman, *Science,* 24:1275–1281 (1989); Miller, *Human Gene Therapy,* 1:15–19 (1990); Verma, *Scientific America* (November 1990); and Mulligan, *Science,* 260:926–931 (1993), the teachings of which are incorporated herein by reference.) Briefly, a mammal having a tumor cell is inoculated with a cell line that produces a retroviral vector that contains the ERF gene. Typically, the cell line has been treated so that it replicates only for a short time, several days for example. Cells so treated are referred to as "mortalized." Irradiation, for example, is a convenient mortalization treatment. Thus, although the cell line has been mortalized, it is capable of producing the engineered retrovirus for about 4 to 8 days. The defective-retrovirus can invade and transfect cells, but it cannot undergo further virus production. The mortalized cells carry the retrovirus which serves as a vehicle for carrying a gene of interest into the cell, e.g., a tumor cell.

More particularly, replication-defective retroviral vectors are produced when a defective DNA viral genome is introduced into a packaging cell line. The defective genome contains the sequences required for integration into the target cell genome, for packaging of the genome into infectious virions, as well as those viral sequences required for expression of the therapeutic gene or other polynucleotide contained within the defective viral genome. The packaging cells comprise the gag, pol, and env genes which encode the viral core and envelope components. These core and envelope proteins assemble around the defective genome, thus producing retroviral vectors.

A number of standard techniques are used to ensure safety of retroviral vectors. For instance, the defective genome is introduced into the cell separately from the genes encoding the core and envelope components. In this way, recombination between the genome and the core and envelope genes, which would lead to the packaging of complete viral genomes, is extremely unlikely. The resulting virions should therefore not comprise the gag, pol, and env genes and are thus replication-defective. Homologous recombination, however, between the inserts can lead to the production of infectious virions. Typically, the packaging cells are produced by introducing the gag, pol, and env genes on at least two separate plasmids. This scheme effectively prevents homologous recombination leading to reconstruction of infectious virus because the probability of multiple, independent homologous recombination events occurring is extremely low.

Retroviral vectors can also be designed to prevent synthesis of viral proteins by the integrated defective genome. For instance, if a portion of the gag gene is included to increase packaging efficiency, a stop codon can be introduced into the gene to prevent synthesis of gag proteins. Miller, et al., *BioTechniques,* 7:982–988 (1989), which is incorporated herein by reference.

5. Expression Using Direct Gene Transfer

In addition to the foregoing methods, the ERF gene can be directly introduced into the cells or tissue of interest using techniques known to those of skill in the art. The ERF gene can, for example, be directly introduced into the cells or tissue of interest using a DNA-liposome complex. Plasmid ERF DNA complexed to liposomes can be used to transfer genes by injection or catheter into cells or tissue where they stimulate localized biological responses. Briefly, the expression vector plasmid is produced using the procedures and techniques described supra. Once the plasmid is grown and purified, the plasmid-liposome complex is formed by, for example, incubating the plasmid in lactated Ringer's solution (see, infra, for a detailed discussion regarding liposomes). The DNA-liposome complex is subsequently introduced into the cells or tissue of interest by injection or catheter. For a detailed review of the use of this technique, see, e.g., Nabel, et al., *Proc. Natl. Acad. Sci. USA,* 90:11307–11311 (1993) and the references cited therein, the teachings of which are hereby incorporated by reference.

D. Purification of the ERF and AERF Proteins

The ERF and AERF proteins of the present invention can be substantially purified using conventional techniques known to and used by those of skill in the art including, for example, selective precipitation with such substances as ammonium sulfate, column chromatography, immunopurification methods, and other purification techniques. See, e.g., Scopes, *Protein Purification: Principles and Practice* (Springer-Verlag: New York (1982)).

E. Detection of the ERF Gene and ERF and AERF Proteins.

1. ERF DNA and RNA Measurement

The present invention also provides methods for detecting the presence or absence of ERF DNA or RNA in a biological sample. A variety of methods of specific DNA and RNA measurement using nucleic acid hybridization techniques are known to those of skill in the art. See, e.g., Sambrook, et al., supra. and Berger and Kimmel, (1987), supra. For example, one method for evaluating the presence or absence of ERF DNA in a sample involves a Southern transfer. Briefly, the digested genomic DNA is run on agarose slab gels in buffer and transferred to membranes. Hybridization is carried out using probes and visualization of the hybridized portions allows the qualitative determination of the presence or absence of the ERF gene.

Similarly, a Northern transfer may be used for the detection of ERF mRNA in samples of RNA. In brief, the mRNA is isolated from a given cell sample (e.g., HeLa cells) using an SDS-phenol or acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of an ERF transcript.

A variety of nucleic acid hybridization formats are known to those skilled in the art. For example, common formats include sandwich assays and competition or displacement assays. Hybridization techniques are generally described in Berger and Kimmel (1987), supra.; "*Nucleic Acid Hybridization, A Practical Approach*" (Hames, B. D. and Higgins, S. J. (eds.), IRL Press (1985); Gall, et al., *Proc. Natl. Acad. Sci. U.S.A.,* 63:378–383 (1969); and John, et al., *Nature,* 223:582–587 (1969).

For example, sandwich assays are commercially useful hybridization assays for detecting or isolating nucleic acid sequences. Such assays utilize a "capture" nucleic acid covalently immobilized to a solid support and a labelled "signal" nucleic acid in solution. The clinical sample will provide the target nucleic acid. The "capture" nucleic acid probe and the "signal" nucleic acid probe hybridize with the target nucleic acid to form a "sandwich" hybridization complex. To be effective, the signal nucleic acid cannot hybridize with the capture nucleic acid.

Typically, labelled signal nucleic acids are used to detect hybridization. Complementary nucleic acids or signal nucleic acids may be labelled by any one of several methods typically used to detect the presence of hybridized oligonucleotides. The most common method of detection is the use of autoradiography with $^3$H, $^{125}$I, $^{35}$S, $^{14}$C, or $^{32}$P-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe oligonucleotides or nucleic acids. Typically, such binding occurs through ligand and anti-ligand interactions as between a ligand-conjugated probe and an anti-ligand conjugated with a signal. The binding of the signal generation complex is also readily amendable to accelerations by exposure to ultrasonic energy.

The label may also allow for the indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, "Practice and Theory of Enzyme Immunoassays," *Laboratory Techniques in Biochemistry and Molecular Biology*" (Burdon, van Knippenberg (eds.), Elsevier, pp. 9–20 (1985).)

The sensitivity of the hybridization assays may be enhanced through the use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q-Beta Replicase systems.

An alternative means for determining the level of expression of the ERF gene is in situ hybridization. In an in situ hybridization assay cells are fixed to a solid support, typically a glass slide. If DNA is to be probed, the cells are denatured with heat or alkali. The cells are then contacted with a hybridization solution at a moderate temperature to permit annealing of ERF-specific probes that are labelled. The probes are preferably labelled with radioisotopes or fluorescent reporters. In situ hybridization assays are well known and are generally described by Angerer, et al., *Methods Enzymol.* 152:649–660 (1987).

2. Measurement of ERF and AERF Proteins and Antibodies to ERF and AERF

In addition to the detection of the ERF gene or the ERF gene expressions using nucleic acid hybridization technology, one can use immunoassays to detect either the products of the ERF gene or the presence of antibodies to ERF and AERF. Immunoassays can be used to qualitatively or quantitatively analyze ERF and AERF proteins or, alternatively, ERF and AERF antibodies. A general overview of the applicable technology can be found in Harlow and Lane, *Antibodies: A Laboratory Manual* (Cold Spring Harbor Pubs., N.Y. (1988)), incorporated herein by reference.

A number of immunogens may be used to produce antibodies specifically reactive with the ERF or AERF antigen. Recombinant ERF and AERF proteins are the preferred immunogens for the production of monoclonal or polyclonal antibodies. Naturally occurring ERF and AERF proteins may also be used either in pure or impure form. Synthetic peptides made using the ERF and AERF protein sequences described herein may also be used as an immunogen for the production of antibodies to the ERF proteins.

Preferentially, recombinant ERF or AERF protein or, a fragment thereof, is expressed in bacterial cells as described above, and purified as generally described above and in the examples. The product is then injected into an animal capable of producing antibodies. Either monoclonal or polyclonal antibodies may be generated for subsequent use in immunoassays to measure the ERF and AERF proteins.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the ERF or AERF proteins. When appropriately high titers of antibody to the immunogen are obtained, blood is collected from the animal and antisera is prepared. Further fractionation of the antisera to enrich for antibodies reactive to the ERF or AERF proteins can be done if desired. (See, Harlow and Lane, supra.)

Monoclonal antibodies can be obtained by various techniques familiar to those skilled in the art. Briefly, spleen cells from an animal immunized with a desired antigen are immortalized, commonly by fusion with a myeloma cell (See, e.g., Kohler, et al., *Eur. J. Immunol.*, 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Either monoclonal or polyclonal antibodies specific for the gene product can be used in various immunoassays. Such assays include, for example, ELISA, competitive immunoassays, radioimmunoassays, Western blots, indirect immunofluorescent assays and the like.

F. ERF Chimeric Molecules

In another aspect of the present invention, ERF chimeric molecules are provided, the ERF chimeric molecules comprising an ERF repressor domain attached to a transcription factor having a binding site. It has been discovered that ERF contains an active repression domain located between amino acids 472 and 530 (See, SEQ ID NO: 5). The ERF repressor domain does not contain any recognizable features reported for other transcriptional repressors and has no homology to previously reported repressor genes (Han, K., et al., *Genes Dev.* 7, 491–503 (1993); Jaynes, J. D., et al., *EMBO J.* 10, 1427–1433 (1991); Licht, J. D., et al., *Nature* 346, 76–79 (1990); Cowell, I. G., et al., *Nucleic Acids Res.* 22, 59–65 (1994); Madden, S. L., et al., *Oncogene* 8, 1713–1720 (1993); and Baniahmad, A., et al., *EMBO J.* 11, 1015–1023 (1992)). It has further been discovered that the ERF repressor domain can be effectively transferred to transcription factors having a binding domain, e.g., GAL4, to generate novel transcriptional repressors.

Figure 15:
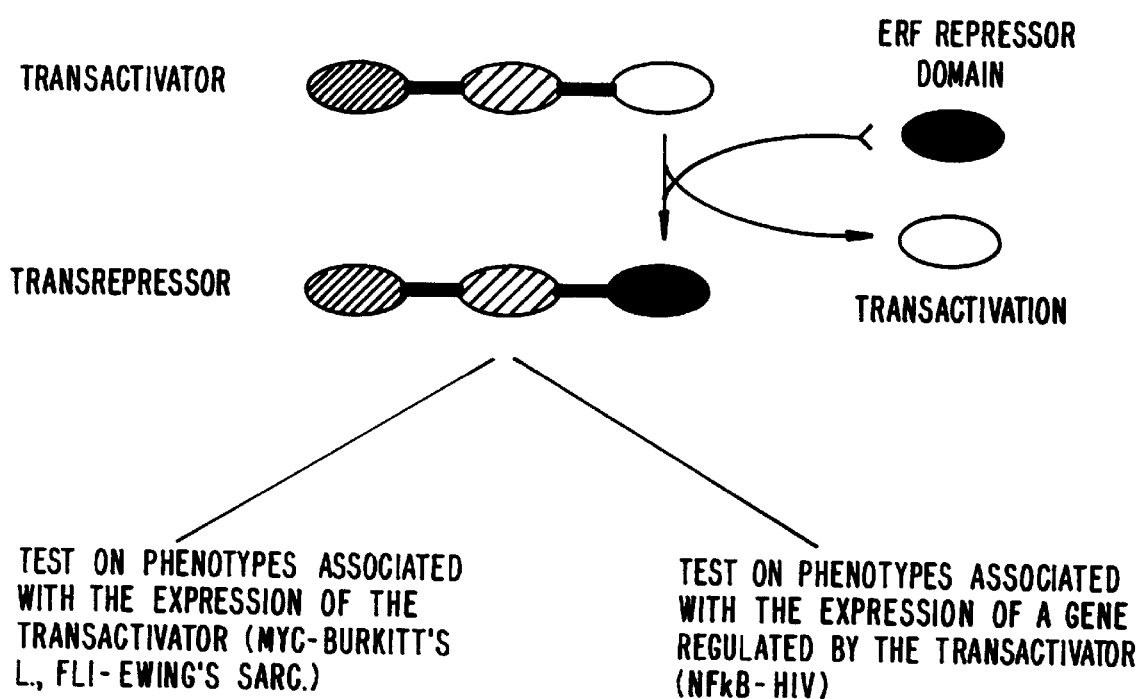
FIG. 15 illustrates the general strategy behind the ERF chimeric molecules of the present invention.

FIG. 15 illustrates the general idea behind the ERF chimeric molecules of the present invention. Generally, the transactivation domain of a transcription factor is replaced with the ERF repressor domain, thereby generating ERF chimeric molecules that are transcriptional repressors. It has been found that the ERF chimeric molecules of the present invention exhibit transcription factor-specific repressor activity. Transcription factors which can be used to form the ERF chimeric molecules of the present invention include, but are not limited to, the following: GAL4, NFκB (p50 and p65), MYC, Fli-1 and EST1. Such transcription factors have been well-characterized and, thus, one of skill will be able to determine the location and amino acid sequences of both the binding and transactivation domains. See, Papavassiliou, A. G., *Moleuclar Medicine* 332:45–47 (1995); and Seth and Papas, *Cancer. Principles and Practice of Oncology* 1:23–34 (V. DeVita, Jr., S. Hellman and S. A. Rosenberg (eds.), J. B. Lippincott Co., 4th Edition (1993), for a general review of transcription factors. See, Hromas, R. and M. Klems, *Int. J. Hematol.* 59(4):257–65 (1994); and Wasylyk, B., et al., *Eur. J. Biochem.* 211(1–2): 7–18 (1993), for a general review of Fli-1. See, Borrow, J. and E. Solomon, *Baillieres Clin. Haematol.* 5(4):833–56 (1992), Braithwaite, A. W., et al., *New Biol.* 3(1):18–26 (1991), for a review of GAL4. See, Sienbenlist, U., et al., *Annu. Rev. Cell. Biol.* 10:405–55 (1994); Swingler, S., et al., *Biochem. Biophys. Res. Commun.* 203(1):623–30 (1994); Himes. et al., *Oncogene* 8(12):3189–97 (1993), for a review of NFκB. See, Evan, G., et al., *Philos. Trans. R. Soc. B. Biol. Sci.* 345 (1313):269–275 (1994); Vastrik, I., et al., *Crit. Rev. Oncog.* 5(1):59–68 (1994); Koskinen, P. J., et al., *Clin. Chem. Acta.* 217(1):57–62 (1993); and Kato, G., et al., *Cancer Treat. Res.* 63:313–25 (1992), for a review of MYC. See, Watson, et al., *Proc. Natl. Acad. Sci. U.S.A.* 82:7294–7298 (1985); and Watson, et al., *Proc. Natl. Acad. Sci. U.S.A.* 83:1792–1796 (1986), for a review of ETS1. All of the aforementioned references are hereby incorporated by reference in their entirety.

The ERF chimeric molecules of the present invention can be used to suppress, i.e., reduce, tumorigenicity associated with the inappropriate expression of a transcription activator. "Inappropriate expression," as used herein, refers to the abnormal, i.e., aberrant, expression of a transcription factor. The abnormal expression can involve the overexpression of a transcription factor or, alternatively, it can involve the underexpression of a transcription factor. Typically, the inappropriate expression of the transcription factor will involve the overexpression of the factor which, in turn, induces uncontrolled cell proliferation. Progressive, uncontrolled cell division will, if the progeny cells remain localized (at least initially), result in the formation of an abnormal growth (i.e., a tumor or neoplasm). The abnormal growth can be malignant or benign.

Figure 11:
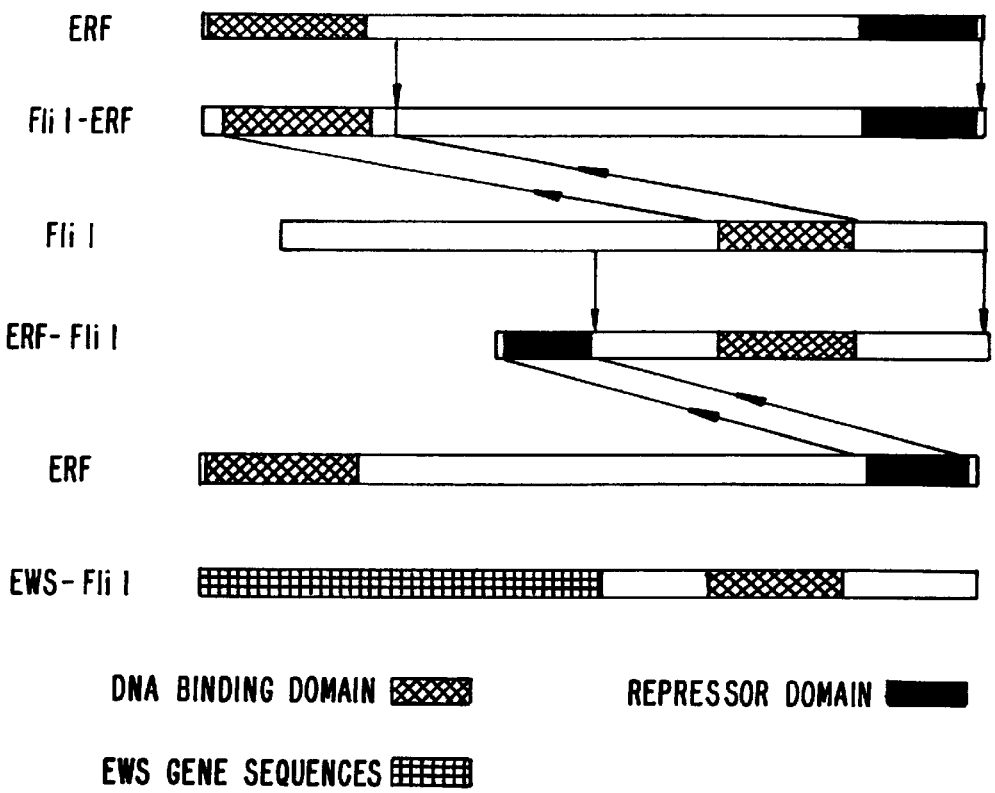
FIG. 11 illustrates the Fli1-ERF hybrids which can be used to suppress the Ewing's Sarcoma phenotype.
Figure 13:
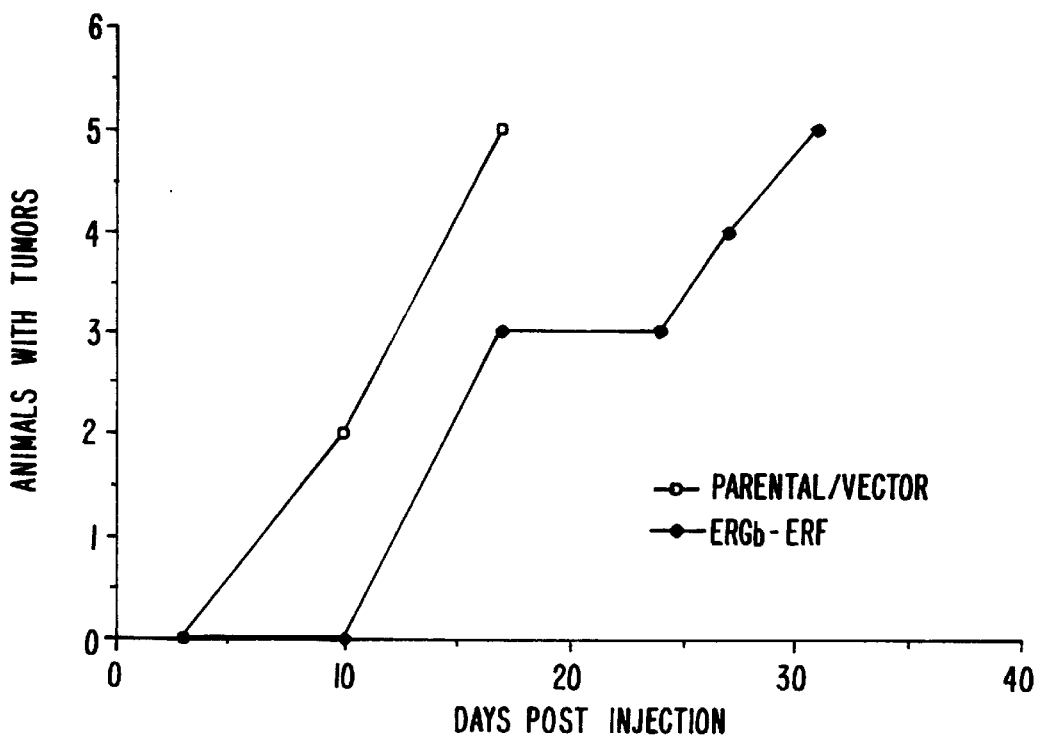
FIG. 13 illustrates the delay of tumor development in nude mice by Ewing's Sarcoma cell lines (ATCC-HTB86) expressing the Fli1-ERF hybrids.
Figure 12A:
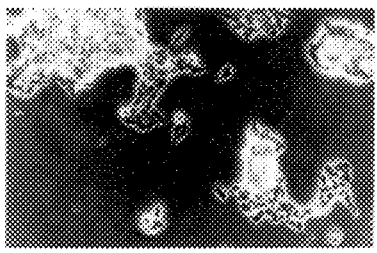
FIGS. 12A–E illustrates the morphological differences of Ewing's Sarcoma cell lines (ATCC-HTB166) induced by the expression of the Fli1-ERF hybrid, introduced using a retrovirus.
Figure 12B:
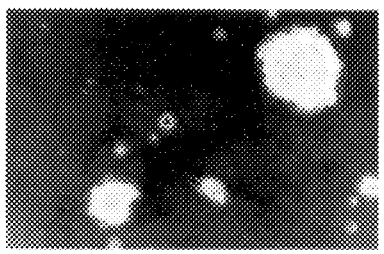
Figure 12C:
Figure 12D:
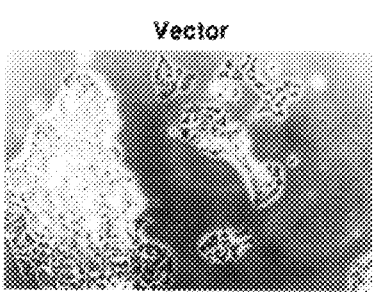
Figure 12E:
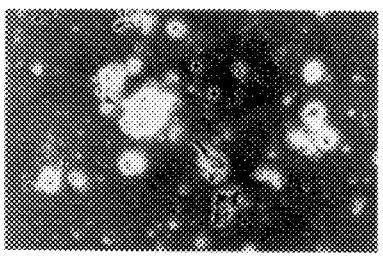
Figure 14:
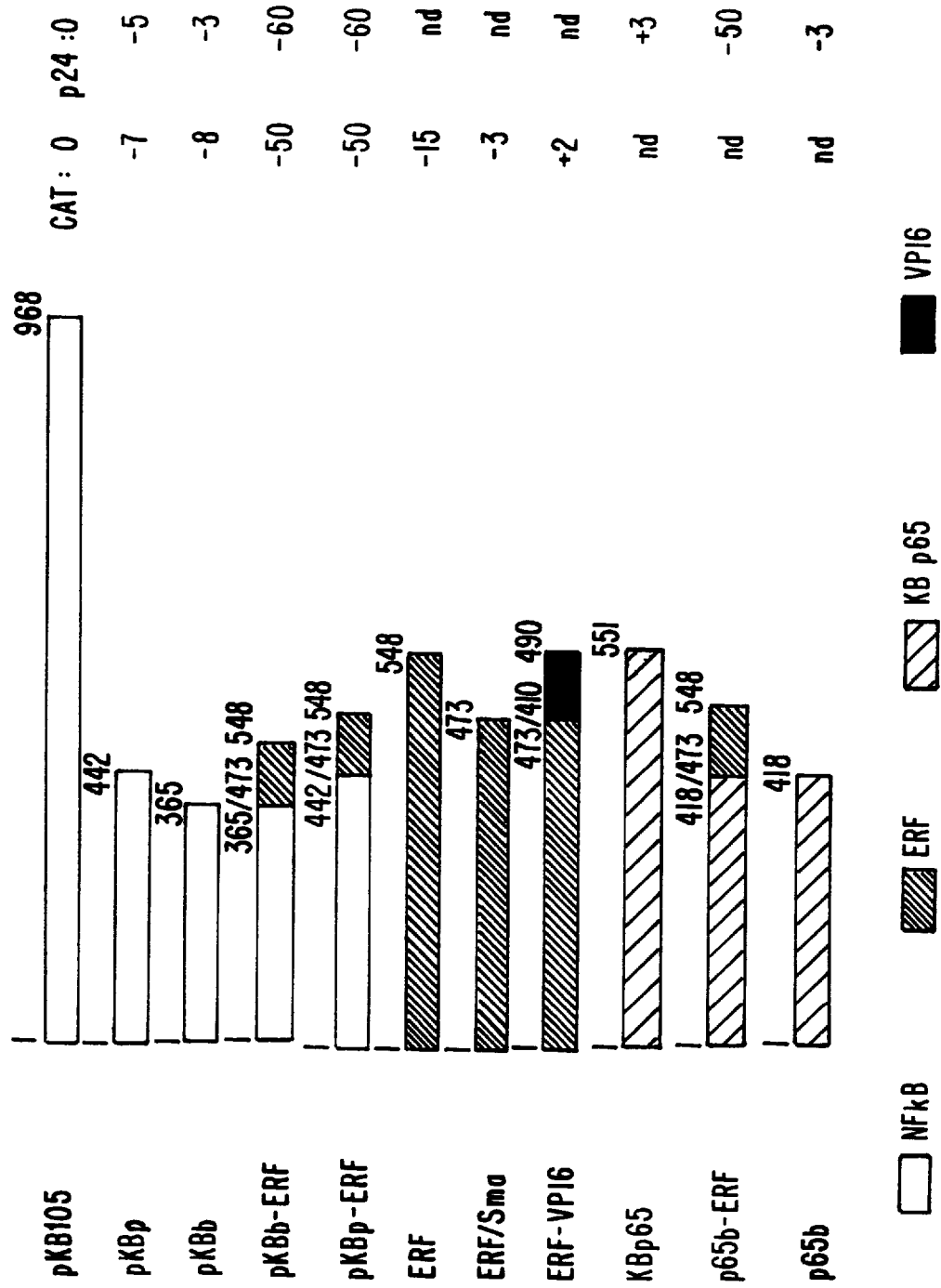
FIG. 14 illustrates that ERF-NFκB hybrids can be used to suppress HIV-LTR transcription in transient transfections as determined by CAT assays and HIV live virus production as determined by the production of the p24 viral protein, after the infection of ERF-κB producing cells with competent HIV virus (HXB2 strain).

The ERF chimeric molecules can be used, for example, to suppress malignant phenotypes associated with Ewing's Sarcoma (ERF-Fli-1), Burkitt Lymphoma (ERF-MYC), HIV (ERF-NFκB) and other malignant phenotypes associated with the aberrant activation of a transcriptional activator. For example, ERF-Fli-1 chimeric molecules, illustrated in FIG. 11, can be used to suppress the phenotype associated with Ewing's sarcoma. In fact, FIG. 12 depicts the morphological differences of Ewing's Sarcoma cell lines (ATCC-HTB166) induced by the expression of an ERF-Fli-1 chemical molecule, introduced by a retrovirus using a method similar to that set forth in the examples. In addition, FIG. 13 graphically depicts the delay of tumor development in nude mice by Ewing's Sarcoma cell lines (ATCC-HTB86) expressing an ERF-Fli-1 chimeric molecule. Moreover, as illustrated in FIG. 14, ERF-NFκB chimeric molecules can be used to suppress HIV-LTR transcription in transient transfections as determined by CAT assays and HIV live virus production measured by determining the production of the p24 viral protein after the infection of ERF-NFκB producing cell lines with competent HIV virus (HXB2 strain). As with the ERF-Fli-1 and ERF-NFκB chimeric molecules, other ERF chimeric molecules can be used to suppress, i.e., reduce, tumorigenicity associated with the aberrant activation of transcription activators (See, infra, methods to determine whether there has been a reduction in tumorigenicity).

The ERF repressor domain and the transcription factor lacking the transactivation domain can be bound together chemically or, alternatively, they can be synthesized recombinantly as a fusion protein using techniques known to and used by those of skill in the art. In addition, it will be readily apparent to those of skill in the art that the ERF chimeric molecules can also contain additional molecules, e.g., an antibody or be contained in a molecule, e.g., a liposome, to help direct the ERF chimeric molecules to the target site of interest.

1. Conjugation of the ERF Repressor Domain to the Transcription Factor

In one embodiment, the ERF repressor domain is chemically conjugated to the transcription factor. Means of chemically conjugating molecules are well known to those of skill. The procedure for attaching the ERF repressor domain to the transcription factor varies according to the chemical structure of the transcription factor. Polypeptides typically contain a variety of functional groups; e.g., carboxylic acid (COOH) or free amine ($-NH_2$) groups, which are available for reaction with a suitable functional group on either the ERF repressor domain or the transcription factor. Alternatively, polypeptides are derivitized to attach additional reactive functional groups. The derivatization optionally involves attachment of linker molecules such as those available from Pierce Chemical Company, Rockford Ill. A "linker", as used herein, is a molecule that is used to join the ERF repressor domain to the transcription factor. The linker is capable of forming covalent bonds to both the nucleic acid binding molecule and the ligand. Suitable linkers are well known to those of skill in the art and include, but are not limited to, straight or branched-chain carbon linkers, heterocyclic carbon linkers, or peptide linkers. Since the ERF repressor domain and the transcription factor are both polypeptides, the linkers are joined to the constituent amino acids through their side groups (e.g., through a disulfide linkage to cysteine), or to the alpha-carbon amino and carboxyl groups of the terminal amino acids.

In addition, a bifunctional linker having one functional group reactive with a group on a particular ligand, and another group reactive with a nucleic acid binding molecule, can be used to form the desired conjugate. Alternatively, derivatization can proceed through chemical treatment of the ligand or nucleic acid binding molecule, e.g., glycol cleavage of the sugar moiety of a glycoprotein with periodate to generate free aldehyde groups. The free aldehyde groups on the glycoprotein may be reacted with free amine or hydrazine groups on an agent to bind the agent thereto (See, e.g., U.S. Pat. No. 4,671,958). Procedures for generation of free sulfhydryl groups on polypeptides, are known (See, e.g., U.S. Pat. No. 4,659,839). Moreover, many procedures and linker molecules for attachment of various compounds to proteins are known. See, for example, European Patent Application No. 188,256; U.S. Pat. Nos. 4,671,958, 4,659, 839, 4,414,148, 4,699,784; 4,680,338; 4,569,789; and 4,589, 071; and Borlinghaus et al. *Cancer Res.* 47:4071–4075 (1987).

2. Production of Fusion Proteins

When both the ERF repressor domain and the transcription factor are relatively short, a chimeric molecule is optionally synthesized as a single contiguous polypeptide using standard chemical peptide synthesis techniques. Alternatively, the ERF repressor domain and the transcription factor can be synthesized separately, and then fused by condensation of the amino terminus of one molecule with the carboxyl terminus of the other molecule, thereby forming a peptide bond. Alternatively, the ERF repressor domain and the transcription factor can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is a preferred method for the chemical synthesis of the ligands of this invention. Techniques for solid phase synthesis are described by Barany and Merrifield, *Solid-Phase Peptide Synthesis*; pp. 3–284 in *The Peptides: Analysis, Synthesis, Biology*. Vol. 2: *Special Methods in Peptide Synthesis*, Part A., Merrifield, et al. *J. Am. Chem. Soc.*, 85:2149–2156 (1963), and Stewart et al., *Solid Phase Peptide Synthesis*, 2nd ed. Pierce Chem. Co., Rockford, Ill. (1984) which are incorporated herein by reference. Moreover, the nucleic acid sequences of the various transcription factors (e.g., GAL4, NFκB, MYC, Fli-1, EST1, etc.) are available from GENBANK via an accession number.

In a preferred embodiment, the ERF repressor domain-transcription factor fusion molecules of the invention are synthesized using the recombinant nucleic acid techniques described above. Generally, this involves creating a nucleic acid sequence that encodes the ERF repressor domain-transcription factor fusion molecule, placing the nucleic acid in an expression cassette under the control of a particular promoter, expressing the protein in a host, isolating the expressed protein and, if required, renaturing the protein. Techniques sufficient to guide one of skill through such procedures are found in, e.g., Berger, Sambrook, Ausubel, Innis, Goeddel, Krieger, and Freshney (all supra).

While the two molecules are often joined directly together, one of skill will appreciate that the molecules may be separated by a peptide spacer consisting of one or more amino acids. Generally, the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

Once expressed, the recombinant fusion proteins can be purified according to standard procedures, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol. 182: *Guide to Protein Purification.*, Academic Press, Inc. N.Y. (1990)). Substantially pure compositions of about 50 to 95% homogeneity are preferred, and 80 to 95% or greater homogeneity are most preferred for use in the methods of the invention.

One of skill in the art will recognize that after chemical synthesis, biological expression or purification, the ERF repressor domain-transcription factor fusion molecules of the invention may possess a conformation substantially different than the native conformations of the constituent polypeptides. In this case, it is often necessary to denature and reduce the polypeptide and then to cause the polypeptide to re-fold into the preferred conformation. Methods of reducing and denaturing proteins and inducing re-folding are well known to those of skill in the art (See, Debinski, et al., *J. Biol. Chem.,* 268:14065–14070 (1993); Kreitman and Pastan, *Bioconjug. Chem.,* 4:581–585 (1993); and Buchner, et al., *Anal. Biochem.,* 205:263–270 (1992).

G. Methods of Reducing Tumorigenicity

In another aspect, the present invention provides a method of reducing ets-dependent tumorigenicity, the method comprising: transfecting a tumor cell with an ERF gene or, alternatively, contacting a tumor cell with a peptide expressed by an ERF gene. As used herein, "ets-dependent tumorigenicity" refers to tumorigenicity associated with an oncogene having an ets-binding site (EBS) in their regulatory region. In a presently preferred embodiment, the methods of the present invention can be used to reduce ets-dependent tumorigenicity associated with an oncogene including, but not limited to, the following: v-mos, c-met, tpr-met, Ha-ras and gag-myb-ets. The overexpression of such oncogenes is known to produce tumors in a variety of mammalian cells and tissues including, but not limited to, cells and tissue present in the colon, breast, ovarian, prostate, kidneys, bone cartilage, muscle, etc. For example, the met oncogene has been associated with gastric carcinomas (Tahara, *Cancer,* 15:1410–1470 (1995), as well as breast cancer (Rahimi, et al., *DNA and Cell Biol.* 13(12):1189–1197 (1994)) and AIDS-related Kaposi's sarcoma (Naidu, et al., *Proc. Natl. Acad. Sci. USA* 91:5281–5285 (1994). Moreover, the ras oncogene has been found to be associated with both breast and colon cancer. As such, the methods of the present invention are useful for reducing tumorigenicity in, for example, colon, breast, ovarian, prostrate and hepatic tumor cells.

The methods of the present invention further include observing for a reduction in tumorigenicity, i.e., tumorigenic potential, of the sample tumor cells. This step includes observing for an inhibition of or reduction in sample tumor cell growth. Measures of tumor cell growth that are suitable include, for example, growth rate, colony formation in soft agar, tumorigenicity in an experimental animal, tumor cell phenotype, thymidine incorporation, drug sensitivity, etc. All of these are factors which alone or in combination with one another can be used to determine whether or not cell tumorigenicity has been reduced. A "reduction in tumorigenicity" is said to have occurred when, for example, a reduction, i.e., inhibition, in growth rate, colony formation in soft agar, tumor size, thymidine incorporation, etc. is observed. Additionally, it will be readily apparent to those of ordinary skill in the art that tumor phenotype(s), as noted by the clinician or other qualified observer, can be used to determine whether there has been a reduction in cell tumorigenicity. Observation for inhibition of growth is usually made daily, although other time intervals are practiced.

The growth rate, for example, can be measured by macroscopically observing how rapidly the tumor cells grow. This may be expressed as a doubling time (i.e., the amount of time it takes for the cells to double their numbers). Tumor cell growth rate can be measured in tissue culture by adding a fixed number of cells in tissue culture medium to a flask, culturing them in a 5% $CO_2$ humidified atmosphere, removing and counting an aliquot of the cells at different time points. By plotting the cell counts over time, it is possible to determine the doubling rate of the tumor cells.

Colony formation in soft agar is another measure of tumor growth. See, Wu, Y. and D. Cai, *Proc. Soc. Exp. Biol. Med.,* 201(3):284–288 (1992).

Tumorigenicity in an experimental animal can be measured by injecting an aliquot of cells, such as approximately $10^6$ cells, into an experimental animal subcutaneously and observing for tumor formation. See, Yeung, et al., *J. Surg. Res.* 53(2):203–210 (1992).

Phenotype refers to how the tumor looks, typically microscopically, but gross or macroscopic appearance can be observed. The phenotype changes depending on the growth rate of the tumor cells. For instance, the microscopic morphology of cells that are rapidly dividing and growing is different than that of cells that are dividing and growing at a normal rate. Determination of tumor cell phenotype is well within the ability of one with ordinary skill in the art.

Thymidine incorporation can be a measure of tumor cell growth because thymidine is incorporated into rapidly growing cells at a higher rate than into static or less rapidly growing cells. See, Saito, et al., *Eur. Arch. Otorhinolaryngol,* 249(7):400–403 (1992): and Brooks, D. J. and Carewal, H. S., *Int. J. Clin. Lab. Res.,* 22(4):196–200 (1992).

It will be readily apparent to those of ordinary skill in the art that a reduction or improvement in any one of the foregoing factors establishes that there has been a reduction in cell tumorigenicity.

As previously mentioned, the present invention provides a method for reducing cell tumorigenicity, the method comprising contacting a tumor cell with a peptide expressed by an ERF gene. It will be readily apparent to those of ordinary skill in the art that in addition to the entire peptide, biologically active fragments of the peptide may be used to reduce cell tumorigenicity. If biologically active fragments of the ERF peptide are used, it will be readily apparent to those of ordinary skill in the art that only that portion of the ERF gene encoding the biologically active fragment need be expressed if recombinant techniques are used to make the peptide. The selection of the portion of the ERF gene required to express a given peptide fragment will be apparent to those of ordinary skill in the art.

As such, the native ERF peptide may be subject to various changes, such as insertions, deletions, and substitutions, either conservative or non-conservative, where such changes might provide for certain advantages in their use. In fact, it has been found that mutations which abolish phosphorylation increase the repression and suppression function of ERF. By conservative substitutions is meant replacing an amino acid residue with another which is biologically and/or chemically similar, e.g., one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Residues which can be modified without loosing the biological activity of the native ERF peptide can be identified by single amino acid substitutions, deletions, or insertions using conventional techniques known to those of skill in the art. In addition, the contributions made by the side chains of the residues can be probed via a systematic scan with a specified amino acid (e.g., Ala).

Moreover, peptides which tolerate substitutions while retaining the desired biological activity may also be synthesized as D-amino acid containing peptides. Such peptide may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the ERF peptide.

In addition to the foregoing, the present invention provides pharmaceutical compositions comprising the ERF protein or a fragment thereof in an amount sufficient to reduce or inhibit tumorigenicity, and a pharmaceutically acceptable diluent, carrier or excipient. The pharmaceutical compositions of the present invention are suitable for use in a variety of drug delivery systems. Suitable formulations for use in the present invention are found in Remington's Pharmaceutical Sciences (Mack Publishing Company, Philadelphia, Pa., 17th ed. (1985)), which is incorporated herein by reference. In addition, for a brief review of methods for drug delivery, see, Langer, Science 249:1527–1533 (1990), which is incorporated herein by reference.

As described above, the ERF gene and the expression product of the ERF gene have tumor suppressor activity. As such, the present invention provides for therapeutic compositions or medicaments comprising one of the ERF peptide of, fragments thereof as described hereinabove in combination with a pharmaceutically acceptable excipient, wherein the amount of the ERF peptide present in the composition is sufficient to provide a therapeutic effect.

In a therapeutic application, the ERF peptide is embodied in pharmaceutical compositions intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the ERF peptide, as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the ERF peptide is preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, the ERF peptide of the invention are administered to a patient in an amount sufficient to reduce, i.e., inhibit, cell tumorigenicity. An amount adequate to accomplish this is defined as "therapeutically effective dose." Amounts effective for this use will depend on, for example, the peptide composition employed (e.g., whether the ERF peptide or a fragment thereof is used), the manner of administration, the stage and severity of the disease being treated, the weight and general state of health of the patient, and the judgment of the prescribing physician, but generally range for the initial immunization (that is for therapeutic or prophylactic administration) from about 1.0 $\mu$g to about 5000 $\mu$g of peptide for a 70 kg patient, followed by boosting dosages of from about 1.0 $\mu$g to about 1000 $\mu$g of peptide pursuant to a boosting regimen over weeks to months depending upon the patient's response and condition by measuring or observing the various factors described above for determining whether a reduction in tumorigenicity has been achieved.

The ERF peptides useful in the methods or compositions of the present invention may also be administered via liposomes, which serve to target the peptides to a particular tissue, such as lymphoid or colon tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, for example, Szoka, et al., Ann. Rev. Biophys. Bioeng., 9:467 (1980); U.S. Pat. Nos. 4,235,871, 4,501,728, 4,837,028; and 5,019,369, the teachings of which are incorporated herein by reference.

For targeting to the immune cells, a ligand to be incorporated into the liposome can include, for example, antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

The invention will be described in greater detail by way of specific examples. The following examples are offered for illustrative purposes, and are intended neither to limit or define the invention in any manner.

EXAMPLES

A. General Methodology

The following protocols and experimental procedures are referenced in the examples which follow.

1. Libraries and Plasmids

The K562 CDNA library in bacteriophage λt11 was prepared with the Pharmacia (Piscataway, N.J.) CDNA synthesis kit using only random primers for the reverse transcription of mRNA. Double-stranded cDNA between 300–1200 bp was separated on a Sephacryl S300 column and inserted into the EcoR1 site of the vector by an EcoRI/Not adapter that also provides a three alanine residue spacer between the β-galactosidase protein and the cDNA-encoded protein. Three-hundred-thousand clones were screened for their ability to encode a protein that can interact with the multimerized double-stranded H1 oligonucleotide (GATCTGGAGGAAGTAA) SEQ ID NO:9. All the DNA and RNA methods were performed according to Sambrook, et al. (1989). The phage insertswere recovered by NotI digestion, cloned into pBluescript SK+ (Stratagene, La Jolla, Calif.) and sequenced by the dideoxy method. Expression plasmids of ERF were generated by introducing the appropriate restriction fragments into the pSG5 (Stratagene, La Jolla, Calif.) or pSG424 (Sadowski, et al., *Nucleic Acids Res.*, 17:7539 (1989)) vectors. The chloramphenicol acetyl transferase (CAT) reporter plasmids, TK-GATA, TK-HIV, TK-MHC and HIV-LTR were kindly provided by Dr. Seth (Seth, et al., *AIDS Res. Hum. Retroviruses*, 9:1017–1023; Seth, et al., *Oncogene*, 8:1783–1790 (1993)). The GATA-1 reporter plasmid was kindly provided by Dr. Evans (Hannon, et al., *Proc. Natl. Acad. Sci. USA*, 88:3004–3008 (1991)). The ETS2 reporter plasmid was constructed by introducing the 520 bp BssHII fragment (−394 to +125) into the PUMS-$P_L$ CAT vector (Jorcyk, et al., 1991). The SV40/GAL4 reporter plasmid was generated by the introduction of the 120 bp PstI-XbaI fragment from pG5E1BCAT (Lillie and Green, 1989) that contains five GAL4 binding sites into the Bgl11 site of the pCAT control vector (Promega, Madison, Wis.). pERFΔD was generated by the removal of the first 424 bp of the ERF cDNA to the XmaI site and the insertion of an inframe translation initiation codon by an NcoI linker. RME26 was generated by the insertion of the 500 bp NdeI-Hind111 fragment of RSV-CAT (Gorman, et al., 1982) into the unique MluI site of ME26. The pSG5/ETS1 expression plasmid has been described elsewhere (Mavrothalassitis, et al., 1994). The pT24 plasmid that contains an activated Ha-ras gene (Capon, et al., 1983) and the pRSV-Raf-BXB plasmid that contains the kinase domain of c-Raf-1 under the transcriptional control of RSV-LTR (Bruder, et al., *Genes Dev.*, 6:545–556 (1992)) were kindly provided by Dr. Capon and Dr. Rapp, respectively.

2. Cell Lines, Transfection and Transformation

HeLa cells were maintained in DMEM (Life Technologies, Gaithersburg, Md.) supplemented with 10% bovine serum. NIH3T3 cell lines were maintained in DMEM supplemented with 8% bovine serum. The NIH3T3/FBJ v-fos transformed cell line was originally obtained from Dr. Tom Curran (Roche Research Center). The NIH3T3/Ha-ras cell line carries a V12G mutant Ha-ras gene and was previously described (Lu, et al., *Int. J. Cancer*, 6:45–53 (1991)). The v-src cell line was generated by transfecting the SR-A RSV construct (DeLorbe, et al., *J. Virol.*, 36:50–61 (1980)) into NIH3T3 cells and the cells were found to be consistent with the v-src transformed phenotype (D.B., unpublished data). The low-serum growth ability was tested in DMEM, 20 mm Hepes, 1% or 0.2% bovine serum or QBSF51 (Quality Biological, Gaithersburg, Md.) in the presence or absence of 0.1% bovine serum. The cell line transfections were performed by the calcium phosphate method. Transformed clones with stably integrated plasmids were selected for their ability to express the neomycin resistance gene and to grow in the presence of 400 μg/ml gentamycin-sulfate (G418). Promoter activity was determined by a diffusion-based chloramphenicol acetyl transferase (CAT) assay using $^{14}$C-labeled acetyl-coenzyme-A (NEN, Wilmington, Del.) according to the company's protocol. Transfection efficiency was normalized according to β-galactosidase activity produced by a constant amount (2 μg) of the pRSV-β-GAL reporter plasmid.

3. Protein Detection and Phosphorylation

The M15C and S17S rabbit polyclonal antibodies were generated against peptides derived from the amino-14 and carboxy-17 amino acids of the predicted ERF protein, respectively, and purified by affinity chromatography. Immunoblotting and immunoprecipitation was performed according to Harlow and Lane (1988). Cells were labeled with either $^{35}$S-methionine for 2 hr in methionine-free media or for 4 hr with $^{32}$P-$H_3PO_4$ in phosphate-free media. Cells were synchronized by serum starvation, hydroxyurea block or nocodazole block according to Paules, et al., *Oncogene*, 7:2489–2498 (1992). ERF protein was produced in the reticulocyte lysate translation system (TNT, Promega, Madison, Wis.) and labeled with either $^{35}$S-methionine or [$^{32}$P τ]ATP. Activated Erk2 kinase was kindly provided by Dr. Nataly Ahn (Seger, et al., *Proc. Natl. Acad. Sci. USA*, 88:6142–6146 (1991)), calmodulin/CaM kinase 11 was provided by Dr. Thomas Soderling (Brickey, et al., *Biochem. Biophys. Res. Commun.*, 173:578–548 (1990)), cdc2/cyclin B was purchased from UBI (Lake Placid, N.Y.) and PKC was purchased from Promega (Madison, Wis.). The phosphorylation reactions were carried out by incubating 1 μg/μl of each kinase (3 μg/μl for Erk2) for 15 min at 30° C. either directly into the translation reaction in the absence of additional ATP, or after immunoprecipitation of the ERF protein in the presence of 10 μM 600 Ci/Mol [$^{32}$P-τ]ATP. Phosphopeptide and phosphoamino acid analysis was performed according to Boyle, et al., *Methods Enzymol.*, 201:110–149 (1991).

4. Electrophoretic Mobility Shift Assay (ENSA)

Nuclear extracts from HeLa cells were prepared according to Lassar, et al., *Cell*, 66:305–315 (1991). Ten micrograms of nuclear extract were incubated with 0.2 pmole of a $^{32}$P-labeled 120 bp PstI-XbaI fragment of pG5E1BCAT that contains 5 GAL4 binding sites in the presence of 2 μg calf thymus DNA. The complexes were analyzed in 5% acrylamide gel and visualized by autoradiography.

B. Examples

1. cDNA Isolation and Sequencing

Figure 1B-1:
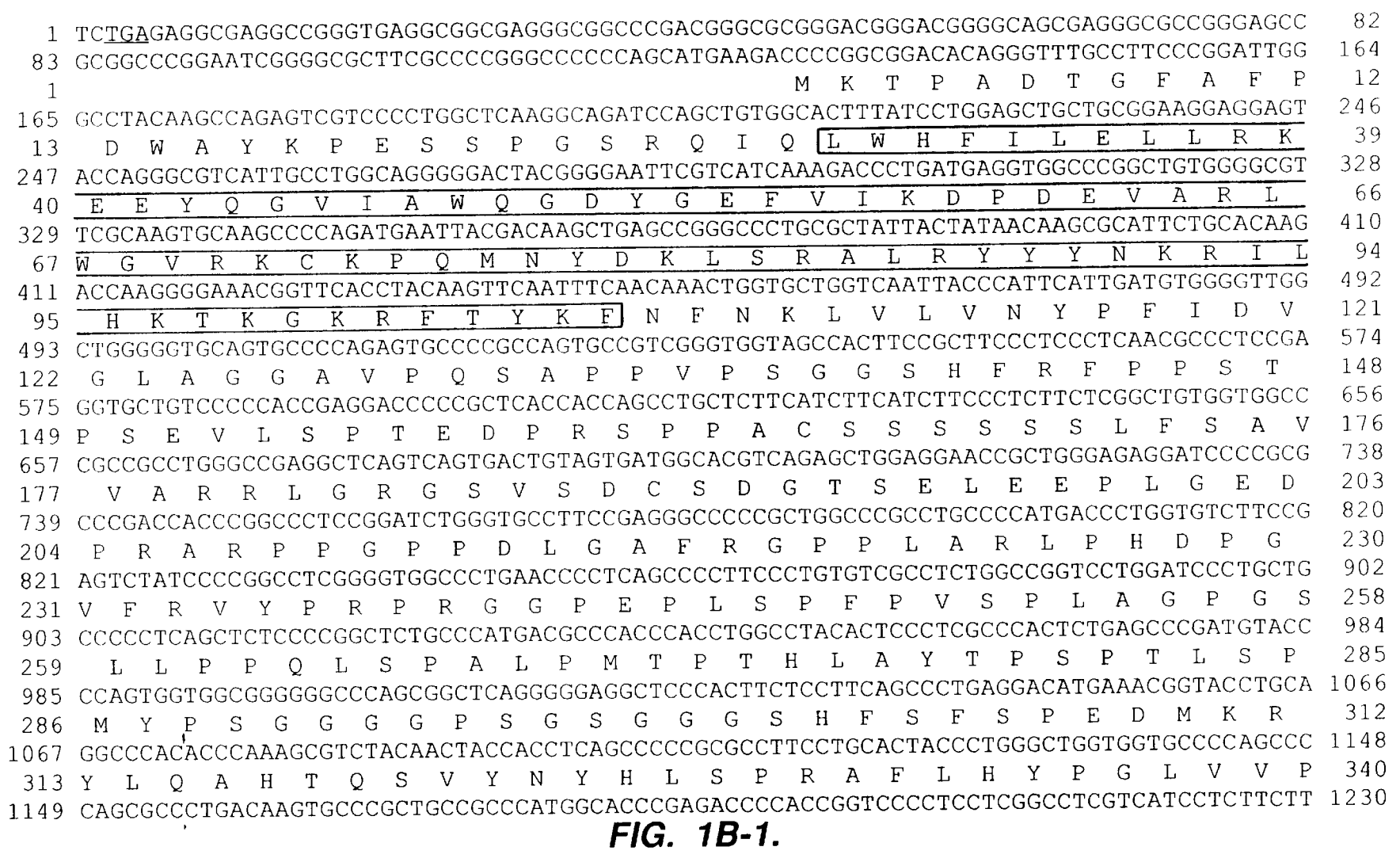

Previously, at least three DNA-protein interaction sites within the ETS2 promoter surrounding the transcription initiation sites have been identified. The H1 site of the ETS2 promoter, which contains an ets binding site (EBS) (Mavrothalassitis, et al., *Cell Growth Differ.*, 2:215–224 (1991)), was of great interest because strong evidence has suggested that ETS2 may be regulated by ets genes other than the already known members of the family, which cannot interact effectively with this site and thus regulate ETS2 transcription. To identify gene products that are capable of interacting with this EBS, a cDNA library was constructed from K562 cell mRNA in λgt11. By screening this library with the H1 DNA oligonucleotide probe, one clone (#45) was isolated that produced a 165 kb β-galactosidase fusion protein capable of binding specifically to the H1 oligonucleotide in a southwestern experiment (data not shown). The insert from clone #45 was used to isolate clones #35 and #30 from the same library via Southern hybridization, and the insert from clone #30 was used to isolate clone #4 from a human placenta cDNA library (FIG. 1A). All the clones were sequenced and were found to be identical in their overlapping segments. Full-length cDNA was generated by splicing clones #45 and #4 at the EcoRI site at bp 284 (FIG. 1B). The 2.7 kb cDNA contains a 1644 bp open reading frame (ORF) that is preceded by an in-frame stop codon 5 bp from the 5' end of the cDNA and contains a polyadenylation signal 20 bp before the end of the clone (FIG. 1B). The ERF cDNA can detect a 2.7 kb mRNA in Northern blots, indicating that the entire ERF cDNA has been isolated. The predicted 548 amino acid protein contains an ets DNA-binding domain close to the amino-terminus of the protein that is structurally similar to ELK1 and SAP1. However, the homology between the ERF and all the known ets domains is 50%–70%, the best being with ETS1 (FIG. 1C), and there is no significant homology between ERF and any other ets gene outside the DNA-binding domain. Furthermore, no significant homology can be detected between ERF and any other protein or DNA sequence in the databanks. ERF protein has a proline-rich central region (between 200 and 420 amino acids) with multiple putative phosphorylation sites for MAP (7 sites) and cdc2 (3 sites) kinases, as well as putative SH3 interaction sites.

2. Functional Analysis of ERF

Figure 2B:
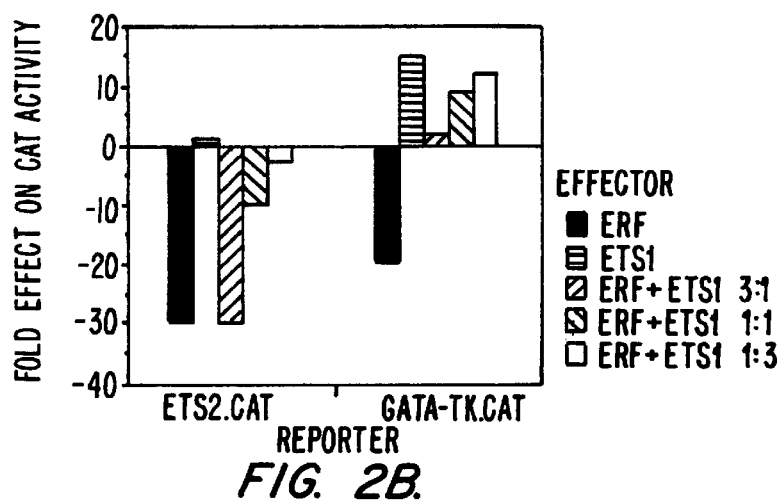

All the ets genes, with the exception of Yan (O'Neill, et al., *Cell*, 78:137–147 (1994); Lai, et al., *Cell*, 70:609–620 (1992); Tei, et al., *Proc. Natl. Acad. Sci. USA*, 89:6856–6860 (1992)), are known to be potent transcriptional transactivators when tested in transient transfection assays. The full-length ORF of ERF was tested after placing it under the transcriptional control of the SV40 promoter/enhancer in transient transfection assays of HeLa cells with a variety of promoter-reporter constructs and it was found that ERF is a potent repressor of transcription. The full-length ETS2 promoter was repressed more than 30-fold and when other promoters were tested, the level of transcriptional repression was proportional to the affinity of ERF for its target sequence in the respective promoter (data not shown), suggesting a binding-dependent inhibition of transcription (FIG. 2A). Furthermore, addition of a transactivator capable of recognizing similar (but not identical) sequences (like ETS1) could reverse the repression effects in a dosage-dependent manner (FIG. 2B).

Figure 2C:
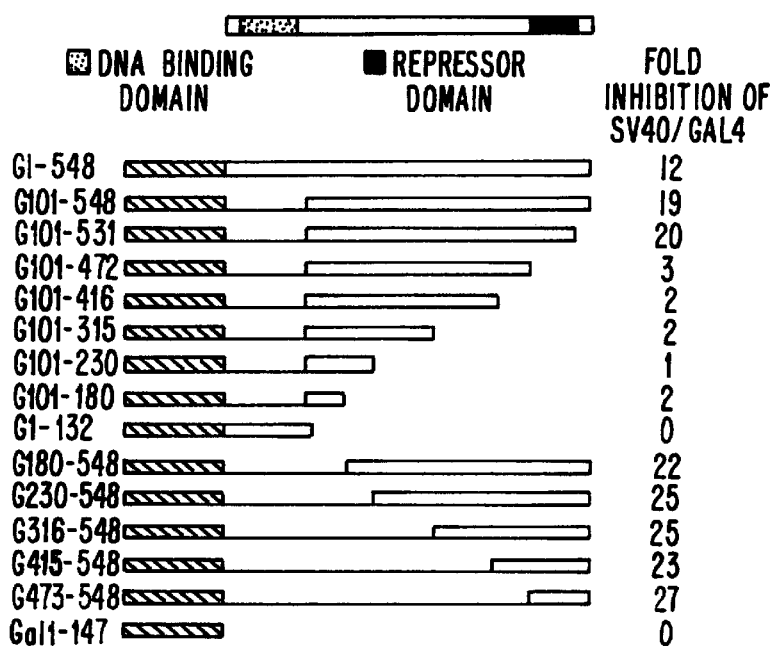
Figure 2D:
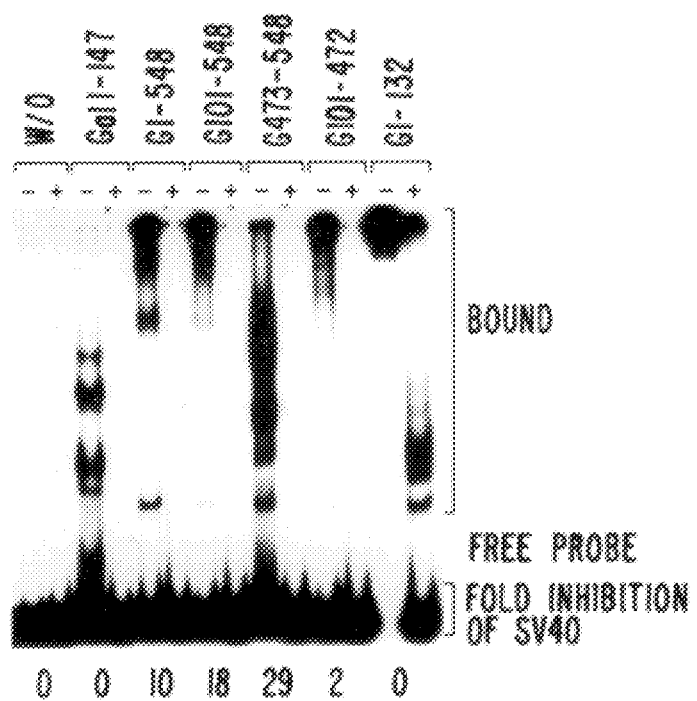

To determine the functional domains of the ERF protein, a series of truncated ERF constructs were generated and their effect on the transcription of two reporter constructs containing either the ETS2 promoter or the TK-GATA artificial promoter was tested. The data indicate that carboxy-terminal truncations of ERF decrease the repressor activity, but even the DNA-binding domain alone strongly inhibits the ETS2 promoter, probably by occupying an important site by a nonfunctional protein (data not shown). To overcome effects related to the displacement of cellular activators rather than active inhibition of transcription, a series of fusion proteins between the GAL4 binding domain and different portions of the ERF gene were generated. The SV40 promoter/enhancer construct containing five GAL4 binding sites upstream of the enhancer/promoter, or between the enhancer and the promoter, was used as a reporter. The data indicate that the region between amino acid 472 and amino acid 530 retains full repressor activity (FIG. 2C). To ensure that repression level variations among different portions of the repressor domain are not due to the adjacent regions, which can either mask its activity or act as transactivators, the level of fusion proteins that had migrated into the nucleus and were capable of interacting with the GAL4 recognition sequence was determined. The data indicate that repression of the SV40 promoter is proportional to the amount of the GAL4-ERF fusion protein that is capable of interacting with the GAL4 recognition sequence, thus the observed variations are probably due to the stability of the different fusion proteins and/or their ability to migrate to the nucleus and interact with the GAL4 recognition motif (FIG. 2D).

3. Repression of ets-Dependent Transformation by ERF

Figure 3A:
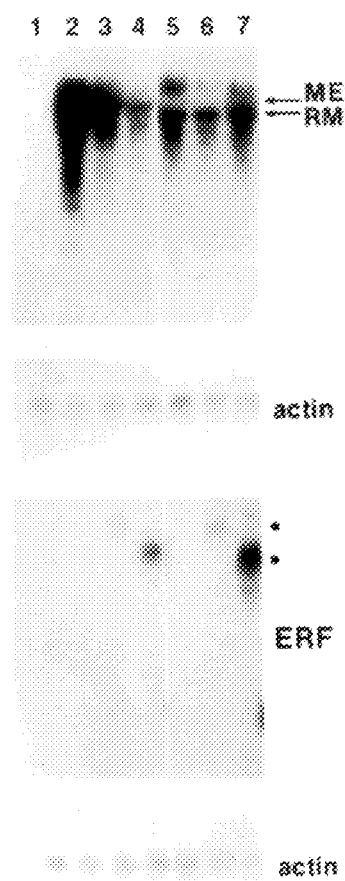
FIG. 3 illustrates that ERF Can Suppress ME26-Induced Transformation of NIH3T3 Cells. (A) NIH3T3 cells were co-transfected with the indicated plasmid selected with G418 and the pool of clones was plated in QBSF51, 0.1% bovine serum for 15 days and stained with Giemsa stain. (B) Northern blot analysis of the NIH3T3 cells transfected with pSV2Neo (lane 1), ME26 (lane 2), ME26 and ERF (lane 3), ME26 and ERFΔD (lane 4), RME26 (lane 5), RME26 and ERF (lane 6) and RME26 and ERFΔD (lane 7). The arrows and the dots indicate the positions of gag-myb-ets and ERF mRNAs, respectively.
Figure 3B:
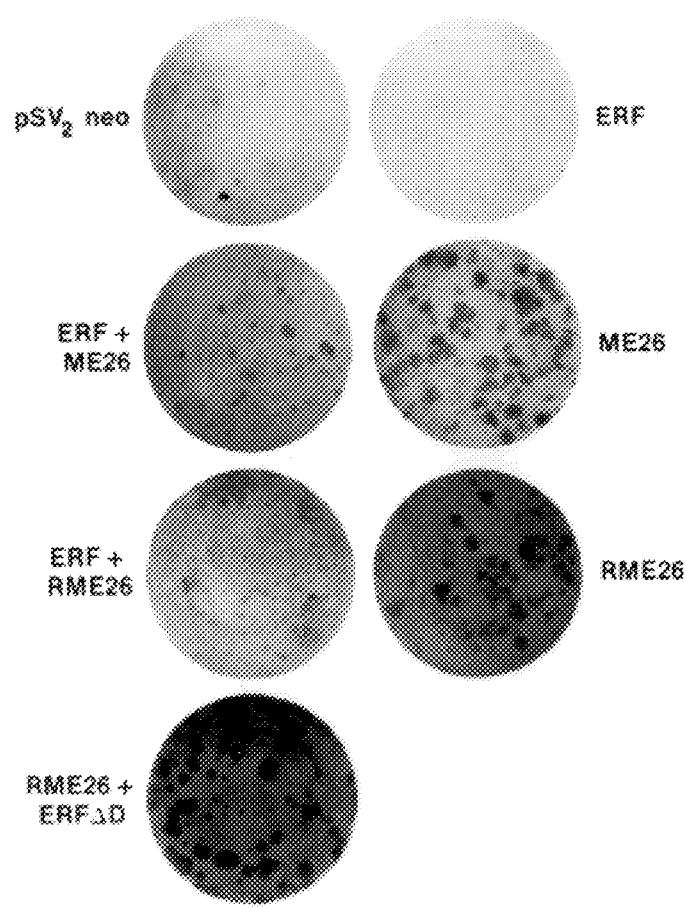

The E26 virus (Nunn, et al., *Nature*, 306:391–395 (1992); Leprince, et al., *Nature*, 306:395–398 (1983)), which contains the prototype v-ets oncogene fused with v-myb, induces erythroleukemias in chicken and exhibits strong tumorigenic activity when introduced into murine cells (Yuan, et al., *J. Virol.*, 63:205–215 (1989)). In addition, several other members of the ets family of genes (ETS1, ETS2 and Fli-1) have been reported to transform mouse fibroblast NIH3T3 cells and induce them to form tumors after injection into athymic mice (Seth, et al., *Proc. Natl. Acad. Sci. USA*, 86:7833–7837 (1989); Seth, et al., *Oncogene*, 5:1761–1767 (1990); May, et al., *Proc. Natl. Acad. Sci. USA*, 90:5752–5756 (1993)). The transforming activity of the p135$^{gag-myb-ets}$ polypeptide and other ets genes in mouse cells requires a functional ets DNA-binding domain (Yuan, et al., *J. Virol.*, 63:205–215 (1989); and unpublished data), indicating that the effect is mediated via ets binding to its recognition sequence. Since all the transforming ets genes are transcriptional activators, the ability of ERF to repress transformation induced by the ME26 virus expressing the p135$^{gag-myb-ets}$ fusion protein under the control of an MSV-LTR (Yuan, et al., *J. Virol.*, 63:205–215 (1989) was tested. The initial experiments indicated that ERF could very effectively repress ME26-induced transformation (FIG. 3B). The ability of the ERF gene, however, to repress transcription of the MSV-LTR (Gunther, et al., *Genes Dev.*, 4:667–679 (1990)) that is responsible for gag-myb-ets mRNA transcription, obscures the mechanism of the transformation suppression activity. To overcome this problem, the ME26 virus was re-engineered to transcribe the gag-myb-ets mRNA via the RSV-LTR, which is not repressed by the ERF gene (FIG. 3A). The data indicates that ERF can repress both the low-serum growth (FIG. 3B) and tumorigenicity of NIH3T3 cells (Table 1) transformed by ME26 without affecting the gag-myb-ets mRNA levels. Furthermore, this suppression requires the DNA-binding domain of ERF, indicating that the suppression is due to repression of specific genes that can be regulated via an EBS. These data indicate that ERF may act in the same pathway as gag-myb-ets, or even directly compete for the transcriptional regulation for a certain set of genes responsible for the tumorigenic phenotype.

TABLE 1

Repression of gag—myb—ets Tumorigenicity by ERF

| Cell Line | Animals With Tumors (4 weeks) |
|---|---|
| psv$_2$neo | 1/6 |
| RME26 | 6/6 |
| RME26 + ERF | 0/6 |

One million cells of the pooled NIH3T3 clones generated after transfection with the indicated plasmids were injected subcutaneously into athymic mice. The animals were monitored twice a week for tumor development and general health condition.

4. The ERF Protein is Phosphorylated as a Function of Cell Cycle and Mitogenic Stimulation Most of the ets genes exhibit a selective expression pattern which is believed to contribute to the functional specificity of the ets family members. In contrast, the ERF mRNA can be detected in all cell lines and tissues tested at a very constant level (data not shown). Furthermore, the level of ERF mRNA, when tested by RNA protection assays, is found to be constant throughout the cell cycle and does not vary at different growth stages (data not shown). The above indicates that very little, if any, of the ERF regulation is at the transcriptional level. To determine any possible regulation for this ubiquitously-expressed transcriptional repressor at the post-transcriptional level, two antibodies were developed against the ERF protein. Each antibody specifically recognizes the same multiple bands, in immunoprecipitation and immunoblotting, in the range of 75–85 kD, which is in agreement with the size of the in vitro translated protein.

Figure 4A:
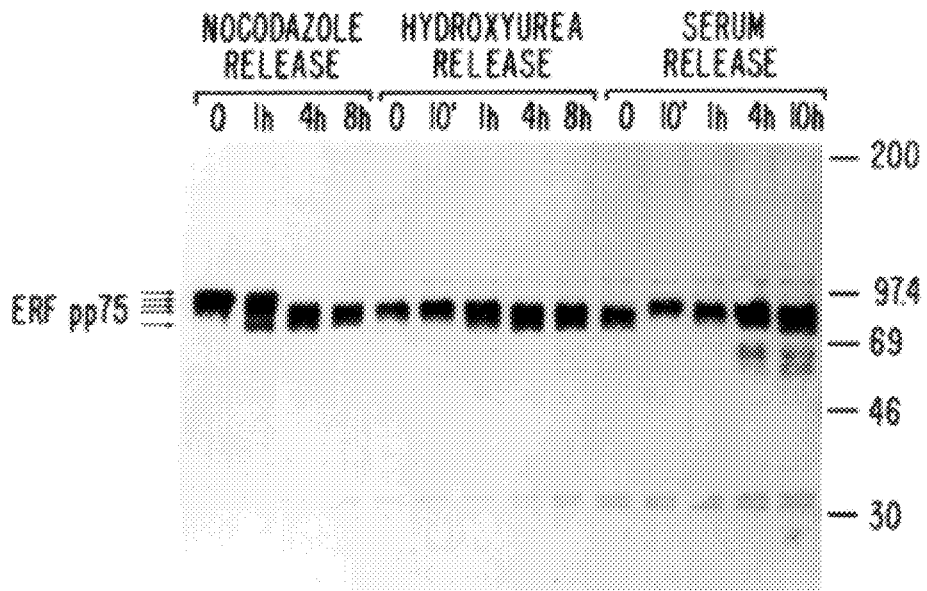
FIG. 4 illustrates that the phosphorylation of ERF protein is regulated during the cell cycle and mitogenic stimulation. (A) HeLa cells overexpressing ERF protein were synchronized by nocodazole block, hydroxy urea block and serum deprivation and were released in complete media. At the indicated time point, the cells were harvested and ERF protein was detected by immunoblotting with the S17S ERF-specific antibody. The ERF-specific bands are indicated by arrows. Numbers on the right indicate the position of the size standards. (B) HeLa cells overexpressing ERF protein were treated with the indicated reagents for 10 minutes (PMA, OAG, ionomycin) or 60 minutes (okadaic acid). The ERF protein was detected by immunoblotting as in (A).

The multiple observed bands are the result of protein phosphorylation and can be eliminated after treatment with PP-1 or PP-2A phosphatase (not shown). Multiple phosphorylation isoforms of ERFs exist at any given time within a cell throughout the cell cycle (FIG. 4A). The phosphorylation level of the protein changes at different points in the cycle. There is limited phosphorylation during entry into the S phase after release from hydroxyurea, hyperphosphorylation after serum induction, and a very dramatic phosphorylation at the G2/M boundary observed after blocking mitosis with nocodazole. GI/S phosphorylation is very rapid, transient and limited, since there are no additional phosphorylated bands other than those that appear to be due to the elimination of the hypophosphorylated species. During the $G_0/G_1$ transition after addition of serum, an immediate (within 2 min) hyperphosphorylation of the ERF protein was observed. The phosphorylation returned to normal levels after 60 min, indicating that ERF phosphorylation is an immediate mitogenic response. The hyperphosphorylated forms of ERF observed at the G2/M transition are undetectable after the completion of mitosis and entry into the G1 phase. Mitotic cells collected in the absence of nocodazole by mitotic shakeoff contain similar hyperphosphorylated forms of ERF; this eliminates the possibility of artifacts related to nocodazole rather than the mitotic process.

Figure 4B:
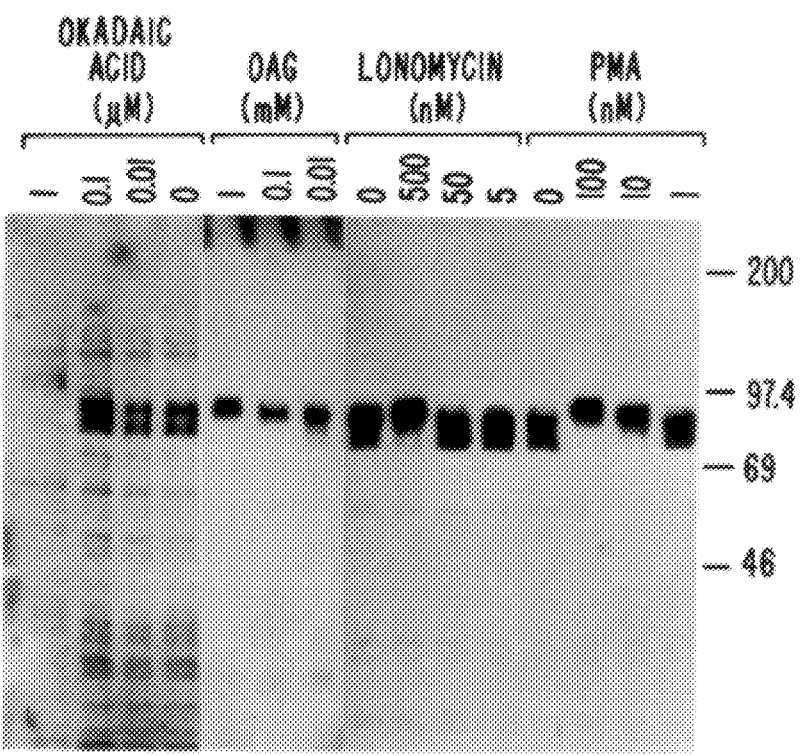

The hyperphosphorylation of ERF during the $G_0/G_1$ transition suggests that phosphorylation may be a response to mitogenic stimuli; therefore, the effect of mitogenic compounds, which are known kinase activators or inhibitors, on ERF phosphorylation was determined. Short exposure (5-15 min) to phorbol 12-myristate 13-acetate (PMA), ionomycin or 1-oleoyl-2-acetyl-sn-glycerol (OAG) increased the phosphorylation level of ERF (FIG. 4B), in contrast to treatment with forskolin (a PKA activator) or kinase inhibitors (i.e., those specific for PKA, PKC and CaMKII kinase or the broad specificity kinase inhibitor Stavrosporin), which had no observable effect on ERF phosphorylation (data not shown). The phosphatase inhibitor, okadaic acid, however, induced a dramatic phosphorylation of ERF to levels similar to those observed during G2/M transition (FIG. 4B).

Figure 5A:
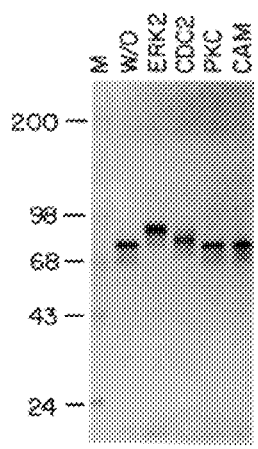
FIG. 5 illustrates the phosphorylation of ERF by Erk2 and cdc2 kinases. (A) ERF protein was synthesized in vitro and labeled by $^{35}$S-methionine. At the completion of synthesis, the indicated kinases were added and the buffer was adjusted to the optimum for each kinase. The ERF protein was detected by autoradiography. (B) Phosphopeptide analysis of ERF protein phosphorylated in vivo or in vitro with the indicated kinase(s). ERF protein was purified by immunoprecipitation from HeLa cells overexpressing ERF, labeled for 4 hr with $^{32}$P and stimulated by serum for 10 min (in vivo). In vitro-produced protein was purified by immunoprecipitation and labeled with [$^{32}$P-τ]ATP and the indicated kinase. The labeled proteins were separated by gel electrophoresis, extracted from the gel, subjected to proteolytic cleavage by trypsin and the phosphopeptides were analyzed by electrophoresis and chromatography. The filled arrowhead in the "in vivo" panel indicates peptides phosphorylated by Erk2 kinase in vitro and the open arrowhead indicates peptides phosphorylated by cdc2.

The phosphorylation pattern of the ERF protein in untransformed HeLa cells was determined to be identical to the pattern described above, both during cell cycle and mitogenic stimulation (not shown). The in vivo phosphorylation pattern of ERF, in conjunction with the presence of putative phosphorylation sites on the ERF protein sequence, suggests that MAP, PKC, CAM and cdc2 kinases may directly phosphorylate ERF. The ability of these kinases to phosphorylate ERF in vitro was determined, and it was found that they all can phosphorylate ERF in distinct sites; however, only phosphorylation by Erk2 and cdc2 kinases results in a visible mobility shift of the protein in polyacrylamide gel electrophoresis that is consistent with the bands observed in vivo (FIG. 5A).

Figure 5B:
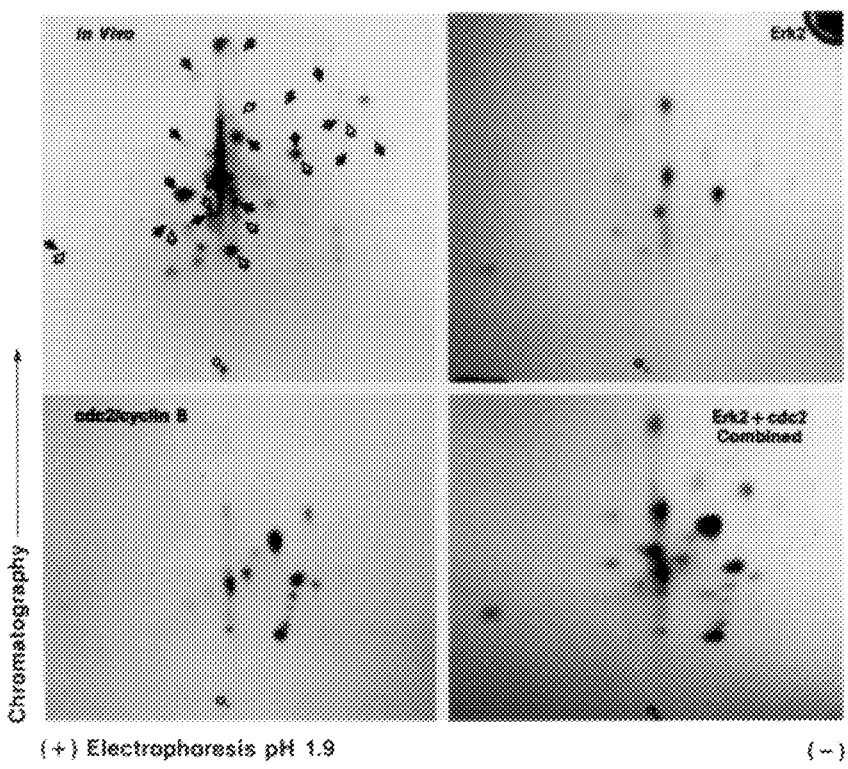

In addition, the mobility shift that was observed in SDS gel electrophoresis of the truncated ERF proteins after in vitro phosphorylation by Erk2 was identical to the shifts observed in vivo after transient transfection and stimulation by PMA (not shown). In vitro phosphorylation by these kinases did not appear to affect the ability of ERF to interact with its recognition DNA sequence (data not shown), indicating that phosphorylation may affect protein-protein interactions, protein stability, nuclear localization, sequence specificity, or some other function required for ERF activity. ERF protein phosphorylated in vivo exhibits a complex phosphopeptide map, indicating that the multiple bands observed in immunoblotting or immunoprecipitation reflects phosphorylation at multiple sites. Phosphoamino acid analysis indicates that the protein is phosphorylated on serine and threonine residues only. Comparison of phosphopeptide maps between the in vivo phosphorylated protein and protein phosphorylated in vitro by different kinases indicates that no single kinase can account for all the observed phosphorylation of the protein; however, it is an indication that these or related kinases are involved in ERF phosphorylation in peptides that are found phosphorylated in vivo (FIG. 5B).

5. Modulation of ERF By the ras Signaling Pathway

Figure 6A:
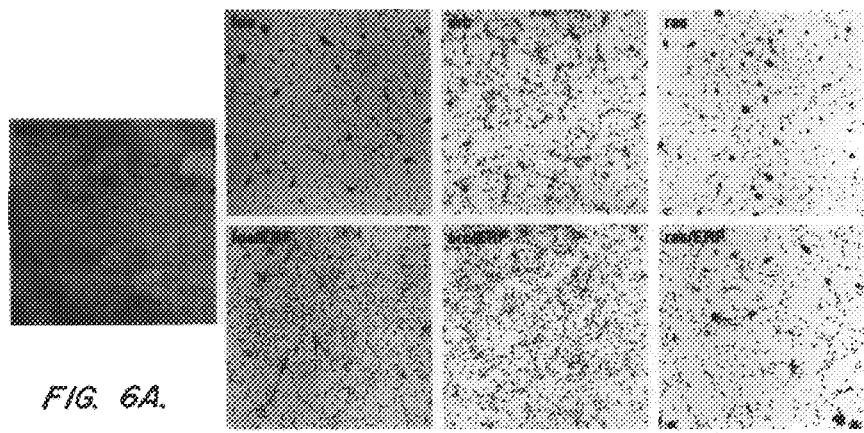
FIG. 6 illustrates that the activation of the ras/MAPK pathway inhibits ERF activity. (A) NIH3T3 cells transformed by v-fos, Ha-ras and v-src were tested for their ability to grow in low-serum media after the introduction of the ERF gene. The morphological transformation was determined after seven days in DMEM supplemented with 1.0% bovine serum. (B) The level and the phosphorylation state of the ERF protein from the cell lines described in (A) were determined by immunoblotting with the S17S ERF-specific antibody. The arrow indicates the ERF-specific bands. (C) One microgram of the pTK-GATA.CAT reporter plasmid was co-transfected into HeLa cells with 0.5 μg of ERF, 1 μg of Ha-ras and 1 μg of the kinase domain of c-raf-1-expressing plasmids at the indicated combinations. The height of the bars indicate relative CAT activity in the absence or presence of ERF.
Figure 6B:
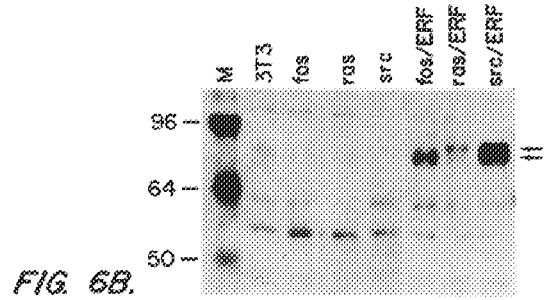
Figure 6C:
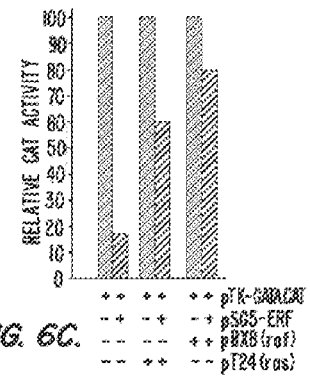
Figure 7:
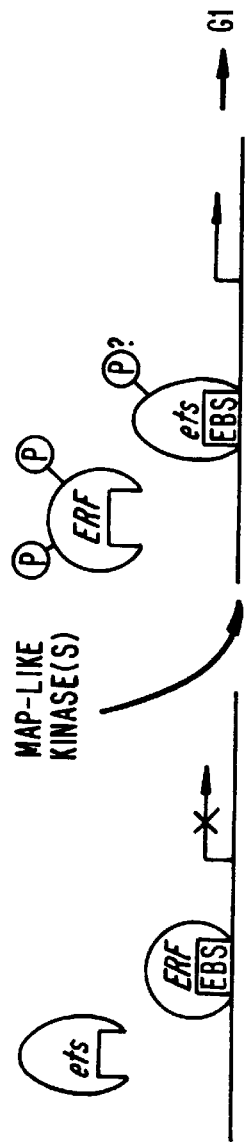
FIG. 7 illustrates a simplified model for the ERF function. A subset of genes required for cell proliferation is repressed by ERF. Upon the proper mitogenic stimulation, ERF is phosphorylated and its repressing activity is diminished. A transactivating member of the ets family is now capable of promoting transcription of the target genes. The presence of the proteins over the ets binding site (EBS) represents the dominant activity rather than the actual physical interaction.

The phosphorylation of ERF in response to mitogenic stimulators and its in vitro phosphorylation by MAP kinase in sites similar to the ones found phosphorylated in vivo suggested that ERF may be involved in the branch of the ras signal transduction pathway that is mediated by MAP kinase. To test this hypothesis, ERF was introduced into NIH3T3 cells transformed by the v-fos, activated Ha-ras or v-src oncogenes, and it was found that the ERF protein was hyperphosphorylated totally in the Ha-ras and partially in v-src-transformed cell lines, but not in the v-fos-transformed cell lines (FIG. 6B). Furthermore, the ras/ERF-transformed cell lines did not exhibit any apparent difference when compared to the parental Ha-ras-transformed cells, either in low-serum growth or morphology, and the src/ERF-transformed cells exhibited only minimal morphological changes compared to the parental src-transformed cells. In contrast, v-fos/ERF-transformed cell lines exhibited a decreased ability to grow in low serum and an altered morphology, but their transformed phenotype was not fully reverted when compared to NIH3T3 cells (FIG. 6A). This indicates that either critical genes that are regulated by v-fos and contribute to the transforming phenotype are not affected by ERF, or that ERF can inhibit the activation only in a subset of genes activated by fos, possibly by displacing other ets genes in the oncogene-responsive unit described earlier (Wasylyk, et al., *Nature,* 346:191–193 (1990)). In all of the cases, no effect in the transcription level of the transforming oncogene was observed (data not shown). Consistent with the inability of ERF to induce any changes in the Ha-ras and v-src-transformed cells was the ability of MAPK pathway activators to inhibit ERF function. Both Ha-ras and raf were capable of decreasing the ERF repressor activity when tested in a transient transactivation assay (FIG. 6C). Taken together, the above indicate that ERF is probably a downstream effector in the ras signalling pathway and is regulated via MAPK.

6. Preparation of the ERF Chimeric Molecules a. Fli1-ERF: Insertion of an NcoI linker at the Sty1I site (at amino acid 244) of the human ERGB/Fli1 gene to generate an in-frame translation initiation codon. Verify recombinants by restriction digest and sequencing. Ligate the 440 bp EcoRI-RsaI fragment (at amino acids 234–380) of the Fli-1 (with the NcoI linker to the 1623 bp XmnI-BstEII fragment of ERF (at amino acids 100-end). The recombinants were verified by restriction digest, sequencing and in vitro translation.

b. The ERF-Fli1 Chimeric Molecule: Insertion of an in-frame NcoI linker at the SmaI site of the ERF gene (at amino acid 473). Ligate the 260 bp BspMI-HinfI fragment (amino acids460–547) of ERF (with the NcoI linker) to the 660 bp EcoRI-HindIII fragment (amino acids 234-end) of ERGB/Fli1. The recombinants were verified with restriction, sequence and in vitro translation.

c. ER-κB p50 and p65 Chimeric Molecules: The 500 bp SmaI-BstEII fragment of ERF was ligated into the PpuMI site (amino acid 442) or the BsgI site (amino acid 365) of p50 to generate the KBp-ERF and KBb-ERF, respectively. Insertion of an oligonucleotide that has translation termination codons in all frames was used to generate KBp and KBb. For the p65 the insertion was at the Bsu36I site (aa 419) to generate the p65b-ERF and p65b. All the constructs were verified by restriction digest, sequencing and in vitro transcription.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. An isolated DNA sequence which encodes an ETS2 Repressor Factor protein and said DNA sequence hybridizes under high stringency conditions to an ETS2 Repressor Factor gene in a human genomic library, said ETS2 Repressor Factor gene having a nucleic acid sequence comprising SEQ ID NO:1.

2. The isolated DNA sequence in accordance with claim 1, wherein said DNA sequence encodes an ETS2 Repressor Factor protein having an amino acid sequence comprising SEQ ID NO:2.

3. An isolated DNA sequence which encodes an ETS2 Repressor Factor (ERF) protein, said ETS2 Repressor Factor protein having an amino acid sequence comprising SEQ ID NO:2.

4. The isolated DNA sequence in accordance with claim 1 wherein said isolated DNA sequence hybridizes under high stringency conditions to an ETS2 Repressor Factor gene in human genomic library, said ETS2 Repressor Factor gene having a nucleic acid sequence comprising SEQ ID NO:1.

5. The isolated DNA sequence in accordance with claim 3 wherein said isolated DNA sequence has a nucleic acid sequence comprising SEQ ID NO: 1.

6. An isolated DNA sequence which encodes an ETS2 Repressor factor protein, said ETS2 Repressor Factor protein specifically binding to a polyclonal antibody generated against an immunogen having an amino acid sequence comprising SEQ ID NO:2.

7. An isolated DNA sequence which encodes an ETS2 Repressor Factor protein and said DNA sequence hybridizes under high stringency conditions to an ETS2 Repressor Factor gene in a human genomic library, said ETS2 Repressor Factor gene having a nucleic acid sequence comprising SEQ ID NO:3.

8. An isolated DNA sequence, wherein said DNA sequence encodes a human ETS2 Repressor Factor protein having an amino acid sequence comprising SEQ ID NO: 4.

9. An isolated DNA sequence which encodes a human ETS2 Repressor Factor protein, said human ETS2 Repressor Factor protein having an amino acid sequence comprising SEQ ID NO:4.

10. The isolated DNA sequence in accordance with claim 9 wherein said isolated DNA sequence hybridizes under high stringency conditions to an ETS2 Repressor Factor gene in a human genomic library, said ETS2 Repressor Factor gene having a nucleic acid sequence comprising SEQ ID NO:3.

11. The isolated DNA sequence in accordance with claim 9 wherein said isolated DNA sequence has a nucleic acid sequence comprising SEQ ID NO: 3.

12. An isolated DNA sequence which encodes an ERF protein, said ETS2 Repressor Factor protein specifically binding to a polyclonal antibody generated against an immunogen having an amino acid sequence comprising SEQ ID NO:4.

* * * * *